(12) United States Patent
Ruppert et al.

(10) Patent No.: US 7,364,868 B2
(45) Date of Patent: Apr. 29, 2008

(54) KRÜPPEL-LIKE TRANSCRIPTIONAL FACTOR KLF4/GKLF AND USES THEREOF

(75) Inventors: J. Michael Ruppert, Birmingham, AL (US); Jeffrey Allen Engler, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 445 days.

(21) Appl. No.: 10/776,133

(22) Filed: Feb. 11, 2004

(65) Prior Publication Data

US 2004/0235073 A1    Nov. 25, 2004

Related U.S. Application Data

(63) Continuation-in-part of application No. 10/194,527, filed on Jul. 12, 2002, now abandoned, which is a continuation-in-part of application No. 09/572,224, filed on May 17, 2000, now abandoned.

(60) Provisional application No. 60/134,936, filed on May 19, 1999, now abandoned.

(51) Int. Cl.
  *G01N 33/50*  (2006.01)
  *G01N 33/574*  (2006.01)
(52) U.S. Cl. ........................ 435/7.23; 435/40.5; 436/64
(58) Field of Classification Search .................... None
  See application file for complete search history.

(56) References Cited

OTHER PUBLICATIONS

Clark (Protein Engineering of Antibody Molecules for Prophylactic and Therapeutic Applications in Man, 1993, p. 1).*
Ohnishi et al, BBRC, 2003, vol. 308, pp. 251-256.*
Zhao et al, Oncogene, 2004, vol. 23, pp. 395-402.*
Wang et al, World J of Gastroenterology, 2002, vol. 8, pp. 966-970.*

* cited by examiner

*Primary Examiner*—Karen A. Canella
(74) *Attorney, Agent, or Firm*—Needle & Rosenberg, P.C.

(57) ABSTRACT

The present invention proivdes methods of identifying new carcinoma oncogenes or analyzing functions of known carcinoma oncogenes by transformation of RK3E cells. Also provided are methods of using nuclear localization of Krüppel-like factor 4 (KLF4, or termed Gut-Enriched Krüppel-Like Factor, GKLF) as a marker and prognostic factor for aggressive early-stage breast carcinoma.

10 Claims, 26 Drawing Sheets

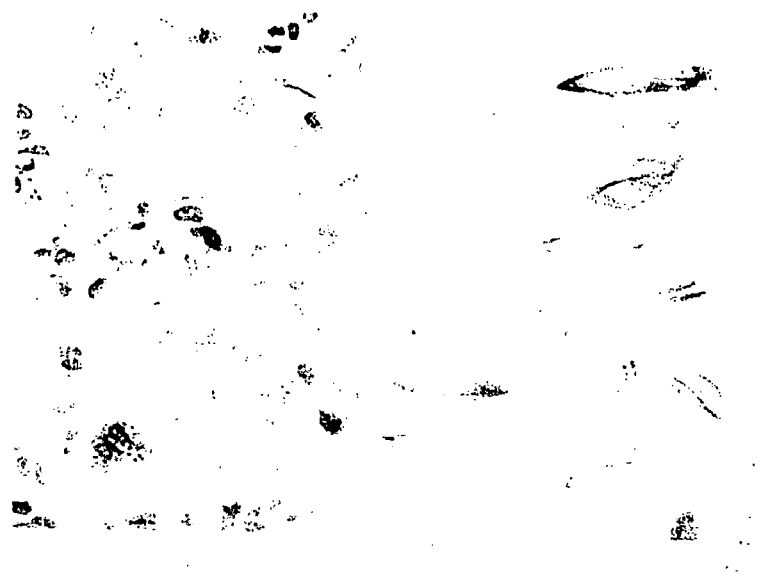
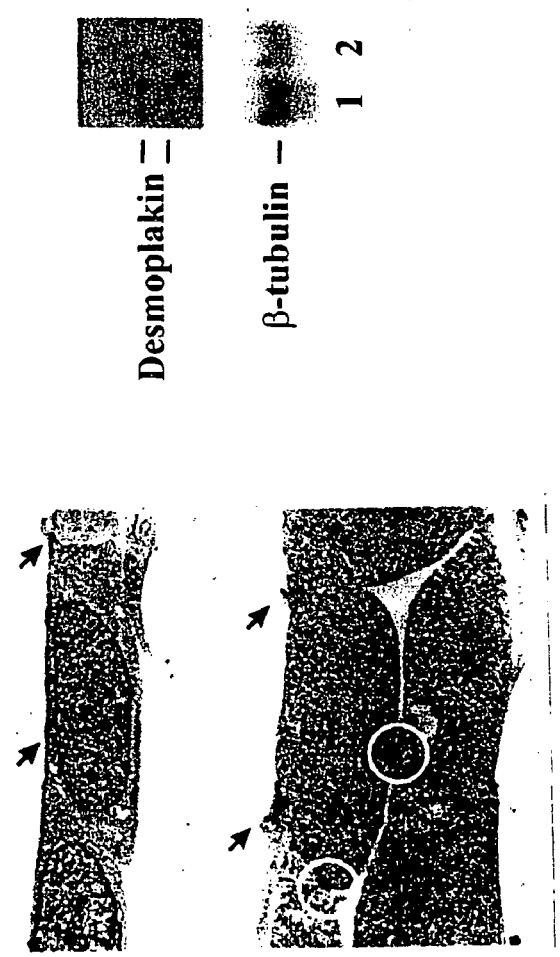
Fig. 1C
Fig. 1B
Fig. 1A

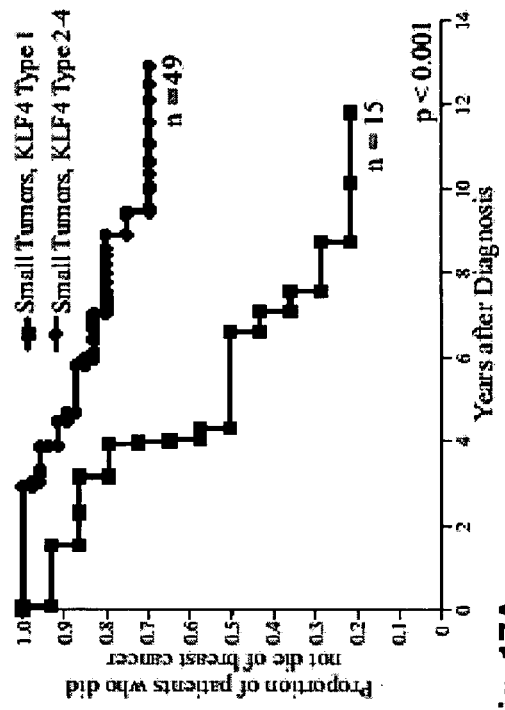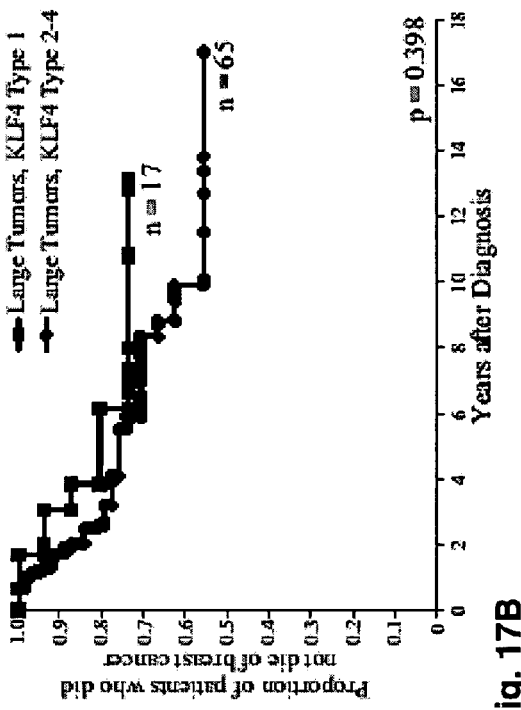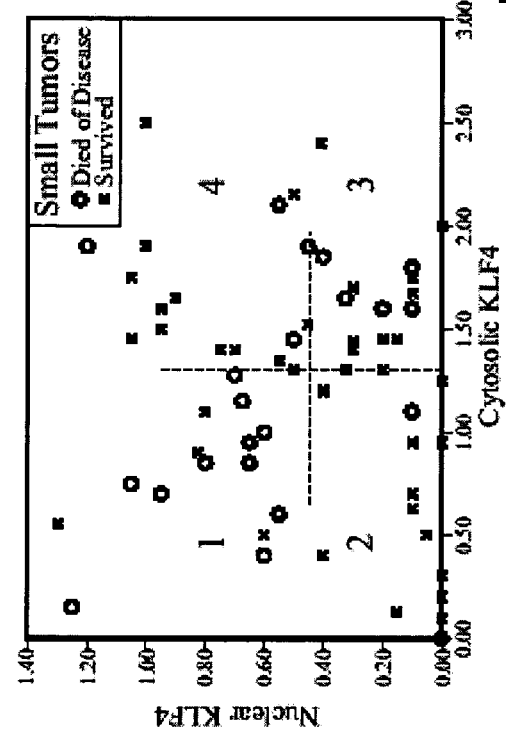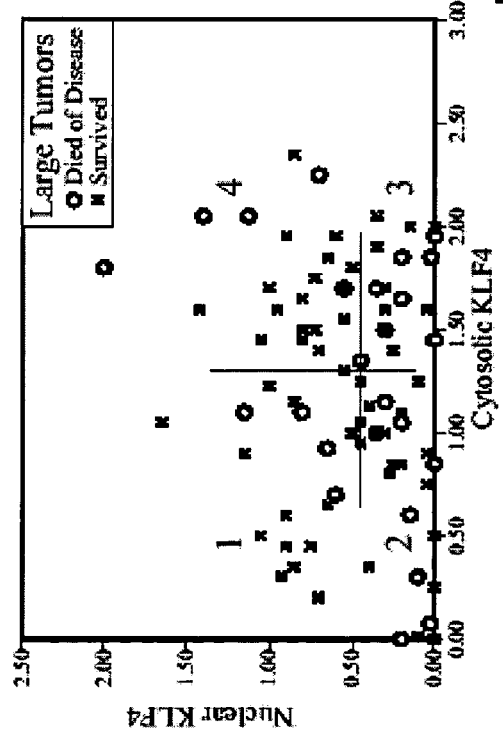
Fig. 17A
Fig. 17B

SEQUENCE LISTING

```
<160> NUMBER OF SEQ ID NOS: 8

<210> SEQ ID NO 1
<211> LENGTH: 13
<212> TYPE: DNA
<213> ORGANISM: Artificial sequence
<220> FEATURE:
<223> OTHER INFORMATION: phosphorylated Bst XI adaptor

<400> SEQUENCE: 1
tcagttactc agg                                                         13

<210> SEQ ID NO 2
<211> LENGTH: 17
<212> TYPE: DNA
<213> ORGANISM: Artificial sequence
<220> FEATURE:
<223> OTHER INFORMATION: phosphorylated Bst XI adaptor

<400> SEQUENCE: 2
cctgagtaac tgacaca                                                     17

<210> SEQ ID NO 3
<211> LENGTH: 20
<212> TYPE: DNA
<213> ORGANISM: Artificial sequence
<220> FEATURE:
<223> OTHER INFORMATION: PCR primer used for recovery of proviral
      inserts

<400> SEQUENCE: 3
cctcactcct tctctagctc                                                  20

<210> SEQ ID NO 4
<211> LENGTH: 23
<212> TYPE: DNA
<213> ORGANISM: Artificial sequence
<220> FEATURE:
<223> OTHER INFORMATION: PCR primer used for recovery of proviral
      inserts

<400> SEQUENCE: 4
aacaaattgg actaatcgat acg                                              23

<210> SEQ ID NO 5
```

<211> LENGTH: 2639
<212> TYPE: DNA
<213> ORGANISM: Homo sapiens
<220> FEATURE:
<223> OTHER INFORMATION: cDNA sequence of GKLF

<400> SEQUENCE: 5

| | |
|---|---:|
| tcgaggcgac cgcgacagtg gtgggggacg ctgctgagtg aagagagcg | 50 |
| cagcccggcc accggaccta cttactcgcc ttgctgattg tctattttg | 100 |
| cgtttacaac ttttctaaga acttttgtat acaaaggaac tttttaaaaa | 150 |
| agacgcttcc aagttatatt taatccaaag aagaaggatc tcggccaatt | 200 |
| tggggttttg ggttttggct tcgtttcttc tcttcgttga ctttggggtt | 250 |
| caggtgcccc agctgcttcg ggctgccgag gaccttctgg gccccacat | 300 |
| taatgaggca gccacctggc gagtctgaca tggctgtcag cgacgcgctg | 350 |
| ctcccatctt tctccacgtt cgcgtctggc ccggcgggaa gggagaagac | 400 |
| actgcgtcaa gcaggtgccc cgaataaccg ctggcgggag gagctctccc | 450 |
| acatgaagcg acttcccca gtgcttccg gccgcccta tgacctggcg | 500 |
| gcggcgaccg tggccacaga cctggagagc ggcggagccg gtgcggcttg | 550 |
| cggcggtagc aacctggcgc ccctacctcg gagagagacc gaggagttca | 600 |
| acgatctcct ggacctggac tttattctct ccaattcgct gacccatcct | 650 |
| ccggagtcag tggccgccac cgtgtcctcg tcagcgtcag cctcctcttc | 700 |
| gtcgtcgccg tcgagcagcg gccctgccag cgcgccctcc acctgcagct | 750 |
| tcacctatcc gatccgggcc gggaacgacc cgggcgtggc gccgggcggc | 800 |
| acgggcggag gcctcctcta tggcagggag tccgctcccc ctccgacggc | 850 |
| tcccttcaac ctggcggaca tcaacgacgt gagcccctcg gcggcttcg | 900 |
| tggccgagct cctgcggcca gaattggacc cggtgtacat tccgccgcag | 950 |
| cagccgcagc cgccaggtgg cgggctgatg ggcaagttcg tgctgaaggc | 1000 |
| gtcgctgagc gcccctggca gcgagtacgg cagcccgtcg gtcatcagcg | 1050 |
| tcagcaaagg cagccctgac ggcagccacc cggtggtggt ggcgccctac | 1100 |
| aacggcgggc cgccgcgcac gtgccccaag atcaagcagg aggcggtctc | 1150 |
| ttcgtgcacc cacttgggcg ctggaccccc tctcagcaat ggccaccggc | 1200 |
| cggctgcaca cgacttcccc ctggggcggc agctccccag caggactacc | 1250 |
| ccgaccctgg gtcttgagga agtgctgagc agcagggact gtcaccctgc | 1300 |
| cctgccgctt cctcccggct tccatcccca cccggggccc aattacccat | 1350 |
| ccttcctgcc cgatcagatg cagccgcaag tcccgccgct ccattaccaa | 1400 |
| gagctcatgc cacccggttc ctgcatgcca gaggagccca agccaaagag | 1450 |
| gggaagacga tcgtggcccc ggaaaaggac cgccacccac acttgtgatt | 1500 |
| acgcgggctg cggcaaaacc tacacaaaga gttcccatct caaggcacac | 1550 |
| ctgcgaaccc acacaggtga gaaaccttac cactgtgact gggacggctg | 1600 |
| tggatggaaa ttcgcccgct cagatgaact gaccaggcac taccgtaaac | 1650 |
| acacggggca ccgcccgttc cagtgccaaa aatgcgaccg agcatttttcc | 1700 |
| aggtcggacc acctcgcctt acacatgaag aggcatttt aaatcccaga | 1750 |
| cagtggatat gacccacact gccagaagag aattcagtat ttttttactttt | 1800 |

-continued

| | |
|---|---|
| tcacactgtc ttcccgatga gggaaggagc ccagccagaa agcactacaa | 1850 |
| tcatggtcaa gttcccaact gagtcatctt gtgagtggat aatcaggaaa | 1900 |
| aatgaggaat ccaaaagaca aaaatcaaag aacagatggg gtctgtgact | 1950 |
| ggatcttcta tcattccaat tctaaatccg acttgaatat tcctggactt | 2000 |
| acaaaatgcc aaggggtga ctggaagttg tggatatcag ggtataaatt | 2050 |
| atatccgtga gttgggggag ggaagaccag aattcccttg aattgtgtat | 2100 |
| tgatgcaata taagcataaa agatcacctt gtattctctt taccttctaa | 2150 |
| aagccattat tatgatgtta aagaagagg aagaaattca ggtacagaaa | 2200 |
| acatgtttaa atagcctaaa tgatggtgct tggtgagtct tggttctaaa | 2250 |
| ggtaccaaac aaggaagcca agttttcaa actgctgcat actttgacaa | 2300 |
| ggaaaatcta tatttgtctt ccgatcaaca tttatgacct aagtcaggta | 2350 |
| atatacctgg tttacttctt tagcattttt atgcagacag tctgttatgc | 2400 |
| actgtggttt cagatgtgca ataatttgta caatggttta ttcccaagta | 2450 |
| tgccttaagc agaacaaatg tgttttcta tatagttcct tgccttaata | 2500 |
| aatatgtaat ataaatttaa gcaaacgtct attttgtata tttgtaaact | 2550 |
| acaaagtaaa atgaacattt tgtggagttt gtattttgca tactcaaggt | 2600 |
| gagaattaag ttttaaataa acctataata ttttatctg | 2639 |

<210> SEQ ID NO 6
<211> LENGTH: 470
<212> TYPE: PRT
<213> ORGANISM: Homo sapiens
<220> FEATURE:
<223> OTHER INFORMATION: amino acid sequence of GKLF protein

<400> SEQUENCE: 6

Met Ala Val Ser Asp Ala Leu Leu Pro Ser Phe Ser Thr Phe Ala
                5                  10                 15

Ser Gly Pro Ala Gly Arg Glu Lys Thr Leu Arg Gln Ala Gly Ala
               20                  25                 30

Pro Asn Asn Arg Trp Arg Glu Leu Ser His Met Lys Arg Leu
               35                  40                 45

Pro Pro Val Leu Pro Gly Arg Pro Tyr Asp Leu Ala Ala Ala Thr
               50                  55                 60

Val Ala Thr Asp Leu Glu Ser Gly Gly Ala Gly Ala Ala Cys Gly
               65                  70                 75

Gly Ser Asn Leu Ala Pro Leu Pro Arg Arg Glu Thr Glu Glu Phe
               80                  85                 90

Asn Asp Leu Leu Asp Leu Asp Phe Ile Leu Ser Asn Ser Leu Thr
               95                 100                105

His Pro Pro Glu Ser Val Ala Ala Thr Val Ser Ser Ser Ala Ser
              110                 115                120

Ala Ser Ser Ser Ser Pro Ser Ser Ser Gly Pro Ala Ser Ala
              125                 130                135

Pro Ser Thr Cys Ser Phe Thr Tyr Pro Ile Arg Ala Gly Asn Asp
              140                 145                150

Pro Gly Val Ala Pro Gly Gly Thr Gly Gly Gly Leu Leu Tyr Gly
              155                 160                165

Arg Glu Ser Ala Pro Pro Pro Thr Ala Pro Phe Asn Leu Ala Asp

```
                170                 175                 180

Ile Asn Asp Val Ser Pro Ser Gly Gly Phe Val Ala Glu Leu Leu
                185                 190                 195

Arg Pro Glu Leu Asp Pro Val Tyr Ile Pro Pro Gln Gln Pro Gln
                200                 205                 210

Pro Pro Gly Gly Gly Leu Met Gly Lys Phe Val Leu Lys Ala Ser
                215                 220                 225

Leu Ser Ala Pro Gly Ser Glu Tyr Gly Ser Pro Ser Val Ile Ser
                230                 235                 240

Val Ser Lys Gly Ser Pro Asp Gly Ser His Pro Val Val Val Ala
                245                 250                 255

Pro Tyr Asn Gly Gly Pro Pro Arg Thr Cys Pro Lys Ile Lys Gln
                260                 265                 270

Glu Ala Val Ser Ser Cys Thr His Leu Gly Ala Gly Pro Pro Leu
                275                 280                 285

Ser Asn Gly His Arg Pro Ala Ala His Asp Phe Pro Leu Gly Arg
                290                 295                 300

Gln Leu Pro Ser Arg Thr Thr Pro Thr Leu Gly Leu Glu Glu Val
                305                 310                 315

Leu Ser Ser Arg Asp Cys His Pro Ala Leu Pro Leu Pro Pro Gly
                320                 325                 330

Phe His Pro His Pro Gly Pro Asn Tyr Pro Ser Phe Leu Pro Asp
                335                 340                 345

Gln Met Gln Pro Gln Val Pro Pro Leu His Tyr Gln Glu Leu Met
                350                 355                 360

Pro Pro Gly Ser Cys Met Pro Glu Glu Pro Lys Pro Lys Arg Gly
                365                 370                 375

Arg Arg Ser Trp Pro Arg Lys Arg Thr Ala Thr His Thr Cys Asp
                380                 385                 390

Tyr Ala Gly Cys Gly Lys Thr Tyr Thr Lys Ser Ser His Leu Lys
                395                 400                 405

Ala His Leu Arg Thr His Thr Gly Glu Lys Pro Tyr His Cys Asp
                410                 415                 420

Trp Asp Gly Cys Gly Trp Lys Phe Ala Arg Ser Asp Glu Leu Thr
                425                 430                 435

Arg His Tyr Arg Lys His Thr Gly His Arg Pro Phe Gln Cys Gln
                440                 445                 450

Lys Cys Asp Arg Ala Phe Ser Arg Ser Asp His Leu Ala Leu His
                455                 460                 465

Met Lys Arg His Phe
                470

<210> SEQ ID NO 7
<211> LENGTH: 6
<212> TYPE: RNA
<213> ORGANISM: Artificial sequence
<220> FEATURE:
<223> OTHER INFORMATION: polyadenylation signal

<400> SEQUENCE: 7 aauaaa                                                                 6

<210> SEQ ID NO 8
<211> LENGTH: 7
<212> TYPE: DNA
<213> ORGANISM: Artificial sequence
```

```
<220> FEATURE:
<223> OTHER INFORMATION: minimal essential binding site for GKLF protein

<400> SEQUENCE: 8 rrggygy                                                                    7
```

KRÜPPEL-LIKE TRANSCRIPTIONAL FACTOR KLF4/GKLF AND USES THEREOF

CROSS-REFERENCE TO RELATED APPLICATION

This is a continuation-in-part application of non-provisional application Ser. No. 10/194,527, filed Jul. 12, 2002, now abandoned which is a continuation-in-part application of Ser. No. 09/572,224, filed May 17, 2000, now abandoned which claims benefit of provisional patent application 60/134,936, filed May 19, 1999, now abandoned.

FEDERAL FUNDING LEGEND

This invention was produced in part using funds obtained through NIH grants RO1 CA65686, P50 CA89019, T32 CA91078 and T32 DK07488. Consequently, the federal government has certain rights in this invention.

BACKGROUND OF THE INVENTION

1. Field of the Invention

The present invention relates generally to molecular oncology. More specifically, the present invention relates to oncogene identification by transformation of RK3E cells and uses thereof. Even more specifically, the present invention relates to the newly identified oncogene Gut-Enriched Krüppel-Like Factor/Epithelial Zinc Finger (GKLF, or termed KLF4, Krüppel-like factor 4) and applications of such gene in medical diagnosis and treatment.

2. Description of the Related Art

Cellular oncogenes have been isolated by characterization of transforming retroviruses from animal tumors, by examination of the breakpoints resulting from chromosomal translocation, and by expression cloning of tumor DNA molecules using mesenchymal cells such as NIH3T3. Several human tumor types exhibit loss-of-function mutations in a tumor suppressor gene that lead to activation of a specific oncogene in a large proportion of tumors. For example, c-MYC expression is regulated by the APC colorectal tumor suppressor; expression of GLI is activated by loss-of-function of PTC in human basal cell carcinoma and in animal models; E2F is activated by loss-of-function of the retinoblastoma susceptibility protein $p105^{Rb}$; and RAS GTPase activity is regulated by the familial neurofibromatosis gene NF1. The comparative genomic hybridization assay and related methods have shown that numerous uncharacterized loci in tumors undergo gene amplification. These observations, and the infrequent genetic alteration of known oncogenes in certain tumor types, suggest that novel transforming oncogenes remain to be identified.

One limitation to the isolation of oncogenes has been the paucity of in vitro assays for functional expression cloning, as several oncogenes are known to exhibit cell-type specificity. For example, GLI, BCR-ABL, NOTCH1/TAN1, and the G protein GIP2 have been found to transform immortalized rat cells, but not NIH3T3 or other cells, demonstrating the potential utility of alternate assays for oncogene expression cloning. While most studies have used NIH3T3 or other mesenchymal cells as host for analysis of oncogenes relevant to carcinoma, the potential utility of a host cell with epithelial characteristics has been discussed.

The prior art is deficient in methods of identifying carcinoma oncogenes by utilizing a host cell with epithelial characteristics. The present invention fulfills this long-standing need and desire in the art by disclosing methods of oncogene identification that involves transformation of RK3E cells.

SUMMARY OF THE INVENTION

RK3E cells, immortalized by E1A, were previously utilized to demonstrate the transforming activity of GLI. The present invention demonstrates that these cells exhibit multiple features of epithelia and detect known and novel transforming activities in tumor cell lines. The epithelial features of the cells and/or the mechanism of immortalization may explain the surprising sensitivity and specificity of the assay compared with previous expression cloning approaches. Three of the four genes known to transform RK3E cells are activated by genetic alterations in carcinomas, and of these genes only RAS exhibits transforming activity in the commonly-used host NIH3T3.

The present invention describes an RK3E assay for oncogene identification and oncogene-specificity drug screening. As a result of the assay, a zinc finger protein of the Krüppel family termed KLF4 (Krüppel-like factor 4) or GKLF was hereby identified as an oncogene expressed in the differentiating compartment of epithelium and misexpressed in dysplastic epithelium. The functional similarities shared with other oncogenes including GLI or c-MYC identify GKLF/KFL4 as an attractive candidate gene relevant to tumor pathogenesis.

The present invention further describes that GKLF/KFL4 can be used in medical evaluation and treatment. A mouse monoclonal antibody to human KLF4 (anti-KLF4) was used to analyze KLF4 expression in multiple normal tissues and cancers. Initially, it was observed that subcellular localization was mixed, with prominent expression in both the nucleus and cytoplasm. Further studies indicate that KLF4 exhibited distinct patterns of subcellular localization in different primary breast tumors. Preferential nuclear localization of KLF4 in surgically excised tumors of patients with early stage disease correlated with eventual death due to breast cancer, and with other parameters previously associated with increased risk of recurrence or death. Small primary tumors with preferential nuclear localization of KLF4 were much more likely to lead to death from breast cancer, and may be distinct with respect to mechanisms of pathogenesis, mechanisms of metastasis, or response to specific therapies. These results indicate that localization of KLF4 in the nucleus of breast cancer cells is a prognostic factor, and KLF4 is a marker of an aggressive phenotype in early-stage infiltrating ductal carcinoma.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIGS. 1A-B show that RK3E exhibit characteristics of epithelial cells. FIG. 1A: Confluent RK3E cells in a culture dish were fixed and stained with uranyl acetate and lead citrate, and ultra-thin sections were examined using a Hitachi 7000 transmission electron microscope. The upper surface was exposed to growth media, and the lower surface was adherent. Electron dense aggregates typical of adherens junctions (arrows) and desmosomes (circled) are shown. Bars, 3.2 μm (top panel) or 1.3 μm (bottom panel). FIG. 1B: Northern blot analysis of RK3E cells (lane 1) and REF52 fibroblasts (lane 2). The filter was hybridized sequentially to a desmoplakin probe (upper) and then to β-tubulin (lower). FIG. 1C: Vimentin expression by immunocytochemistry in RK3E (top) and REF52 (bottom) cells. Bars, 100 μm.

FIG. 2A: Identification of human cDNAs present in transformed RK3E cell lines SQC1-SQC13 (derived using a squamous cell carcinoma library, lanes 1 and 3-14) and BR1 (derived using a breast carcinoma library, lane 15). The polymerase chain reaction (PCR) was used in combination with vector-derived primers and cell line genomic DNA. RK3E genomic DNA served as a negative control template (lane 2). No cDNA was retrieved from cell line SQC3 (lane 4). All foci identified in the screen are represented. Molecular weight markers are indicated on the left in kilobase-pairs. FIG. 2B: Reconstitution of transforming activity by cloned PCR products. cDNAs were cloned into a retroviral expression plasmid, packaged into virus using BOSC23 cells, and applied to RK3E cells. Foci were fixed and stained at 3-4 weeks. Vector: pCTV3K; Control: pCTV3K-SQC1; c-MYC: pCTV3K-BR1; GKLF: pCTV3K-SQC7. FIG. 2C: Morphology of foci and cloned cell lines. Top to bottom: first panel, low power phase contrast view of adjacent foci in a dish transduced with retrovirus encoding GKLF; bar, 900 μm. Second through fourth panels: high power phase contrast view; bar, 230 μm; second panel, RK3E cells at subconfluence; third panel, GKLF-transformed RK3E cells; fourth panel, c-MYC-transformed RK3E cells.

FIG. 3A: Analysis of transgene expression in RK3E cells and derivative cell lines transformed by the indicated oncogene. Lane 1: RK3E cells in exponential growth phase; lane 2: RK3E incubated at confluence for five days. Ethidium bromide-stained RNA is shown below after transfer to the filter. FIG. 3B: Endogenous GKLF (3.0 kb) or c-MYC (2.3 kb) expression in tumor cell lines. Lanes 1-3: breast cancer lines; lanes 4-6: squamous cell carcinoma lines. FIG. 3C: Analysis of gene expression in laryngeal squamous cell carcinoma. Lane 1: SCC25 cell line; lanes 3-6, 9, 12: primary tumors; lanes 7, 8, 10 and 11: metastatic tumors. Lanes 3-12 correspond to case numbers 5, 8, 18-20, 6, and 21-24, respectively (see Table 4). RK3E-RAS cell RNA served as a negative control (lane 2), while hybridization to β-tubulin served as a control for loading.

FIG. 4A: Oropharyngeal squamous cell carcinoma. Cell lines (lanes 2-4) and tumors (lanes 5-15) are shown. FIG. 4B: Breast carcinoma. Cell lines (lanes 2-5) and tumors (lanes 6-14) are shown.

FIG. 6B shows invasive ductal carcinoma admixed with cords of stroma. Scale bars=160 μm.

FIG. 8A, uninvolved oral epithelium (left) and invasive oral squamous cell carcinoma (right). Arrowheads indicate the basal cell layer, while arrows indicate invasive carcinoma. Staining of tumor cells and of superficial epithelial cells is indicated by a brown precipitate. FIG. 8B, a section of small bowel illustrating increased staining of superficial epithelium (left) compared to cells deeper within crypts (right). FIG. 8C, a case of colorectal carcinoma, with increased staining of uninvolved superficial mucosa (left) compared to adjacent tumor cells (right). Scale bar for C (left panel)=45 μm; other scale bars=140 μm.

FIG. 9A shows a tissue section containing uninvolved epithelium (left, arrowheads) adjacent to invasive carcinoma (right); FIG. 9B shows a different case showing invasive carcinoma cells with a mixed nuclear and cytoplasmic staining pattern. FIG. 9C shows a tissue section containing an uninvolved duct (left panel) adjacent to both DCIS (right panel, arrows) and invasive carcinoma (right panel, arrowheads). Scale bars: A=120 µm; B=30 µm; C=60 µm.

FIG. 13A shows the staining pattern of low cytoplasmic GKLF/high nuclear GKLF vs. all other profiles. FIG. 13B shows the staining pattern of low cytoplasmic GKLF/high nuclear GKLF vs. high cytoplasmic GKLF/low nuclear GKLF.

FIGS. 14A, Each panel illustrates a different case of primary breast cancer. Staining patterns were predominantly nuclear (left panels), predominantly cytoplasmic (middle panels), or mixed nuclear and cytoplasmic (right panels). Staining is indicated as a brown precipitate. Unstained nuclei appear blue due to the hematoxylin counterstain. Arrowheads indicate the area detailed at higher-fold magnification in the inset. FIGS. 14B, Scatter-plot analysis of 146 cases of primary infiltrating ductal carcinoma of the breast. Nuclear and cytosolic staining was scored on a scale from 0-4, where 0 represents no detectable staining and 4.0 represents saturation. A broken line indicates the median score for nuclear (0.45) or cytoplasmic (1.29) staining. Some data points represent two or more cases with the same score. The quadrants defined by the median scores were used to designate the KLF4 staining pattern as Type 1, 2, 3, or 4. Scale bar for A=100 mm.

FIGS. 15A, all patients regardless of stage at diagnosis. FIGS. 15B, patients with early stage disease only. FIGS. 15C, patients with early stage disease and small primary tumors. n, the number of patients in each group. Type 1 indicates tumors with nuclear staining>median and cytosolic staining<median, and Type 2-4 indicates all other cases.

FIGS. 16A, Patients with Type 1 staining. FIGS. 16B, All other patients (i.e., Type 2-4 staining).

FIGS. 17A-B shows disease-specific survival according to KFL4 staining pattern in small and large breast tumors (all stages of disease). FIGS. 17A, Small tumors (≦2.0 cm in diameter in greatest dimension). FIGS. 17B, Large tumors (>2.0 cm in greatest dimension). Scatter-plot (left panels) and Kaplan-Meier analysis (right panels) are shown. Broken lines (left panels) indicate the median scores in the cytosol and nucleus for all patients combined. For the scatter-plots, some scores were adjusted by ±0.05 so that each case in the study is represented by a distinct data point.

FIGS. 18A, The human KLF4 cDNA was modified at the amino terminus by addition of a hemagglutinin (HA) epitope. HEK293 cells were analyzed 48 hours following transfection of HA-KLF4 (ANTI-HA, shown in red, left panel). Subcellular localization was determined by comparison to DAPI-stained nuclei (shown in blue, middle panel) and by expression of Green Fluorescent Protein (GFP, shown in green, right panel). Co-localization of HA-KLF4 and DAPI results in a pink color. Cells transfected with empty vector were analyzed in parallel and served as a negative control (lower panels). FIGS. 18B, RK3E cells were transformed using an HA-KLF4 expression vector. HA-KLF4 cells (upper panel) or vector control cells (lower panel) were analyzed using ANTI-HA (shown in red, left panel). DAPI (shown in blue, middle panel) and phalloidin (shown in green, right panel) allowed visualization of the nucleus and cytoplasm, respectively. Scale bar for A=50 mm; scale bar for B=20 mm. Insets show the boxed areas at higher magnification.

DETAILED DESCRIPTION OF THE INVENTION

Figure 2A:
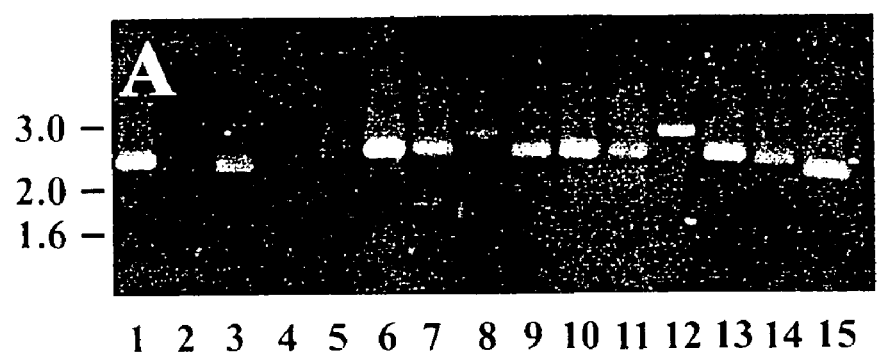
FIGS. 2A-C show expression cloning of c-MYC and GKLF.

The function of several known oncogenes is restricted to specific host cells in vitro, suggesting that new genes may be identified by using alternate hosts. RK3E cells exhibit characteristics of epithelia and are susceptible to transformation by the G protein RAS and the zinc finger protein GLI. The present invention demonstrates that transformation of RK3E represents a significant improvement over NIH3T3 transformation that are often used for oncogene analysis in vitro. RK3E assay can detect carcinoma oncogenes with sensitivity. Of the five genes disclosed in the present invention that function in RK3E cells, i.e., RAS, GKLF, c-MYC, GLI and SCC7, only RAS transforms NIH3T3 cells. RK3E assay can also detect new oncogenes with specificity, i.e., without artifacts from truncation or rearrangement. In addition, RK3E cells are diploid and genetically stable.

Expression cloning identified the major transforming activities in squamous cell carcinoma cell lines as c-MYC and the zinc finger protein Gut-Enriched Krüppel-Like Factor/Epithelial Zinc Finger (GKLF/KFL4). In oral squamous epithelium, GKLF/KFL4 expression was detected in the upper, differentiating cell layers. In dysplastic epithelium, GKLF/KFL4 expression was prominently increased and was detected diffusely throughout the entire epithelium, indicating that GKLF/KFL4 is misexpressed in the basal compartment early during tumor progression. The results demonstrate transformation of epithelioid cells to be a sensitive and specific assay for oncogenes activated during tumorigenesis in vivo, and identify GKLF/KFL4 as an oncogene that may function as a regulator of proliferation or differentiation in epithelia.

In situ hybridization, Northern blot analysis, and immunohistochemistry were used to detect GKLF/KFL4 at various stages of tumor progression in the breast, prostate, and colon. Overall, expression of KFL4 mRNA was detected by in situ hybridization in 21 of 31 cases (68%) of carcinoma of the breast. Low-level expression of KFL4 mRNA was observed in morphologically normal (uninvolved) breast epithelium adjacent to tumor cells. Increased expression was observed in neoplastic cells compared with adjacent uninvolved epithelium for 14 of 19 cases examined (74%). Ductal carcinoma in situ exhibited similar expression as invasive carcinoma, suggesting that KFL4 is activated prior to invasion through the basement membrane. Expression as determined by Northern blot was increased in most breast tumor cell lines and in immortalized human mammary epithelial cells (HMECs) when these were compared with finite-lifespan human mammary epithelial cells. Alteration of KFL4 expression was confirmed by use of a novel monoclonal antibody that detected the protein in normal and neoplastic tissues in a distribution consistent with localization of the mRNA. In contrast to most breast tumors, expression of KFL4 in tumor cells of colorectal or prostatic carcinomas was reduced or unaltered compared with normal epithelium. The results demonstrate that KFL4 expression in epithelial compartments is altered in a tissue-type specific fashion during tumor progression, and suggest that increased expression of KFL4 mRNA and protein may contribute to the malignant phenotype of breast tumors.

An additional 146 cases of breast cancer were examined by immunohistochemical staining in order to determine whether expression of KLF4 is associated with specific clinical, pathologic, or molecular features. Subcellular localization exhibited case-to-case variation. Tumors with high nuclear staining and low cytoplasmic staining were termed Type 1. For patients with early stage disease (i.e., Stage I or IIA), Type 1 staining was associated with eventual death due to breast cancer (hazard ratio, 2.8; 95% confidence interval, 1.23-6.58; P=0.011). The association was stronger in patients with early stage cancer and small primary tumors (i.e., $\leq 2.0$ cm in diameter, (designated as Ti); hazard ratio, 4.3; 95% confidence interval, 1.75-10.62; P<0.001). For patients with early stage disease, multivariate analysis indicated that Type 1 staining was independently associated with outcome (adjusted hazard ratio 2.6; 95% confidence interval, 1.10-6.05; P=0.029). These results indicate that localization of KLF4 in the nucleus of breast cancer cells is a prognostic factor, and identify KLF4 as a marker of an aggressive phenotype in early-stage infiltrating ductal carcinoma.

Type 1 staining was associated not only with death due to breast cancer, but also with high histologic grade in the primary tumor, a well-recognized correlate of survival. Type 1 staining was associated with high histologic grade (P=0.032), increased expression of Ki67 (P=0.016), and reduced expression of BCL2 (P=0.032). The association with grade, like the association with clinical outcome, was restricted to small tumors. As for clinical outcome and histologic grade, the association between Type 1 staining and reduced expression of BCL2 was stronger in small tumors.

Few markers associated with clinical outcome in breast cancer have been found to exhibit tumor size-dependence. Although several possibilities may account for the non-association of Type 1 staining and clinical outcome in large tumors, this result is particularly interesting given recent insights into KLF4 function as a transforming oncogene that induces a slow-growth phenotype. Potentially, the dual roles of KLF4 as both a transforming activity and an inhibitor of cell cycle progression could dissociate malignant potential from tumor size, leading to an aggressive or metastatic phenotype in tumors with a smaller diameter. Alternative explanations include the possibility that, in large tumors, the localization or transcriptional activity of KFL4 in could be influenced by other signaling pathways or by the tumor microenvironment, thus confounding the associations observed in smaller tumors.

The potential utility of prognostic markers in the diagnosis and treatment of breast cancer has been reviewed recently. A benefit of stratification of patients into distinct risk groups by molecular staging is that the utility of known prognostic factors or the effectiveness of specific therapies may be enhanced in one of the subsets. For example, tumor size and stage at diagnosis could be enhanced as prognostic factors following identification and segregation of T1-Type 1 cases, thus allowing for more effective selection of therapies and more efficient design of clinical trials.

Results from the KLF4 immunostaining do not distinguish between active and passive roles for KLF4 in the aggressive phenotype of these early stage tumors. Further insight may come from analysis of KFL4-regulated genes (target genes). Increased expression of target genes in Type 1 tumors vs Type 4 tumors would be consistent with an active role, as Type 4 tumors likewise exhibit elevated nuclear expression of KLF4, but did not exhibit an aggressive phenotype. On the other hand, if preferential nuclear localization were a consequence of signaling through upstream regulators of KLF4, such signaling might promote the aggressive phenotype independently of KLF4, through parallel effector pathways. In this case, KLF4 would have only a passive role, and transcriptional targets might be similarly expressed in Type 1 and Type 4 tumors. Target genes of KLF4 can be identified in experiments using a conditional allele in combination with microarrays.

While KLF4 nuclear localization is associated with clinical outcome in breast cancer, there is currently little evidence of a functional role for KLF4 in tumor progression. Currently, the investigators are utilizing short-term induction of KLF4 expression in vitro to identify transcriptional target genes, and analyzing expression of these putative target genes within Type 1 breast tumors and in a novel mouse model of KLF4-induced neoplasia. These studies may lead to a better understanding of signaling pathways that function upstream or downstream of KLF4, and may indicate whether KFL4 plays an important role in human tumor initiation or progression.

In addition to the nuclear expression observed in vitro, a prominent perinuclear component of KLF4 was detected following transient transfection. This preliminary observation warrants further investigation, since many transcription factors implicated in neoplasia exhibit regulated subcellular localization. The perinuclear staining observed here is consistent with similar regulation of KLF4, perhaps through tethering to a cytoplasmic protein. Interestingly, human KLF4 contains a putative SH3 domain binding site near the aminoterminus that could mediate such an interaction.

The perinuclear localization of KFL4 observed in vitro may provide a simple assay that may facilitate identification of upstream signaling pathways that regulate nuclear import and/or export of KLF4. One interesting candidate is the TGF-β pathway. In vascular smooth muscle cells, TGF-β or other TGF-β-superfamily members induce the expression of smaller KFL4 isoforms, and induce binding of KFL4 to TGF-β control elements found in the regulatory region of marker genes associated with smooth muscle differentiation. The possibility that this perinuclear staining is related to the more diffuse cytoplasmic staining observed in breast tumors also warrants further study.

The present invention provides a method of determining the prognosis of a breast cancer patient based on the expression of Krüppel-like factor 4 (KLF4) in the breast tumor as determined by immunohistochemistry. In a preferred embodiment, the immunohistochemistry employs an anti-KLF4 monoclonal antibody such as monoclonal antibody IE5. Generally, a predominantly cytosolic staining indicates a greater likelihood of survival of the individual or a greater likelihood of response to a specific therapy (e.g., local or loco-regional resection in surgery, chemotherapy agents, radiotherapy, or hormonal therapy). In constrast, a predominantly nuclear staining and a lower cytosolic staining indicates a lower likelihood of survival of the individual or a lower likelihood of response to a specific therapy (e.g., local or loco-regional resection in surgery, chemotherapy agents, radiotherapy, or hormonal therapy).

Predominant nuclear staining of KLF4 protein indicates an aggressive phenotype of early stage infiltrating ductal carcinoma, and the patient is likely to have a stage I or stage IIA breast tumor. This prognostic method is particularly valuable when the tumor is smaller than or equal to about 2 cm, wherein predominant nuclear staining of KLF4 protein is associated with high histologic grade, increased expression of Ki67 and/or reduced expression of BCL2 as compared to tumor without a predominant nuclear staining of KLF4.

The present invention also provides a monoclonal antibody directed against residues 479-1197 of Krüppel-like factor 4 (SEQ ID NO. 6). Such antibody can be used to monitor a treatment, further evaluate effectiveness of the treatment in an individual. Specifically, the monoclonal antibody detects the localization and level of KLF4 protein, and wherein decreases of KLF4 protein level indicate effective response of the individual to the treatment. Still further provided in the present invention is a kit for monitoring a treatment thereby evaluating effectiveness of the treatment in an individual, comprising the monoclonal antibody disclosed herein and a suitable carrier.

In another embodiment of the present invention, there is provided a method of detecting transforming activities of a carcinoma oncogene, comprising the steps of transforming epithelioid cells with the oncogene and then detecting morphological transformation, wherein the presence of transformed cell lines indicates that the oncogene has transforming activities. Preferably, the epithelioid cells are RK3E cells. Representative examples of the oncogene include, but are not limited to, RAS, GKLF, c-MYC, GLI. Still preferably, the disclosed method detects protein coding region of the oncogene without truncation or rearrangement.

In yet another embodiment of the present invention, there is provided a method of identifying oncogenicity of a gene, comprising the steps of transforming epithelioid cells with the gene; detecting transformed cell lines and measuring tumorigenicity of said transformed cell lines by injecting the transformed cell lines into an animal, wherein induction of tumors in the animal indicates that the gene is an oncogene. Preferably, the epithelioid cells are RK3E cells.

The present invention also provides a method of identifying oncogene-specificity of a known drug, comprising the steps of transforming epithelioid cells with the oncogene; detecting transformed cell lines and contacting the transformed cell lines with the drug, wherein if the drug inhibits proliferation or survival of the transformed cell lines, the drug is specific for the oncogene. Preferably, the epithelioid cells are RK3E cells. Still preferably, the oncogene is activated in carcinoma and representative examples of oncogenes include RAS, GKLF, c-MYC, and GLI.

In another embodiment of the present invention, there is provided a method of screening for a drug functioning as an inhibitor of an oncogene, comprising the steps of transforming epithelioid cells with the oncogene; contacting the cells with the test drug and detecting transformed cell lines, wherein absence of transformation or reduced transformation compared to the result obtained without the drug contact indicates the test drug is an inhibitor of the oncogene. Preferably, the epithelioid cells are RK3E cells. Still preferably, the oncogene is activated in carcinoma and examples of the oncogene include RAS, GKLF, c-MYC, GLI.

In still yet another embodiment of the present invention, there is provided a method for identification of oncogene-specific alterations in activity of signal transduction molecules or in the expression of cellular mRNAs, comprising the steps of transforming epithelioid cells with the oncogene; measuring enzyme activity or mRNA expression levels, wherein specific alteration of these parameters indicates the enzyme or mRNA is likely to be regulated by the oncogene. Preferably, the epithelioid cells are RK3E cells. Still preferably, the oncogene is activated in carcinoma and examples of the oncogene include, but are not limited to, RAS, GKLF, c-MYC, GLI.

The present invention is further directed to a method of screening for alterations in enzyme activity, protein expression, or mRNA expression in association with an oncogene, comprising the steps of: transforming epithelioid cells with said oncogene; and measuring said enzyme, protein or mRNA levels or activities; wherein alterations in transformed cell lines vs. in non-transformed cell lines indicate that the oncogene regulates the enzyme activity, protein expression, or mRNA expression. Preferably, the epithelioid cells are RK3E cells and the oncogene is a carcinoma oncogene. Representative oncogene include RAS, GKLF, c-MYC and GLI.

Still further provided is a method of treating an individual having a carcinoma by administering a drug to the individual, wherein the drug inhibits the expression or activity of GKLF. Representative examples of carcinoma include breast carcinoma and oral squamous cell carcinoma.

In yet another embodiment of the present invention, there is provided a method of monitoring a treatment thereby evaluating effectiveness of the treatment in an individual, comprising the step of detecting the expression levels of GKLF in the individual prior to, during and post said treatment, wherein decreases of GKLF expression levels indicate effective response of the individual to the treatment. By doing so, the treatment is monitored and the effectiveness of the treatment is evaluated in the individual. The treatments can be drug administration, radiation therapy, gene therapy, or chemotherapy. The individual may suffer from a carcinoma such as breast carcinoma and oral squamous cell carcinoma.

The present invention also provides DNA fragments encoding a Gut-Enriched Krüppel-Like Factor/Epithelial Zinc Finger (GKLF) protein. The isolated DNA includes (a) DNA that has the sequence of SEQ ID NO.5; (b) isolated DNA which encodes a GET protein that has the sequence of SEQ ID NO.6; and (c) isolated DNA differing from the isolated DNAs of (a) and (b) in codon sequence due to the degeneracy of the genetic code.

The present invention further encompasses recombinant vector capable of expressing the DNA fragment disclosed herein in a cell; host cells transfected with such vector; and isolated and purified GKLF protein coded for by the DNA fragment disclosed herein.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1 cDNA Libraries Construction

To identify transforming genes, mRNA from human squamous cell carcinoma- or breast tumor-derived cell lines was used. These tumor types do not exhibit frequent alteration of RAS or GLI. Two cDNA libraries were constructed using the ZAP-Express™ cDNA synthesis kit (Stratagene, La Jolla, Calif.). A library was prepared from human squamous cell carcinoma cells derived from tumors of the oro-pharynx. Equal quantities of total mRNA from cell lines SCC15, SCC25, and FaDu (ATCC, Rockville, Md.) were pooled. Similarly, equal quantities of mRNA from the breast cancer cell lines MCF-7, ZR75-1, MDAMB-453, and T47D (ATCC) were pooled. For each pool, poly A+ mRNA was selected by two cycles of oligo-dT cellulose affinity chromatography. Five µg was reverse transcribed using an oligo-dT linker primer and MMLV reverse transcriptase. Double-stranded cDNA was synthesized using $E.\ coli$ RNAase H and DNA polymerase I. cDNA was ligated to λZAP EXPRESS™ bacteriophage arms and packaged into virions. The λ titer and the frequency of non-recombinants was determined prior to amplification of the library on bacterial plates (Table 1). The frequency of non-recombinant clones was estimated to be less than 2% by complementation of β-gal activity (blue/white assay).

Phage were converted to pBKCMV plasmids by autoexcision in bacteria. Insert sizes in randomly selected clones were determined at this step by gel electrophoresis of plasmid DNA digested with Sal I and Not I (Table 1). The pBKCMV plasmid libraries were amplified in soft agar at $4 \times 10^4$ colony forming units per ml. After incubation at 37° C. for 15 hrs, bacterial cells within the agar bed were isolated by centrifugation, amplified for 3-4 doublings in culture, and plasmid DNA was purified using a Qiagen column (Qiagen, Inc., Chatsworth, Calif.).

The libraries were high-titer (assessed prior to amplification on agar plates) with a mean insert size of 1.6-1.7 kb. The amplified breast cDNA library was further assessed by plaque screening for the transcription factor hBRF using a probe derived from the 5' end of the protein coding region (bases 315-655, accession U75276). Each of the seven clones identified were derived from independent reverse transcripts, as determined by end sequencing, confirming that complexity of the library was maintained during amplification. The inserts ranged in size from 2.1-3.4 kb, and contained the entire 3' UTR and much or all of the protein coding region intact. Three of the seven extended through the predicted initiator methionine codon, while four others were truncated further downstream. These results suggested that the library is relatively free of C-terminally truncated clones, and contains full-length cDNAs even for relatively long mRNAs. The overall abundance of hBRF mRNA has not been determined.

To generate libraries in a retroviral expression vector, cDNA inserts were excised from 10 µg of plasmid using Sal I and Xho I. After treatment with Klenow and dNTPs and extraction with phenol, the DNA was ligated to 5' phosphorylated Bst XI adaptors (5'-TCAGTTACTCAGG-3' (SEQ ID No. 1) and 5'-CCTGAGTAACTGACACA-3' (SEQ ID No. 2)) as described (Whitehead et al., 1995). After treatment with Not I, excess adaptors were removed by gel filtration, and the residual vector was converted to a 9.0 kb dimer using the Not I site and T4 DNA ligase. The cDNA was size fractionated by electrophoresis in Sea Plaque® agarose (FMC BioProducts, Rockland, Me.) and fragments 0.6-8.5 kb were isolated and ligated to the Bst XI- and alkaline phosphatase-treated MMLV retroviral vector pCTV1B (Whitehead et al., 1995). $E.\ coli$ MC1061/p3 were transformed by electroporation and selected in soft agar as above.

The libraries were analyzed in two retroviral transfection experiments performed on consecutive days. For each library, ten 10 cm-dish of BOSC23 ecotropic packaging cells at 80%-90% confluence were transfected using 30 μg of plasmid DNA per dish. The transfection efficiency for these cells was ~60%, as determined using a β-gal control plasmid. Viruses were collected in a volume of 9.0 mls/dish at 36-72 hours post-transfection, filtered, and the 9.0 mls was expressed into a 10 cm dish containing RK3E cells at ~30% confluence. Polybrene was added to a final concentration of 10 μg/ml. After 15 hours, and every three days thereafter, the cells were fed with growth media. A total of 20 RK3E dishes were transduced for each library. A β-gal retroviral plasmid transduced at least 20-30% of RK3E cells in control dishes. For colony assays hygromycin was used at 100 μg/ml. Cell proliferation rates for transformed cell lines was measured by plating $2\times10^5$ cells in duplicate and counting cells 96 hours later using a hemacytometer.

Proviral inserts were recovered by polymerase chain reaction (PCR). PCR reactions used 200 ng of cell line genomic DNA, 20 mM Tris-HCl (pH 8.8), 87 mM potassium acetate, 1.0 mM $MgCl_2$, 8% glycerol, 2% dimethylsulfoxide, 0.2 mM of each dNTP, 32 pmol of each primer (5'-CCTCACTCCTTCTCTAGCTC-3' (SEQ ID No. 3); 5'-AA-CAAATTGGACTAATCGATACG-3' (SEQ ID No. 4)), 5 units of Taq polymerase (Gibco BRL, Gaithersburg, Md.), and 0.3 units of Pfu polymerase (Stratagene, La Jolla, Calif.) in a volume of 0.05 ml. Cycling profiles were: 95° C. for 1 min; then 95° C. for 10 s, 59° C. for 40 s, 68° C. for 8 min (35 cycles).

By immunocytochemical staining, the mesenchymal marker vimentin was low or undetectable in RK3E cells but was strongly positive in REF52 cells (FIG. 1C). Neither line reacted strongly with anti-cytokeratin or anti-desmin antibodies. Antibodies to vimentin and desmin were from Dako (Carpenteria, Calif.). A cocktail of anti-cytokeratin included AE1/AE3 (Biogenics, San Ramon, Calif.), CAM5.2 (Becton Dickinson, San Jose, Calif.), and MAK-6 (Zymed, So. San Francisco, Calif.). Human tissue served as a positive control for each antibody. No signal was obtained in the absence of primary antibody. These results are consistent with the observation that E1A induces multiple epithelial characteristics without inducing cytokeratin expression.

Karyotype analysis revealed RK3E cells to be diploid with a slightly elongated chromosome 5q as the only apparent abnormality. Importantly, RK3E cells can be transformed by functionally diverse oncogenes such as RAS and GLI. Four such transformed lines were each homogeneous for DNA content, as determined by fluorescence analysis of propidium iodide stained cells derived from RAS-(one line) or GLI-(three lines) induced foci, indicative of a relatively stable genetic constitution. These properties suggested that RK3E cells may serve as an in vitro model for identification and mechanistic analysis of gene products involved in the progression from normal epithelial tissue to malignancy.

TABLE 1

Assessment of cDNA libraries

| Library | λ titer | cDNA size (N, R)[a] | Probe[b] | cDNA clones transduced[c] | Transduced RK3E cells[d] | Foci |
| --- | --- | --- | --- | --- | --- | --- |
| Squamous cell ca. | $8.9 \times 10^6$ | 1.69 (10, 1.0-3.6) | NT | $\sim 4 \times 10^6$ | $\sim 1.2 \times 10^7$ | 13 |
| Breast ca. | $7.4 \times 10^6$ | 1.64 (18, 0.5-2.7) | hBRF | $\sim 4 \times 10^6$ | $\sim 1.2 \times 10^7$ | 1 |

[a]indicates mean size of cDNAs in kilobase-pairs, the number of clones sized by gel electrophoresis (N), and the size range (R).
[b]420,000 plaques were analyzed by hybridization to the 5' end of the RNA polymerase III transcription factor hBRF cDNA. NT, not tested.
[c]The number of clones processed at each step of library construction was equal to or greater than $4 \times 10^6$. The Bst XI adaptor strategy generates recombinant cDNA expression plasmids in an orientation-independent fashion, such that both sense and antisense vectors result.
[d]The number of RK3E cells transduced was estimated as the product of the transduction frequency (20%), the number of dishes screened (20), and the number of cells per dish ($3 \times 10^6$).

EXAMPLE 2

RK3E Cells have Characteristics of Epithelia

RK3E cells are a clone of primary rat kidney cells immortalized by transfection with adenovirus E1A in vitro (Ruppert et al., 1991). The cells exhibit morphological and molecular features that are epithelioid. They are contact-inhibited at confluence and are polarized with apical and basolateral surfaces and electron-dense intercellular junctions typical of adherens junctions and desmosomes (FIG. 1A). Northern blot analysis showed that RK3E cells, but not REF52 fibroblasts, expressed desmoplakin, a major component of desmosomes and an epithelial marker (FIG. 1B).

EXAMPLE 3

Isolation of c-MYC And GKLF/KFL4 by Expression Cloning

The libraries were cloned into the MMLV retroviral expression plasmid pCTV1B (Whitehead et al., 1995), packaged in BOSC23 cells, and high-titer virus supernatants were applied to RK3E cells as described above. Fourteen foci, identified at 10-20 days post-transduction, were individually expanded into cell lines. Thirteen of these contained a single stably integrated cDNA, as indicated by PCR (FIG. 2A). Eleven of these were identified as human c-MYC by end-sequencing and restriction enzyme analysis. The c-MYC cDNA in lane 15 included the coding region and 193 bases of 5' UTR sequence (Accession V00568). As determined by sequencing or restriction mapping, the other c-MYC cDNAs extended further 5' (lanes 1,3,5-7,9-11,13-14), such that all of the clones contained the entire protein-coding region.

In addition, two cell lines (FIG. 2A, lanes 8 and 12) contained cDNAs coding for GKLF/KFL4. Mouse and human GKLF/KFL4 cDNAs were previously isolated by hybridization with zinc finger consensus probes, but were not implicated as oncogenes or found to be induced during neoplastic progression. After cloning into plasmid, the sequences of these two cDNAs, termed SQC7 and SQC11, were obtained in total. Automated sequence analysis was performed for the two independent GKLF/KFL4 isolates using vector-derived primers and sense or antisense primers spaced at 400 bp intervals within the inserts. The complete sequence was obtained for both clones, with one of the clones analyzed for both strands. GKLF/KFL4 sequence was submitted to GenBank (Accession AF105036). The cDNA and amino acid sequences of GKLF/KFL4 are listed in SEQ ID No.5 and SEQ ID No.6, respectively.

As determined by comparison with multiple expressed sequence tags (ESTs) and two full-length coding sequence files in the database (Accessions U70663, AF022184), each of the two GKLF/KFL4 isolates contained the predicted GKLF/KFL4 protein coding region bounded by 5' and 3' UTRs. An ATG in good context for translation initiation was located at base 330, with the predicted terminator codon at base 1740. Both isolates were artificially truncated at the Xho I site in the 5' UTR during library preparation. As the transcripts had been processed using distinct AAUAAA (SEQ ID No. 7) polyadenylation signals, the cDNAs were slightly different in length and derived from independent mRNA molecules (FIG. 2A).

Sequencing revealed these two GKLF/KFL4 isolates to be identical within the residual 5' UTR and throughout the coding region. A single base-pair difference in the 3' UTR represents a PCR-induced error or a rare variant, as determined by comparison with ESTs. Comparison to a placenta-derived sequence (Accession U70663) revealed three single base-pair differences in the coding region. These differences were resolved by alignment with other sequences in the database (Accessions AF022184, AA382289) from normal tissues, indicating that the GKLF/KFL4 molecules obtained by expression cloning are predicted to encode the wild-type protein.

EXAMPLE 4

Reconstitution of Transforming Activity for c-MYC And GKLF/KFL4

Figure 2B:
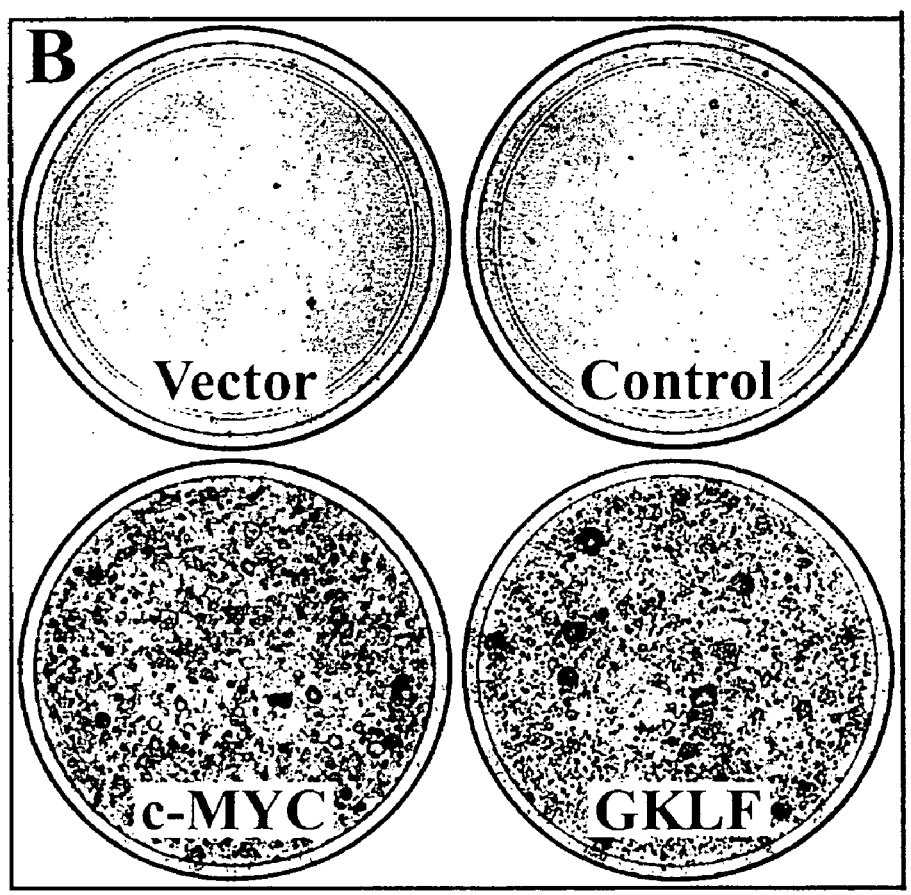
Figure 2C:
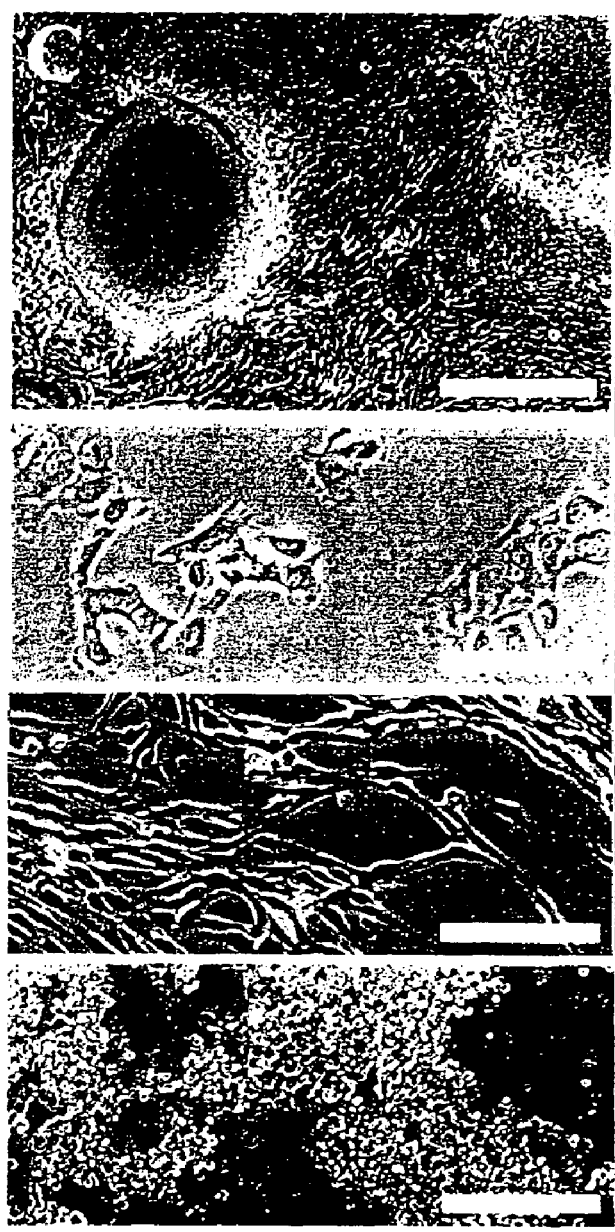

To demonstrate transforming activity, three independent PCR products each for the c-MYC and GKLF cDNAs were cloned into the retroviral expression vector pCTV3K (Whitehead et al., 1995), packaged into virions, and tested for transformation of RK3E cells in vitro (FIGS. 2B and 2C, Table 2). One of the c-MYC clones (pCTV3K-SQC1) possessed greatly reduced transforming activity in multiple experiments despite similar viral titers, as determined by induction of hygromycin resistance, suggesting that an error may have been introduced during PCR. Each of the other virus supernatants carrying GKLF and c-MYC transgenes induced >1000 foci per dish compared to no foci for virus controls.

To determine the efficiency of transformation by GKLF and c-MYC, a colony morphology assay was used as described (Whitehead et al., 1995). Virally transduced cells were selected in hygromycin at low confluence, and stable colonies were fixed, stained, and scored for morphological transformation by visual inspection as above for foci (Table 2). The c-MYC-transduced cells exhibited loss of contact inhibition and dense growth in 89% of colonies. The GKLF-transduced cells exhibited a transformed morphology in 44% of colonies. In comparison, a previous study showed that 70% and 40% of NIH3T3 colonies transduced by viruses carrying RAS and RAF exhibited a transformed morphology (Whitehead et al., 1995). Virus supernatants were likewise tested for transformation of NIH3T3 cells. Neither c-MYC nor GKLF induced morphological transformation of NIH3T3 colonies, as previously described for GLI and others (Ruppert et al., 1991). These results identify the RK3E assay as not only highly specific, but also sensitive to the activity of a select group of oncogenes.

In lieu of sequencing the c-MYC alleles, that wild-type c-MYC can transform RK3E cells was confirmed. A human wild-type expression vector (pSRαMSV c-MYC tk-neo) induced foci using direct plasmid transfection of RK3E cells in multiple experiments. Foci were observed at a similar frequency using known wild-type or new c-MYC isolates when analyzed in parallel. In addition, retrovirus encoding the estrogen receptor-c-MYC (wild-type) fusion protein induced morphological transformation of RK3E cells in the presence or absence of 4-hydroxy-tamoxifen. No effect was observed for controls (empty vector or a control containing a deletion in c-MYC residues 106-143).

Figures 3A, 3B, 3C:
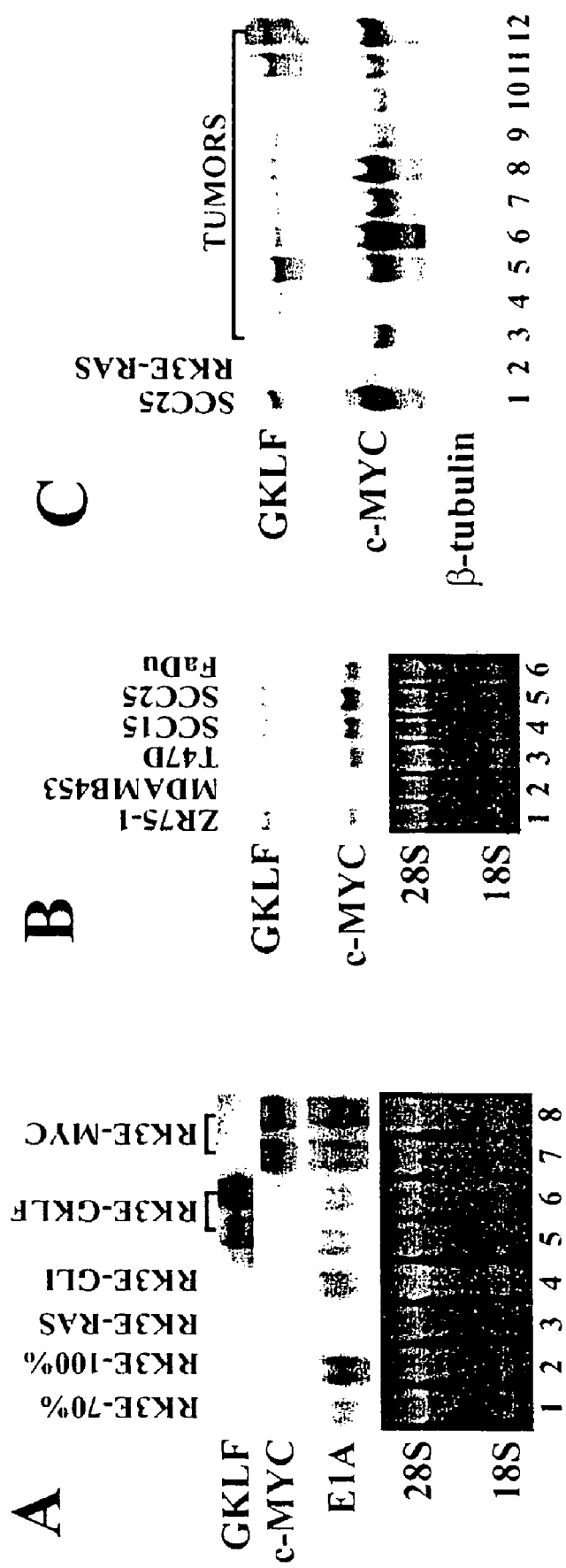
FIGS. 3A-C show Northern blot analysis of c-MYC and GKLF expression. Twenty five μg of total RNA was loaded for each sample.

Northern blot analysis of transformed RK3E cell lines demonstrated expression of the c-MYC and GKLF vector-derived transcripts (FIG. 3A). No endogenous transcripts were detected at the stringency used in this experiment. Compared with RK3E cells at subconfluence (lane 1) or confluence (lane 2), no consistent increase of E1A transcripts was detected in cells transformed by RAS, GLI, c-MYC, or GKLF, suggesting that these genes act upon cellular targets to induce transformation.

To detect the endogenous rat GKLF transcript, reduced-stringency wash conditions and a SmaI fragment from the coding region exclusive of the C-terminal zinc fingers and with no sequence similarity to other genes in the database were used. By this approach, the apparent GKLF transcript was identified and migrated at 3.1 kb, similar to the human 3.0 kb transcript, in RK3E and all derivative transformed cell lines. A single transcript with the same mobility was detected by hybridization of the filter to full-length coding region probe. These studies revealed similar GKLF expression, in RK3E and in derivatives transformed by RAS, GLI, or c-MYC. The results show that GKLF mRNA expression is not significantly altered by these other oncogenes, and is consistent with function of GKLF in an independent pathway.

Cell lines derived from foci induced by c-MYC or GKLF were further tested for tumorigenicity in athymic mice by subcutaneous inoculation at four sites for each line (Table 3).

Tumors were >1 cm in diameter and were scored at 2-4 weeks post-inoculation. Cells transformed by c-MYC induced tumors in 75% or 100% of sites injected (two lines tested). Three lines transformed by GKLF each induced tumors in 50-75% of sites injected. No tumors resulted from injection of RK3E cells, while a GLI-transformed cell line induced tumors in each of the four sites injected. In all, GKLF cell lines induced tumors in 8/12 injection sites, compared with 7/8 for c-MYC and 4/4 for GLI. GKLF-induced tumors also grew more slowly in vivo, reaching 1 cm in diameter by 3.4 weeks, on average, compared with 2.6 weeks for c-MYC and 3 weeks for GLI. The moderately increased latency and decreased efficiency of tumor formation for GKLF cell lines may be attributable to the intrinsic rate of proliferation for these cells (Table 3). While c-MYC, GLI, and GMLF cell lines all exhibited prolonged doubling times in vitro compared with RK3E cells, GKLF cells divided more slowly than the other transformed cell lines.

TABLE 2

Retroviral Transduction of Reconstituted GKLF And c-MYC Expression Vectors

| Plasmid | Focus assay (#foci/10 cm dish)[c] | Colony morphology assay (# transformed/total)[d] |
|---|---|---|
| pCTV3K (vector) | 0, 0 | 0/184 |
| pCTV3K-SQC1[a] (c-MYC) | 0, 0 | 0/232 |
| pCTV3K-SQC5 (c-MYC) | >1000, >1000 | ND |
| pCTV3K-BR1 (c-MYC) | >1000, >1000 | 81/91 (89%) |
| pCTV3K-SQC7 (GKLF) | >1000, >1000 | 91/206 (44%) |
| pCTV3K-SQC11-2[b] (GKLF) | >1000, >1000 | ND |
| pCTV3K-SQC11-3 (GKLF) | >1000, >1000 | ND |

[a]pCTV3K-SQC1 is a c-MYC allele obtained by PCR that exhibited greatly reduced transforming activity compared with other alleles.
[b]SQC11-2 and -3 are independent plasmid clones derived from the same PCR reaction (FIG. 2A, lane 12).
[c]RK3E cells transduced with 4 mls of virus supernatant after calcium phosphate-mediated plasmid transfection of virus packaging cells.
[d]RK3E cells transduced with 0.4 mls of thawed viral supernatant. Cells split 1:4 into selective media 30 hours later. At 2 weeks, drug-resistant colonies were fixed, stained, and examined visually for morphological transformation. Numbers indicate colonies per 10 cm dish. A duplicate transduction experiment yielded similar results. No colonies formed in control dishes that were not exposed to virus.
ND, not determined.

TABLE 3

Tumorigenicity of RK3E-Derived Cell Lines In Athymic Mice

| Cell Line | #Tumors/#Sites Injected | Tumor Latency in vivo (weeks)[c] | Doubling Time in vitro (hrs) |
|---|---|---|---|
| RK3E | 0/4 | — | 12.7 |
| RK3E-c-MYC BR1[a] | 3/4 | 3, 3, 4 | 19.1 |
| RK3E-c-MYC B[b] | 4/4 | 2, 2, 2, 2 | 19.8 |
| RK3E-GKLF E | 3/4 | 3, 3, 3 | 33.7 |
| RK3E-GKLF F | 2/4 | 4, 4 | 27.0 |
| RK3E-GKLF G | 3/4 | 3, 3, 4 | ND |
| RK3E-GLI | 4/4 | 3, 3, 3, 3 | 18.0 |

[a]Cell line derived from a focus identified in the original screen using a breast cancer cDNA library.
[b]Cell line derived by transformation with the reconstituted plasmid pCTV3K-BR1.
[c]The time required for tumors to reach 1 cm. in diameter is indicated.
ND—not determined

EXAMPLE 5

Northern Blot Analysis of GKLF/KFL4 Expression in Tumors and Tumor-Derived Cell Lines Tumor samples were obtained through the Tissue Procurement Facility of the UAB Comprehensive Cancer Center and the Southern Division of the Cooperative Human Tissue Network. Microdissection was used to isolate tissue composed of >70% tumor cells. Total RNA was isolated as described (Chomczynski et al., 1987), then denatured and separated on a 1.5% formaldehyde agarose gel and transferred to nitrocellulose (Schleicher & Schuell, Keene, N.H.). Prehybridization was at 42° C. for 3 hours in 50% formamide, 4×SSC (SSC is 150 mM NaCl, 15 mM sodium citrate, pH 7.5), 0.1 M sodium phosphate (pH 6.8), 0.1% sodium pyrophosphate, 0.1% SDS, 5×Denhardt's and 25 µg/ml denatured salmon sperm DNA. Hybridization was at 42° C. for 16-20 hrs. The hybridization mixture contained 45% formamide, 4×SSC, 0.1 M sodium phosphate (pH 6.8), 0.075% sodium pyrophosphate, 0.1% SDS, 10% dextran sulfate and 100 µg/ml denatured salmon sperm DNA. Following hybridization, the filter was washed twice in 2×SSC, 0.1% SDS for 20 minutes at room temperature, then washed in 0.3×SSC, 0.3% SDS for 30 min at 59° C. (for detection of rat transcripts) or 65° C. For stripping of hybridized probes, the filter was placed in a solution of 2×SSC, 25 mM Tris-HCl (pH 7.5), 0.1% SDS at initial temperature of 95° C., and shaken for 10 min at room temperature.

Results of Northern blot analysis were shown in FIGS. 3B and 3C. GKLF expression in breast or squamous cell carcinoma cell lines was variable, with increased expression in the breast tumor line ZR75-1 and the squamous cell lines SCC15 and SCC25 (FIG. 3B). In human squamous cell carcinomas microdissected to enrich for tumor cells, GKLF expression was detected in each of ten primary or metastatic tumors analyzed, with expression levels comparable to that for the cell line SCC25 (FIG. 3C). The results suggest that GKLF represents a potent transforming activity that is consistently expressed in tumors as well as in tumor-derived cell lines. As GKLF was isolated from cell lines that express the gene at a level found in tumors in vivo, the results suggest that GKLF may represent a major transforming activity in tumors as well as in cell lines.

EXAMPLE 6

Figure 4A:
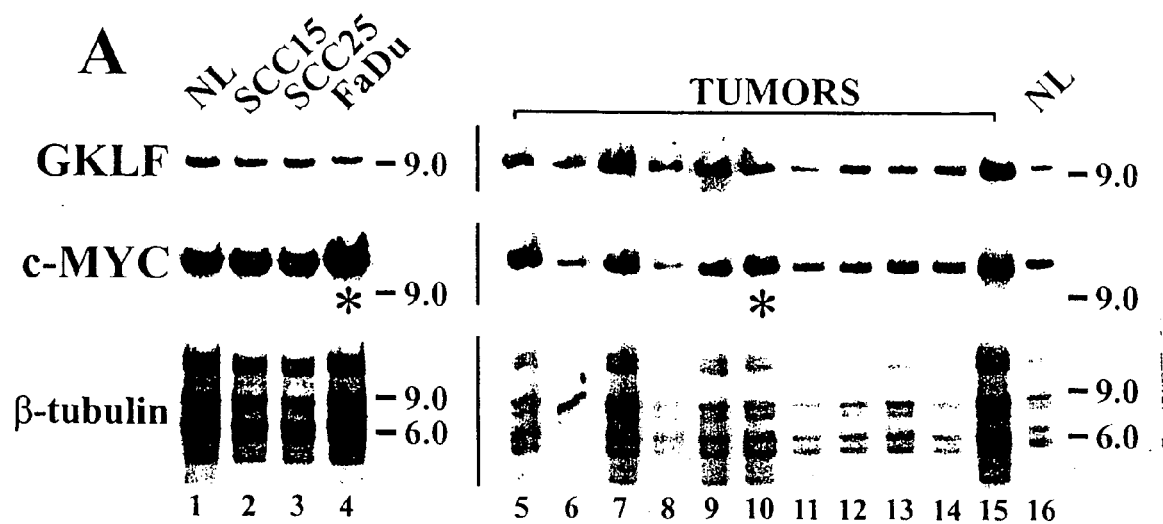
FIGS. 4A-B show Southern blot analysis of cell line- and tumor-derived genomic DNA. Five μg of DNA was digested with EcoRI and separated by gel electrophoresis. The filters were hybridized sequentially to GKLF, c-MYC, and β-tubulin probes. Asterisks indicate samples with increased apparent copy number of c-MYC. Molecular weight markers are indicated on the right. NL, normal human lymphocyte DNA.
Figure 4B:
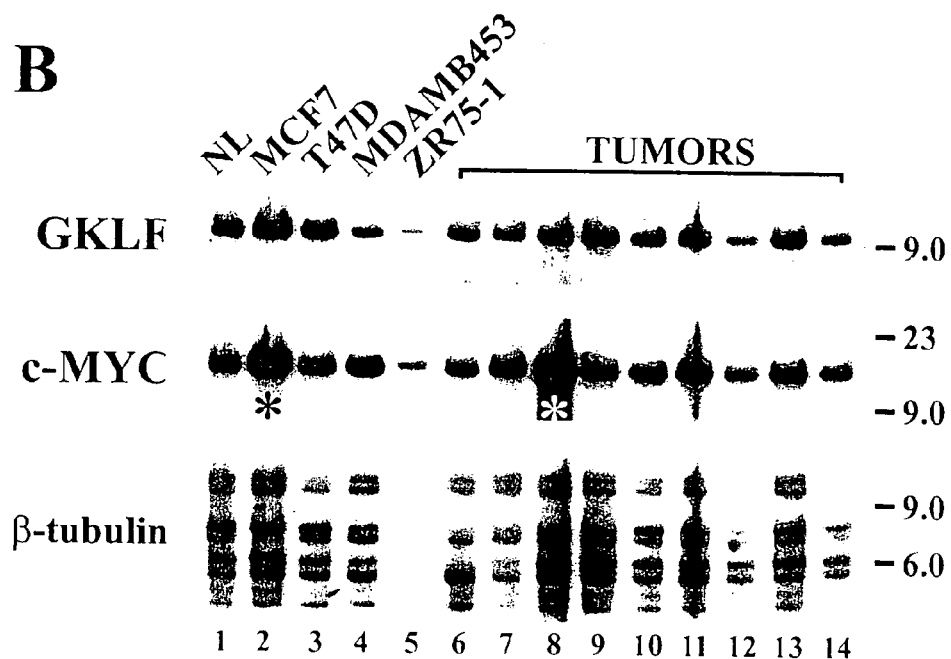
Figure 5A:
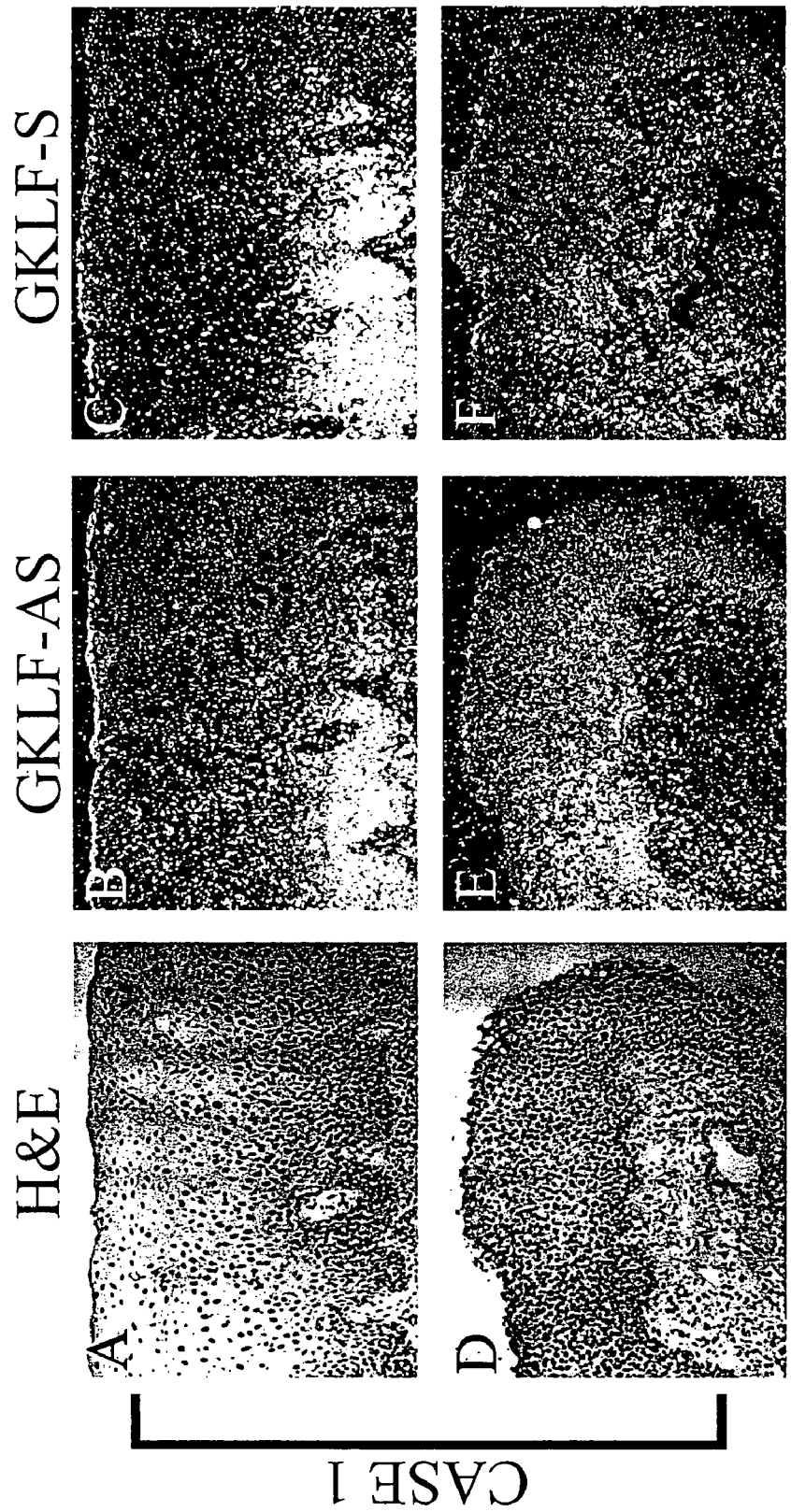
FIGS. 5A-B show in situ hybridization analysis of GKLF. Paraffin-embedded (A-L) or fresh-frozen (M-O) tissues were analyzed using antisense (GKLF-AS) or sense (GKLF-S) $^{35}$S-labelled RNA probes. Each image (A-O) is 650 μm×530 μm. Sections were stained with Hematoxylin and Eosin (H&E). Case 1, A-C: uninvolved epithelium in a patient with primary laryngeal squamous cell carcinoma; D-F: adjacent dysplastic epithelium within the same tissue block. Case 2, G-I: uninvolved epithelium; J-L: adjacent primary tumor nests within stroma in the same tissue block; asterisk indicates a salivary gland and ducts. Case 3, M-O: metastatic laryngeal squamous cell carcinoma infiltrating a lymph node; asterisk indicates lymphocytes.
Figure 5B:
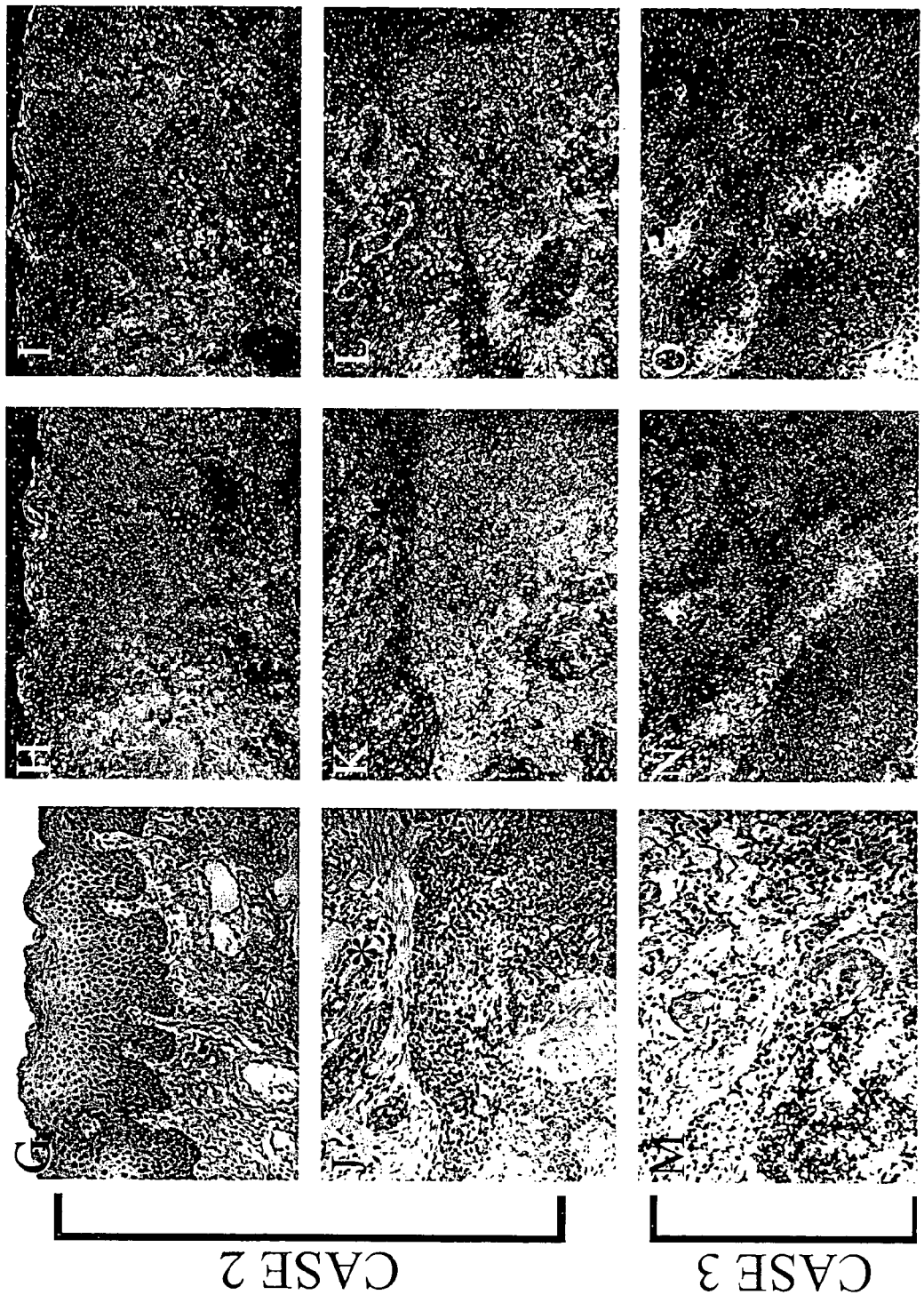

Gene Copy Number of c-MYC and GKLF/KFL4 in Tumor Cells c-MYC has been shown to be activated by gene amplification in ~10% of oral squamous cancers, and may be activated in these or other tumors by genetic alteration of VNT-APC-_-catenin pathway components. To determine whether expression of GKLF in cell lines and tumors is likewise associated with gene amplification, southern blot analysis (FIGS. 4A and 4B) was performed. Filters were sequentially hybridized to GKLF, c-MYC and β-tubulin. Increased copies of c-MYC were identified in two cell lines used for library construction, FaDu and MCF7. Increased hybridization to c-MYC was likewise observed for one of eleven oral squamous cell carcinomas (FIG. 4A, lane 10) and for one of nine breast carcinomas (FIG. 4B, lane 8). These results are consistent with the published frequencies of c-MYC amplification for these tumor types. No copy number gains of GKLF were observed, indicating that other mechanisms may contribute to expression of GKLF in tumors. The same may be true for c-MYC, as gene amplification in FaDu cells was associated with reduced expression compared with other oral cancer cell lines (FIG. 3B).

EXAMPLE 7

GKLF/KFL4 Expression is Activated Early During Tumor Progression in Vivo

Previously, expression of c-MYC was found to be up-regulated consistently in dysplastic oral mucosa and in squamous cell carcinomas, and tumors with the highest levels of c-MYC expression were associated with the poorest clinical outcome. To determine how GKLF mRNA expression is altered during tumor progression, squamous cell carcinoma of the larynx and adjacent uninvolved epithelium from the same tissue blocks were analyzed using $^{35}$S-labelled riboprobes by in situ hybridization analysis.

In situ hybridization was conducted as described (Cheng et al., 1995), using sense and antisense $^{35}$S-labelled riboprobes generated from a 301 base pair EcoRI fragment derived from the GKLF 3' UTR positioned 40 bases from the stop codon. A GAPDH antisense probe corresponding to bases 366-680 (Accession M33197) was synthesized using a commercially available template (Ambion, Inc., Austin, Tex.). All results were obtained in duplicate. High stringency washes were in 0.1×SSC and 0.1% (v/v) 2-mercaptoethanol at 58° C. for GKLF or 68° C. for GAPDH. Slides were coated with emulsion and exposed for 14 days.

In apparently normal epithelium, GKLF expression was detected in the spinous layer above the basal and parabasal cells (9 specimens analyzed) (FIGS. 5A-C, 5G-I; Table 4). No specific GKLF expression was detected in the basal or parabasal cells or in the underlying dermis. In contrast, a sense control probe produced grains at a much-reduced frequency in a uniform fashion across the epithelium. GAPDH expression served as a positive control, and was detected diffusely throughout the entire epithelium. The pattern of GKLF expression is identical to the pattern in normal mouse skin.

For each of 12 specimens analyzed, dysplastic epithelium exhibited increased GKLF expression throughout the epithelium (FIGS. 5D-F; Table 4, cases 1, 2, 4, 9, 11, 12, 15-17). In contrast to results obtained in normal-appearing epithelium, there was no reduction of expression in the basal and parabasal layers compared with superficial layers. For tissue sections that contained both uninvolved epithelium and adjacent dysplastic epithelium, the overall level of GKLF expression in dysplastic epithelium was prominently elevated compared with the GKLF-positive cell layers in uninvolved epithelium (FIGS. 5B, 5E, and 5H; Table 4, cases 1, 2, 4, 11, 12, and 16). These results suggest that GKLF expression is qualitatively and quantitatively altered in dysplasia, that exclusion of GKLF from the basal and parabasal cell layers is lost early during neoplastic progression, and that GKLF exhibits properties of an oncogene not only in vitro but also in vivo.

As shown by northern blot analysis, GKLF transcripts are consistently present in tumor-derived mRNA (FIG. 3C, Table 4). To determine whether GKLF is expressed in tumor cells, laryngeal squamous cell carcinomas was examined by mRNA in situ hybridization. Expression was detected in each primary (13 cases) or metastatic (5 cases) tumor examined (FIGS. 5J-O; Table 4), with all or nearly all tumor cells associated with silver grains. The level of expression was somewhat heterogeneous, with higher levels found in the periphery and in nodules of tumor containing centrally necrotic cells or keratin pearls. As for dysplastic epithelium, expression in tumor cells was consistently elevated compared with uninvolved epithelium in the same sections (FIGS. 5H and 5K; Table 4, cases 1, 2, 11, 12, 16). However, expression in tumor cells was not higher than in dysplastic epithelium (cases 1, 9, 11, 12, 15-17). For several cases expression in the most dysplastic epithelium was higher than in adjacent GKLF-positive tumor, suggesting that GKLF expression is specifically activated during the transition from normal epithelium to dysplasia, prior to invasion or metastasis.

TABLE 4

Expression of GKLF/KFL4 in oral epithelium and tumors

| Case[a] | Histopathology (U, D, P, M)[b] | Tissue Source (PE/FF)[c] | Method (N/ISH)[d] | GKLF expression[e] |
|---|---|---|---|---|
| 1 | U, D, P | PE | ISH | D, P > U |
| 2 | U, D | PE | ISH | D > U |
| 2 | U, P | PE | ISH | P > U |
| 3 | M | FF | ISH | + |
| 4 | U, D | PE | ISH | D > U |
| 5 | P | FF | N, ISH | + |
| 6 | M | FF | N, ISH | + |
| 7 | P | FF | ISH | + |
| 8 | P | FF | N, ISH | + |
| 9 | D, P | PE | ISH | D, P+ |
| 10 | M | PE | ISH | + |
| 11 | U, D, P | PE | ISH | D, P > U |
| 12 | U, D | PE | ISH | D > U |
| 12 | U, D, P | PE | ISH | D, P > U |
| 13 | U | PE | ISH | + |
| 13 | P | PE | ISH | + |
| 14 | P | PE | ISH | + |
| 14 | M | PE | ISH | + |
| 15 | D | PE | ISH | + |
| 15 | D | PE | ISH | + |
| 15 | D, P | PE | ISH | D, P+ |

TABLE 4-continued

Expression of GKLF/KFL4 in oral epithelium and tumors

| Case[a] | Histopathology (U, D, P, M)[b] | Tissue Source (PE/FF)[c] | Method (N/ISH)[d] | GKLF expression[e] |
|---|---|---|---|---|
| 16 | U, D, P | PE | ISH | D, P > U |
| 16 | M | PE | ISH | + |
| 17 | D, P | PE | ISH | D, P+ |
| 18 | P | FF | N | + |
| 19 | P | FF | N | + |
| 20 | M | FF | N | + |
| 21 | P | FF | N | + |
| 22 | M | FF | N | + |
| 23 | M | FF | N | + |
| 24 | P | FF | N | + |

[a]Each row corresponds to a tissue specimen. Levels of gene expression indicate changes identified within, rather than between, single tissue sections. For some cases multiple specimens isolated during the same surgical procedure were analyzed. ISH results were confirmed by analysis of sections in duplicate.
[b]U, uninvolved or normal-appearing epithelium; D, dysplastic epithelium; P, primary tumor; M, metastatic tumor.
[c]PE, paraffin-embedded; FF, fresh-frozen.
[d]N, Northern; ISH, mRNA in situ hybridization.
[e]D, P > U indicates increased expression in dysplasia and primary tumor compared with uninvolved epithelium in the same section. D, P+ indicates expression in both dysplasia and adjacent primary tumor.

EXAMPLE 8

Identification of Transforming Oncogenes in Oral Cancer

A cDNA expression library was prepared using mRNA from human oral cancer cell lines. Using retroviral transduction, 4 million independent cDNAs were stably expressed in RK3E cells. Fourteen foci were identified. Single human cDNAs were identified in each of the clones using long PCR. Twelve of these were c-MYC alleles truncated in the 5' untranslated region. Two were independent, full-length, wild type alleles of a novel oncogene, SCC7, encoding a poorly characterized putative transcription factor not previously implicated in transformation. Expression vectors reconstituted using c-MYC or SCC7 PCR products induced hundreds of foci per dish. By Northern analysis, high level expression of SCC7 was observed in oral and breast cancel cell lines (5/6 tested). Expression of the endogenous rat SCC7 mRNA was upregulated in transformed rat kidney cells compared with immortalized parental cells. Cells transformed by c-MYC and SCC7 exhibited expression of the respective vector-derived mRNA and were tumorigenic in athymic mice. Expression of E1a was not altered by any of the oncogenes. These results demonstrate that known and novel oncogenes can be rapidly identified in a specific fashion using epithelial-like host cells, and show that SCC7, c-MYC, RAS, and GLI can each transform cells in cooperation with adenovirus E1a in vitro. By analogy with c-MYC, RAS and GLI, activation of SCC7 may likewise contribute to tumor progression in vivo.

EXAMPLE 9

GKLF/KFL4 mRNA Expression is Upregulated During Breast Tumor Progression

Previously, SAGE analysis of purified normal breast epithelial cells detected GKLF transcripts at an abundance of 40 tags per million. In the present study, Northern blot analysis of breast tumor cell lines revealed the presence of GKLF transcripts. Using sense and antisense [35S]-labeled riboprobes, the expression of GKLF mRNA was examined in 31 cases of carcinoma of the breast. Specificity of hybridization was determined by using the sense probe as a negative control or by hybridization of the antisense probe to human foreskin, in which GKLF was specifically detected in suprabasal epithelial cells (not shown).

Figure 6A:
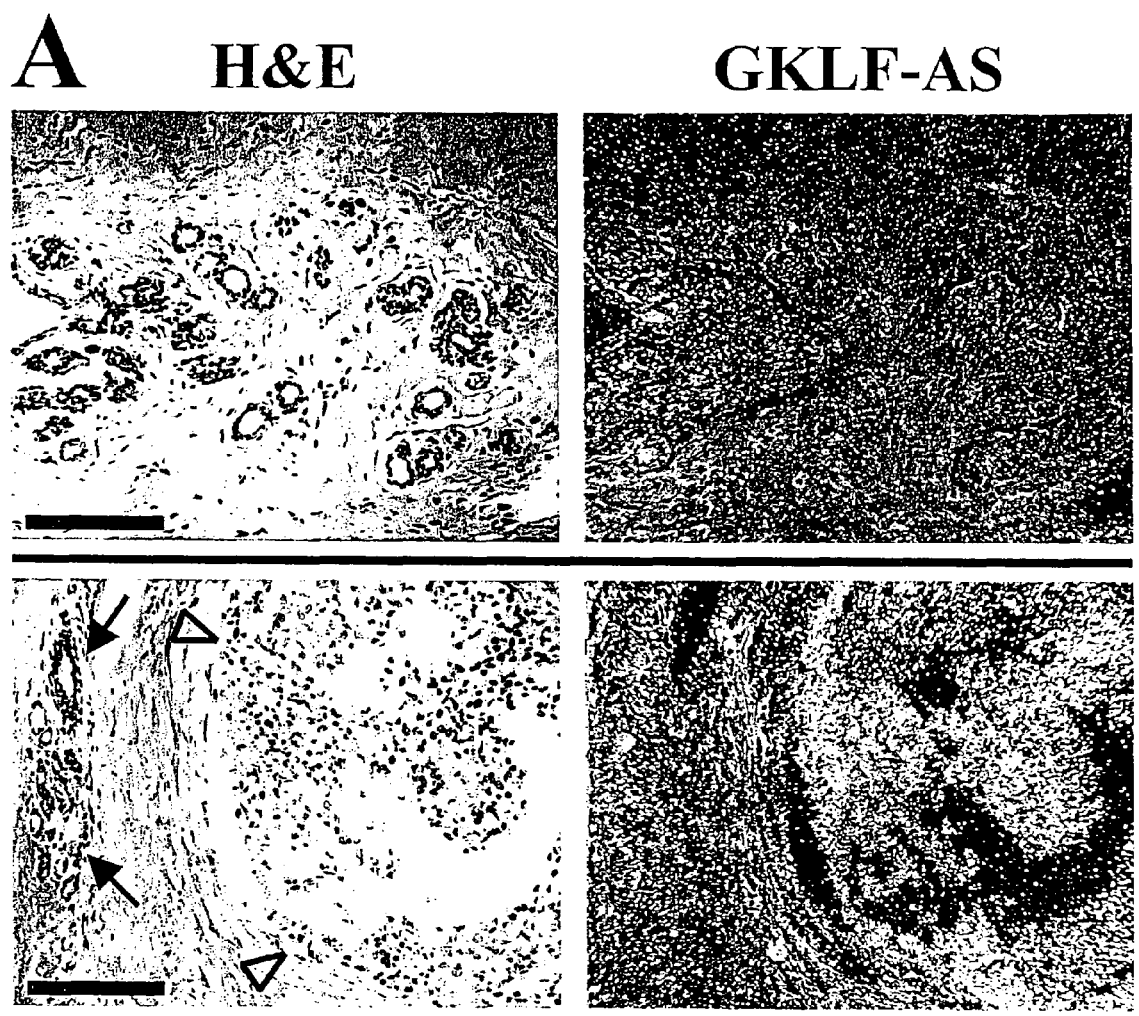
FIGS. 6A-B show in situ hybridization analysis of GKLF mRNA in carcinoma of the breast. Two distinct cases were analyzed by applying an antisense (GKLF-AS) [$^{35}$S]-labeled RNA probe to sections of parraffin-embedded (A) or fresh-frozen (B) surgical material. Brightfield (left) and darkfield (right) views are shown. Sections were stained with hematoxylin and eosin (H&E). Two areas of the same slide are shown in FIG. 6A, with uninvolved (i.e., morphologically normal) breast epithelium (upper plate) adjacent to an area (lower plate) containing DCIS (arrowheads) and additional uninvolved tissue (arrows).
Figure 6B:
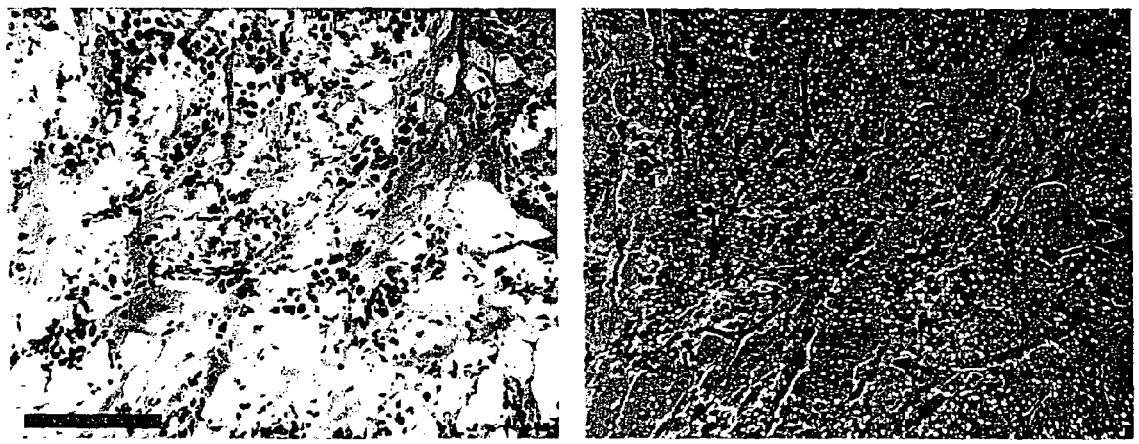

Expression of GKLF was detected in malignant cells in 21 of 31 cases of ductal adenocarcinoma (68%, FIG. 6, Table 5). For several cases that exhibited no detectable expression of GKLF, prominent expression of the housekeeping gene GAPDH was observed, indicating that overall mRNA integrity was maintained and that failure to identify GKLF transcripts may reflect reduced levels of expression. GKLF expression was increased in malignant cells of 14 of 19 cases that contained adjacent uninvolved epithelium (FIG. 6A). For 7 of these 14 cases, no specific signal was detected in adjacent uninvolved epithelium. In the other 7 cases, expression was detected in both uninvolved and malignant cells, with expression of GKLF in malignant cells increased by 3-5 fold compared with uninvolved epithelium. Within tumors, expression of GKLF was specific to malignant cells, with little or no expression detected in stromal components (FIG. 6B).

Figure 7:
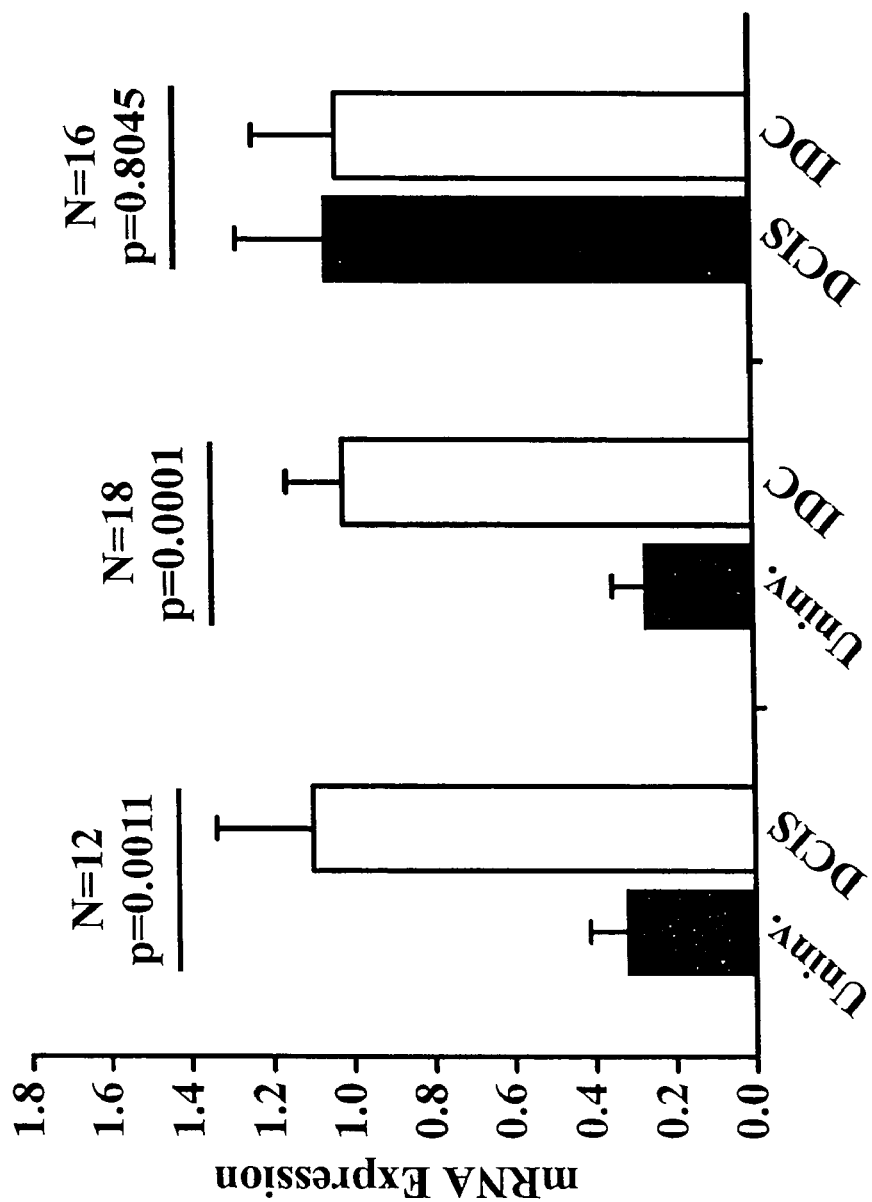
FIG. 7 shows GKLF mRNA expression in normal and neoplastic breast tissue. The data in Table 5 was analyzed using a paired t-test. Sample size (N), statistical significance (p), and standard error of the mean are indicated for each comparison. Uninv, uninvolved ducts; DCIS, ductal carcinoma in situ; IDC, invasive ductal carcinoma.

GKLF expression in DCIS was not significantly different from invasive carcinoma, but expression in both lesions was higher than for uninvolved breast epithelium (Table 5, FIG. 7). In contrast to results obtained in breast tumors, examination of several cases of prostatic carcinoma revealed equal or reduced expression in tumor cells compared with adjacent uninvolved glandular epithelial cells (Table 5). In summary, the results suggest that GKLF mRNA expression is activated in approximately two-thirds of breast carcinomas, and that expression in positive cases is consistently induced in DCIS prior to invasion.

TABLE 5 mRNA in situ Hybridization Analysis of GKLF/KFL4 In Tumors[a]

| | | Carcinoma of the Breast | | | | |
|---|---|---|---|---|---|---|
| | | GKLF-AS | | | | |
| CASE | PE/FF | U | D | T | GKLF-S | GAPDH-AS |
| 1 | FF | 0.5 | 2.5 | — | 0.0 | + |
| 2 | FF | — | — | 2.0 | 0.0 | + |
| 3 | FF | 0.0 | — | 1.0 | 0.0 | + |
| 4 | FF | — | — | 0.0 | 0.0 | + |
| 5 | FF | — | — | 0.0 | 0.0 | NT |
| 6 | FF | — | — | 0.0 | 0.0 | NT |
| 7 | FF | — | 2.0 | 2.0 | 0.0 | NT |
| 8 | FF | 0.0 | 1.0 | 1.0 | 0.0 | NT |
| 9 | FF | — | — | 0.0 | 0.0 | NT |
| 10 | FF | — | — | 0.0 | 0.0 | NT |
| 11 | FF | — | — | 0.0 | 0.0 | NT |
| 12 | FF | — | — | 0.5 | 0.0 | NT |
| 13 | FF | 0.0 | — | 0.5 | 0.0 | NT |
| 14 | FF | — | — | 0.5 | 0.0 | NT |
| 15 | PE | — | — | 1.5 | NT | + |
| 16 | PE | 0.0 | — | 1.0 | NT | + |
| 17 | PE | 0.0 | — | 1.0 | NT | + |
| 18 | PE | 0.0 | — | 2.0 | NT | + |
| 19 | PE | — | — | 0.0 | NT | + |

TABLE 5-continued mRNA in situ Hybridization Analysis of GKLF/KFL4 In Tumors[a]

| 20 | PE | 1.0 | 2.0 | 1.0 | NT  | +   |
|----|----|----|----|----|-----|-----|
| 21 | PE | 0.5 | —  | 1.5 | NT  | +   |
| 22 | PE | 0.5 | 2.0 | 2.0 | NT  | +   |
| 23 | PE | 1.0 | —  | 1.0 | 0.0 | +   |
| 24 | PE | 0.5 | 1.0 | 1.2 | 0.0 | +   |
| 25 | PE | 0.3 | 1.2 | 1.2 | 0.0 | +   |
| 26 | PE | 0.5 | 1.5 | 1.5 | 0.0 | +   |
| 27 | PE | 0.0 | 0.0 | 0.0 | 0.0 | +   |
| 28 | PE | 0.0 | 0.0 | 0.0 | 0.0 | +   |
| 29 | PE | 0.0 | 0.0 | 0.0 | 0.0 | +   |
| 30 | PE | 0.5 | 1.0 | 1.0 | 0.0 | +   |
| 31 | PE | 0.0 | 1.0 | 1.5 | 0.0 | 0.0 |

Carcinoma of the Prostate

GKLF-AS

| CASE | PE/FF | U | PIN | T | GKLF-S | GAPDH-AS |
|------|-------|---|-----|---|--------|----------|
| 1 | PE | 1.0 | — | 0.0 | NT | + |
| 2 | PE | — | — | 0.0 | NT | + |
| 3 | PE | 1.0 | — | 1.0 | NT | + |
| 4 | PE | 1.0 | 1.0 | 0.0 | NT | 0.0 |

[a]Results obtained for sense (S) or antisense (AS) probes are presented.
Scoring of GKLF used a scale of 0.0 to 4.0, whereas GAPDH was scored as detected (+) or undetected (0.0).
Numbers indicate the level of gene expression for histologically distinct tissue within the same section.
A dash (—) indicates that no tissue in the section exhibited the specific histopathologic feature.
PE, paraffin-embedded;
FF, fresh-frozen;
U, uninvolved or morphologically normal epithelium;
D, ductal carcinoma in situ;
PIN, prostatic intraepithelial neoplasia;
T, invasive tumor cells;
NT, not tested.

EXAMPLE 10

Characterization of a GKLF/KFL4-Specific Monoclonal Antibody

The region of the human GKLF cDNA encoding residues 479-1197 (accession AF105036) was cloned into plasmid pET-32a-ZFP4 and expressed in E. coli BL21(DE3) bacteria as a His-tagged protein. Protein was purified from the bacteria after induction with IPTG using a His-Trap Ni-agarose column (Amersham Pharmacia Biotech, Piscataway, N.J.) and eluted with 500 mM imidazole. Purified protein was used to immunize two mice, and lymphocytes were fused with murine myeloma cells (PX63-Ag8.653). Hybridomas that were immunoreactive in an ELISA assay for the purified antigen were cloned and recloned by limiting dilution. Positive clones were identified by ELISA, and an $IgG_1$ antibody was purified from ascites on a protein A affinity column.

The $IgG_1$ isotype antibody raised against bacterially-expressed GKLF was subsequently referred to as anti-GKLF (αGKLF). Immunoblot analysis of GKLF-transformed RK3E cells and control cell lines detected a single protein species of 55 kDa, consistent with the predicted size of the full-length polypeptide (data not shown). Compared with RK3E cells or control cell lines transformed by other oncogenes, apparent GKLF abundance was increased by several-fold in each of two cell lines transformed by the human expression vector. The epitope recognized by the antibody may be denaturation sensitive, as a signal was obtained only after overnight exposure of autoradiographic film using a standard chemiluminescence protocol. The antibody was not sufficiently sensitive to detect GKLF by immunoblot analysis of extracts of human tumor cell lines that express the endogenous GKLF mRNA.

The cell type- and tumor type-specific patterns of GKLF mRNA expression were utilized to examine the specificity of αGKLF in immunohistochemical assays. These patterns can be summarized as follows. Human GKLF mRNA is detected by in situ hybridization in differentiating cells of oral epithelium, and is markedly elevated in oral tumors. The mRNA is not detected in morphologically normal basal or parabasal cells, particularly within epidermal pegs that extend further into the submucosa. Mouse GKLF mRNA is similarly found to be more highly expressed in superficial, differentiating cells of the skin and gut, and is reduced or absent in basal epithelial cells in both tissues. In contrast to human oral and breast cancer, GKLF mRNA expression is reduced in mouse colorectal tumors compared with normal epithelium, and is similarly reduced in human colorectal cancer as indicated by SAGE.

For immunohistochemical staining, tissues were fixed in neutral buffered formalin and embedded in paraffin. Deparaffinized tissue sections were incubated with αGKLF at a concentration of 1.0 μg/ml for 1 hr at room temperature, and processed as described (Grizzle, et al., 1998a). Immunodetection was performed using a biotinylated secondary antibody, streptavidin-horseradish peroxidase detection system (Signet Laboratories, Dedham, Mass.), and the chromogenic substrate diaminobenzidine (Biogenex, San Ramon, Calif.). Sections were counterstained with hematoxylin. Results were scored by using a 0.0 to 4.0 scoring system, wherein 4.0 corresponds to a saturated signal (Grizzle, et al., 1998b).

Figure 8A:
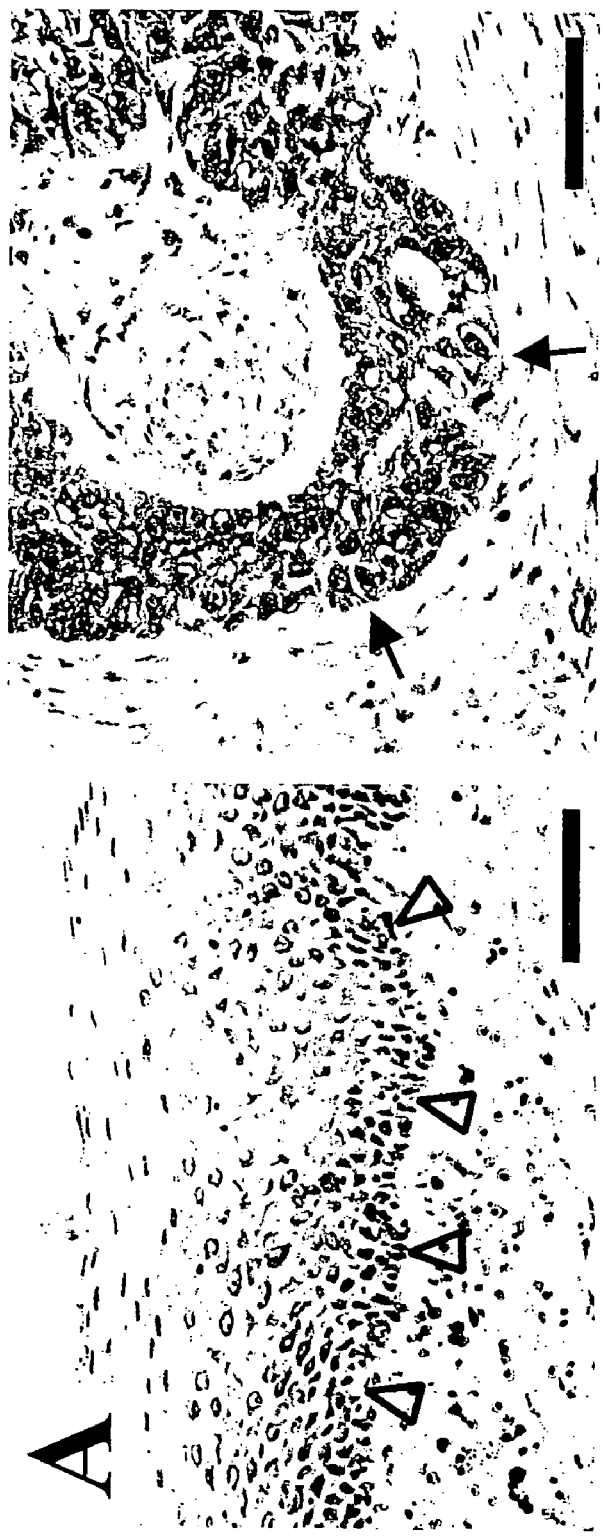
FIGS. 8A-C show immunostaining of human tissues with αGKLF monoclonal antibody. Each panel (FIG. 8A-C) illustrates adjacent areas of a tissue section.
Figure 8B:
Figure 8C:
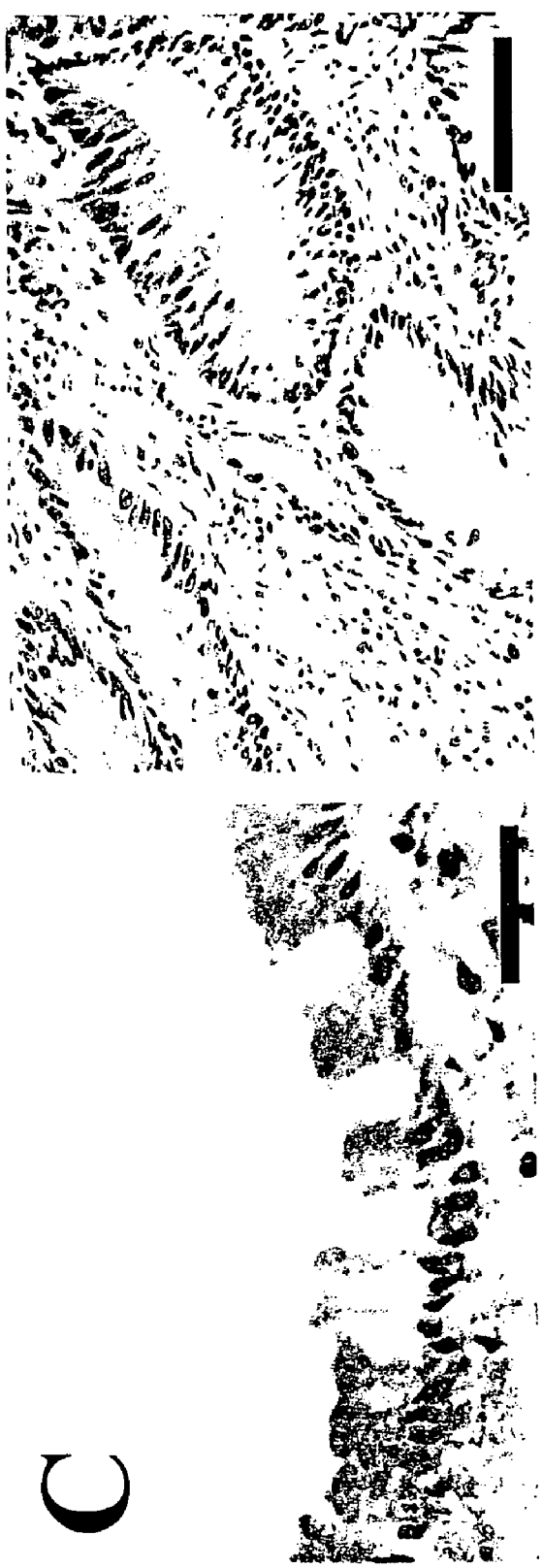
Figure 9A:
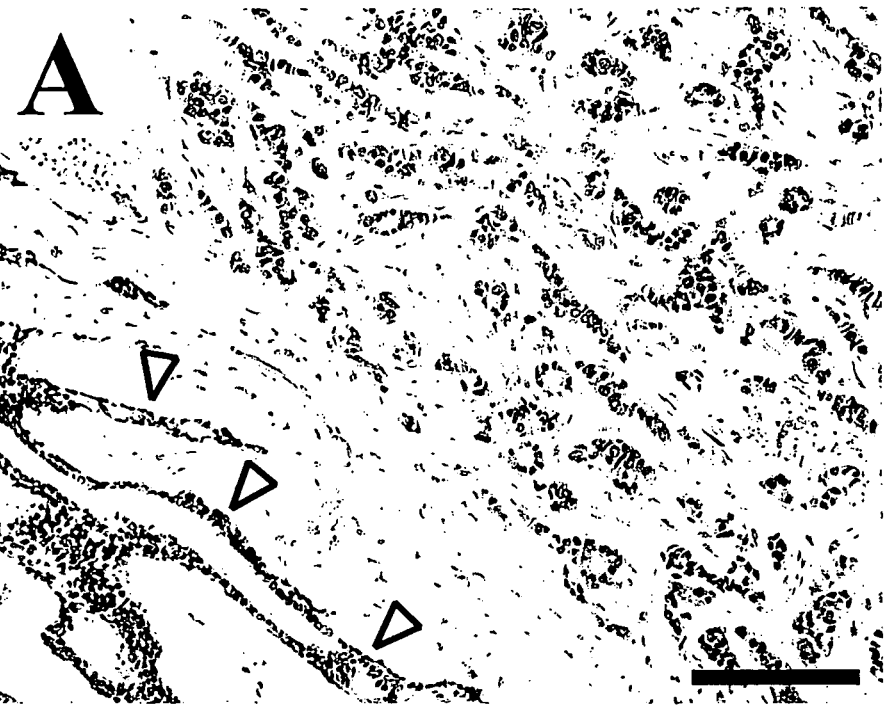
FIGS. 9A-C show immunostaining of breast tissue with αGKLF.
Figure 9B:
Figure 9C:
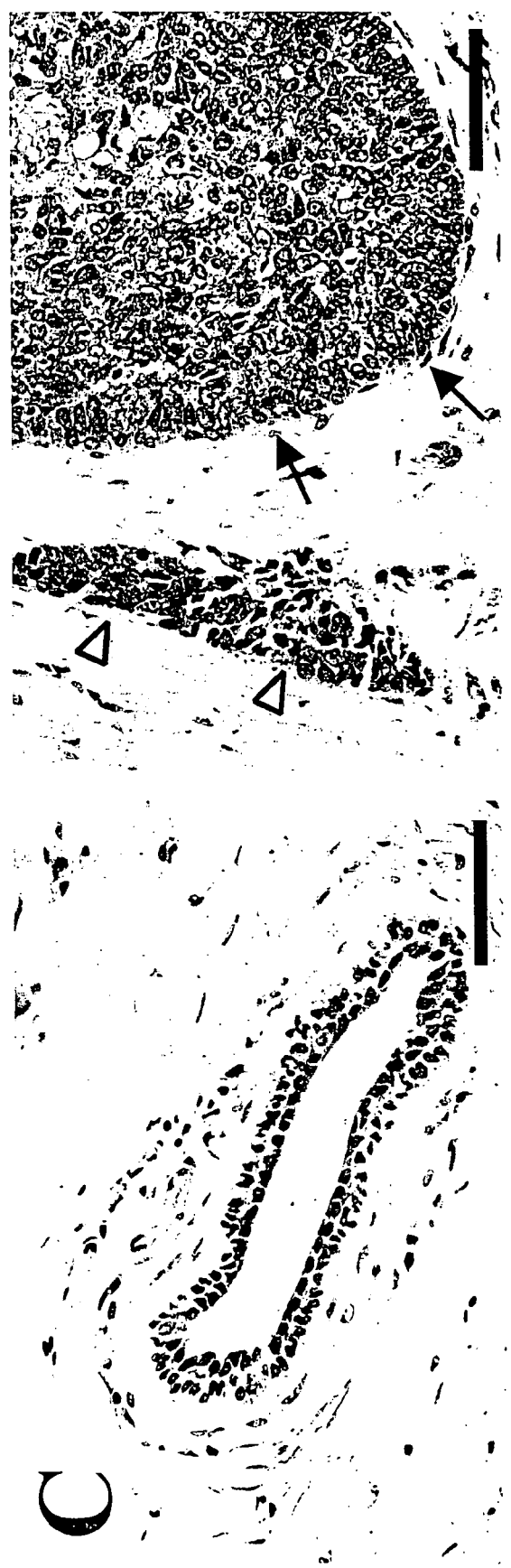

The staining pattern of αGKLF exhibited a strict concordance with detection of GKLF mRNA (FIGS. 8-9, Table 6). In positive tissues, αGKLF exhibited a mixed nuclear and cytoplasmic staining pattern. For uninvolved epithelium, DCIS, and invasive carcinoma alike, the average cytoplasmic staining was 1.8-2.5 fold greater than nuclear staining, suggesting that subcellular localization was not altered during tumor progression in any consistent fashion. Cytoplasmic staining was subsequently used as a more sensitive indicator of overall expression.

In several samples of skin or oral squamous epithelium, αGKLF bound specifically to differentiating suprabasal epithelial cells (FIG. 8A). Compared with adjacent uninvolved epithelium, staining was markedly increased in malignant cells for each of several cases of squamous cell carcinoma, with little or no staining of stromal components of the tumor. Likewise, staining was increased in superficial cells compared to cells deeper within epithelial crypts of the small bowel (FIG. 8B) or large bowel (Table 6, P=0.043). In contrast to oral and breast tumors, staining was reduced in tumor cells compared with adjacent superficial epithelial cells for each of four cases of human colorectal adenoma or carcinoma examined (FIG. 8C, Table 6, P=0.027).

TABLE 6

Immunohistochemical Analysis of GKLF/KFL4 In Tumors[a]

| | | Carcinoma of the Breast | | | | | |
|---|---|---|---|---|---|---|---|
| | | Uninvolved | | DCIS | | Invasive tumor cells | |
| CASE | PE/FF | Nucleus | Cytoplasm | Nucleus | Cytoplasm | Nucleus | Cytoplasm |
| 23 | PE | 0.25 | 0.45 | — | — | 0.35 | 0.55 |
| 24 | PE | 0.50 | 1.30 | 1.00 | 1.30 | 1.00 | 1.30 |
| 25 | PE | 0.65 | 0.95 | 0.45 | 1.40 | 0.38 | 1.35 |
| 26 | PE | 0.18 | 0.75 | 0.03 | 1.20 | 0.12 | 1.05 |
| 27 | PE | 0.10 | 1.30 | 0.00 | 1.10 | 0.05 | 0.50 |
| 28 | PE | 0.10 | 0.30 | — | — | 0.35 | 0.20 |
| 29 | PE | 0.00 | 0.00 | 0.10 | 0.75 | 0.05 | 0.75 |
| 30 | PE | 0.00 | 0.20 | 0.10 | 1.05 | — | — |
| 31 | PE | 0.00 | 0.10 | 0.65 | 0.65 | 0.70 | 1.15 |
| 32 | PE | 0.25 | 0.55 | 0.55 | 0.75 | 0.42 | 0.85 |
| 33 | PE | 0.80 | 0.45 | — | — | 0.50 | 1.25 |
| 34 | PE | 0.18 | 0.50 | — | — | 0.45 | 1.15 |
| 35 | PE | 0.30 | 0.35 | 0.60 | 1.60 | 0.65 | 1.50 |
| 36 | PE | 0.00 | 0.05 | 0.55 | 1.70 | 0.75 | 1.00 |
| 37 | PE | 0.70 | 0.60 | — | — | 1.65 | 1.80 |
| 38 | PE | — | — | 0.00 | 0.90 | 0.00 | 1.50 |
| 39 | PE | 0.55 | 0.70 | 0.75 | 0.85 | 1.75 | 1.75 |
| 40 | PE | 0.35 | 0.50 | 0.75 | 0.90 | 0.75 | 0.85 |

| | | Colorectal carcinoma | | | | | |
|---|---|---|---|---|---|---|---|
| | | Normal Superficial[b] | | Normal Deep[c] | | Tumor[d] | |
| CASE | PE/FF | Nucleus | Cytoplasm | Nucleus | Cytoplasm | Nucleus | Cytoplasm |
| 1 | PE | 0.45 | 1.00 | 0.25 | 0.05 | 0.00 | 0.85 |
| 2 | PE | 0.40 | 0.60 | 0.40 | 0.25 | 0.20 | 0.35 |
| 3 | PE | 0.15 | 1.15 | 0.30 | 0.80 | 0.25 | 0.85 |
| 4 | PE | 0.00 | 1.30 | 0.00 | 0.15 | 0.00 | 0.80 |
| 5 | PE | — | — | — | — | 0.00 | 0.65 |

[a]Immunohistochemical scores indicate the intensity of staining of histologically distinct tissue within the same section.
A dash (—) indicates that no tissue in the section exhibited the specific histopathologic feature.
PE, paraffin-embedded;
FF, fresh-frozen;
DCIS, ductal carcinoma in situ.
[b]Differentiating epithelial cells located in the superficial portion of intestinal mucosa.
[c]Epithelial cells deep within intestinal mucosa.
[d]Analysis included both adenomas and adenocarcinomas.

EXAMPLE 11

GKLF/KFL4 In Situ Hybridization in Breast Tumor Cells

In situ hybridization was conducted, using sense and antisense [$^{35}$S]-labeled riboprobes prepared by in vitro transcription of a cDNA fragment corresponding to the 3' untranslated region of human GKLF. A GAPDH antisense probe corresponding to bases 366-680 (Accession M33197) was synthesized using a commercially available template (Ambion, Inc., Austin, Tex.). High stringency washes were in 0.1×SSC and 0.1% (v/v) 2-mercaptoethanol at 58° C. for GKLF or 68° C. for GAPDH. Slides were coated with emulsion and exposed for 14 days. Results were scored using a 0.0 to 4.0 scoring system, where 0.0 indicated only nonspecific background and 1.0 corresponded to an average of four grains per nucleus.

Breast adenocarcinoma cell lines were obtained from the American Type Culture Collection (Manassus, Md.). Human mammary epithelial cells were described previously and were cultured in mammary epithelial basal media (Clonetics Corp., Walkersville, Md.). Extracts were prepared from exponentially growing cells at 70% confluence, and total RNA isolation and Northern blot analysis were performed.

Paired t-tests were utilized to compare the differences in expression in breast epithelial cells at various stages of tumor progression. Pearson correlation coefficients were used to compare results obtained by in situ hybridization to those obtained for the same cases using immunohistochemistry.

EXAMPLE 12

Expression of GKLF/KFL4 Protein is Increased During Neoplastic Progression in the Breast Eighteen cases were tested for GKLF expression by immunohistochemistry (Table 6, FIG. 9). Nuclear and cytoplasmic staining of normal breast epithelium, DCIS, and invasive carcinoma were semi-quantitatively assessed. Low-level staining of tumor cells was observed for six cases (e.g., cytoplasmic staining ranging from 0.20 to 0.85), with eleven cases exhibiting higher-level staining (e.g., cytoplasmic staining ranging from 1.00 to 1.75). These results are consistent with detection of the mRNA in approximately two-thirds of tumors by in situ hybridization.

For cases 23-31, which were analyzed by both in situ hybridization and immunohistochemical staining, results of the two methods exhibited a close correlation that reached statistical significance for invasive carcinoma cells (N=8, coefficient=0.77, P=0.024). In DCIS, the correlation was moderate even though the sample number was small (N=7, coefficient=0.43). Perhaps due to the overall lower level of expression in uninvolved tissue, the correlation was weakest in uninvolved ducts. Minor differences observed for the two methods may be attributed to differences in sensitivity and specificity, to false negative results due to partial degradation of mRNA in some surgical samples, or to analysis of non-serial sections of the same tissue block.

Figure 10A:
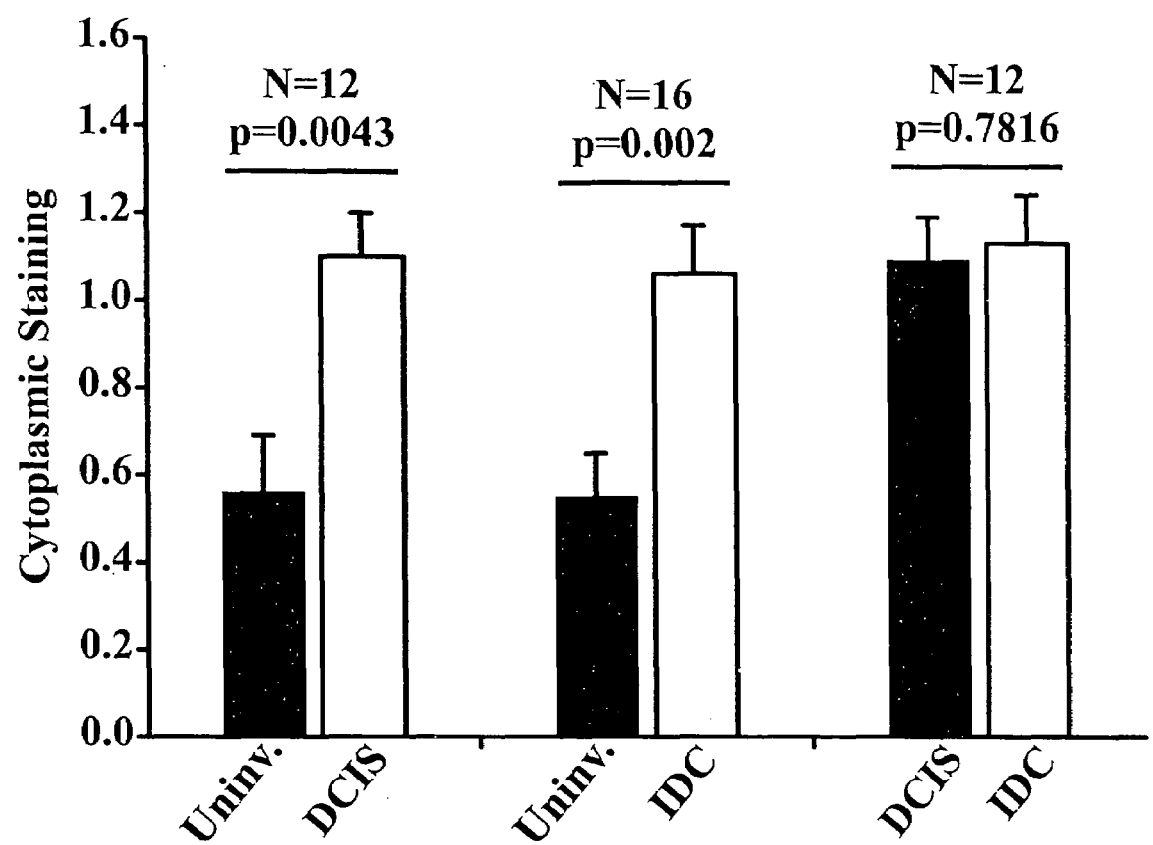
FIGS. 10A-B show staining of uninvolved (FIG. 10A) and neoplastic (FIG. 10B) breast tissue by αGKLF. The data in Table 6 were analyzed using a paired t-test. Sample size (N), statistical significance (p), and standard error of the mean are indicated for each comparison. Uninv, uninvolved ducts; DCIS, ductal carcinoma in situ; IDC, invasive ductal carcinoma.
Figure 10B:
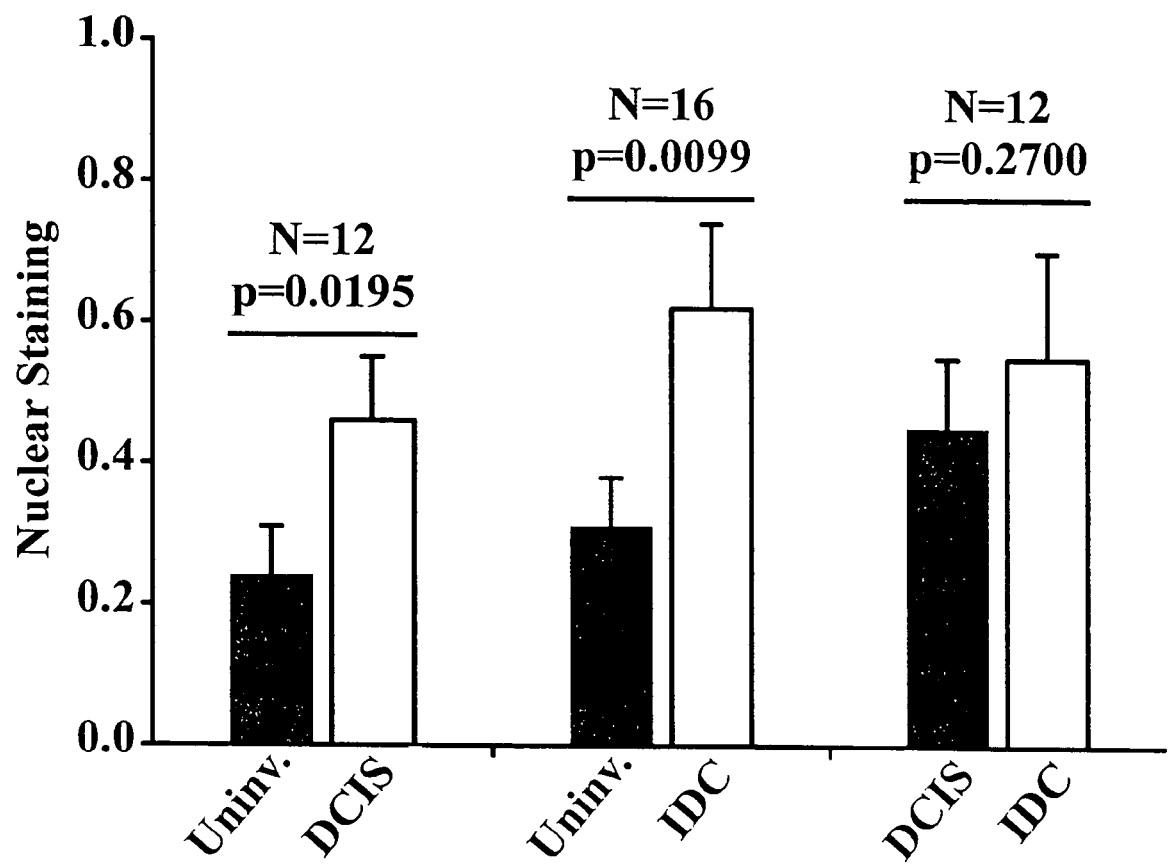
Figure 11:
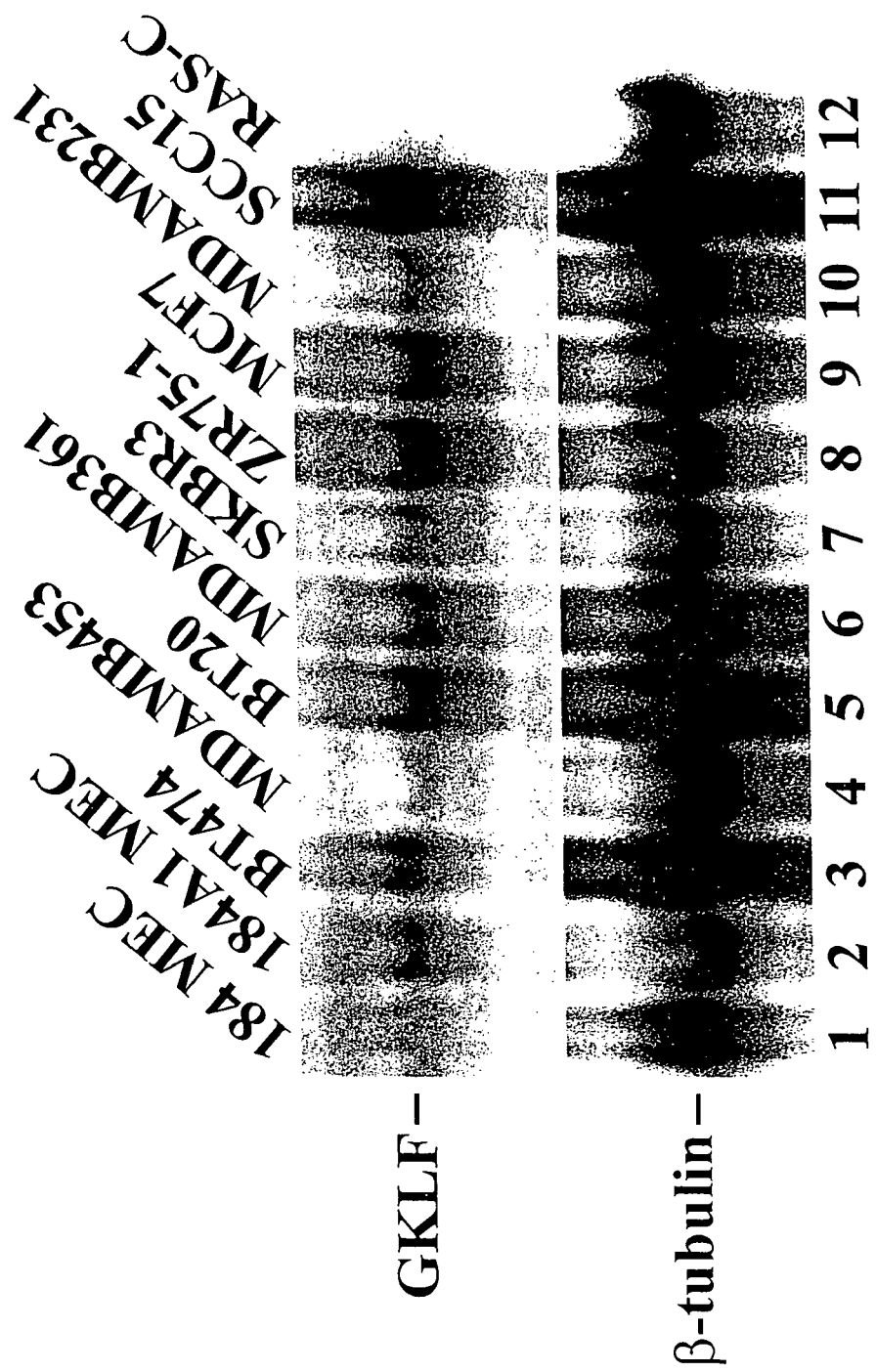
FIG. 11 shows Northern blot analysis of GKLF expression in human breast tumor cell lines. Total RNA from the indicated cell lines was analyzed. Lane 1, finite-lifespan HMECs; lane 2, benzo(a)pyrene-treated, immortalized HMECs; lanes 3-10, breast carcinoma-derived cell lines; lane 11, SCC15, a human oral squamous cell carcinoma-derived cell line; lane 12, a RAS-transformed rat cell line. The filter was stripped and hybridized to a β-tubulin probe.

Apparent GKLF expression as determined by nuclear or cytoplasmic immunostaining was increased in both DCIS and invasive carcinoma compared with uninvolved ducts (Table 6, FIG. 10). For morphologically normal ducts, staining of myoepithelial cells was not significantly different from that of luminal epithelial cells (P=0.303, data not shown). However, staining of neoplastic cells in DCIS was significantly increased compared with myoepithelial cells within the same ducts (P=0.0001), consistent with other studies indicating similarities between tumor cells and luminal epithelial cells.

EXAMPLE 13

Analysis of GKLF/KFL4 Expression in Cultured Breast Epithelial Cells

Northern blot analysis of breast tumor cell lines revealed variable levels of GKLF expression relative to a tubulin control. GKLF expression was high in MCF7 and ZR75-1, intermediate in BT474, BT20, MDAMB361, and SKBR3, and reduced in MDAMB453 and MDAMB231. Thus, expression in six of eight breast tumor-derived cell lines was increased relative to 184 cells, an HMEC population of finite life-span derived from normal breast tissue following reduction mammoplasty (lane 1).

Expression was similarly increased in 184A1 cells. These immortalized cells were derived from 184 cells by treatment with benzo(a)pyrene. They are wild-type for p53 and $p105^{Rb}$ and are anchorage-dependent and non-tumorigenic in animals. The results obtained for breast tumor cell lines support the conclusion that GKLF expression is upregulated at the mRNA level in most breast tumors, while activation in 184A1 cells is consistent with identification of GKLF induction as an early event.

EXAMPLE 14

Oncogene Identification by Transformation of RK3F Cells

The results presented above demonstrate that cells with an epithelial phenotype can be used for identification of transforming activities present in carcinoma-derived cell lines. The assay repeatedly identified two genes, and none of the isolated cDNAs were artificially truncated or rearranged within the protein coding region. This indicates that transformation of these cells is unusually specific to a few pathways or genes, including c-MYC, GKLF, RAS, and GLI. c-MYC, RAS, and GLI are directly or indirectly activated by genetic alterations in diverse carcinoma types during tumor progression in vivo. For both breast and oral squamous carcinoma, the tumor-types analyzed in this study, c-MYC gene amplification is one of the more frequent oncogene genetic alterations and is observed in 10-15% of cases. By analogy, novel oncogenes identified by the RK3E assay may be directly activated in neoplasms through gain-of-function mutations or indirectly activated by loss-of-function genetic alterations.

The retroviral vectors used in this study for transduction of NIH3T3 cells were developed by Kay and colleagues (Whitehead et al., 1995). Using the NIH3T3 line, they isolated 19 different cDNAs encoding 14 different proteins. Known oncogenes were isolated including raf-1, 1ck, and ect2. Other known genes included phospholipase $C-\gamma_2$, β-catenin, and the thrombin receptor. In addition to the known genes, seven novel cDNAs were isolated, including several members of the CDC24 family of guanine nucleotide exchange factors. Only the thrombin receptor was isolated more than once, and many of the 14 different genes identified were truncated within the protein coding region. The diversity of cDNAs isolated in the NIH3T3 assay is in contrast to results obtained in the current study. The specificity of the RK3E assay may be attributable to the "tumor suppressor" activity of the E1A oncogene. Although E1A antagonizes $p105^{Rb}$ and immortalizes primary cells, it also induces epithelial differentiation in diverse tumor types, including sarcoma, and suppresses the malignant behavior of tumor cells in vivo.

EXAMPLE 15

GLKF/KFL4 as an Oncogene

GKLF was previously isolated by hybridization to zinc finger probes. The human gene is located at chromosome 9q31 and is closely linked to the autosomal dominant syndrome of multiple self-healing squamous epitheliomata. Affected individuals develop recurrent invasive but well-differentiated tumors morphologically similar to squamous carcinoma that spontaneously regress. Although GKLF has been proposed as a candidate tumor suppressor gene relevant to multiple self-healing squamous epitheliomata, the results suggest that activating mutations could account for the syndrome.

GKLF encodes a nuclear protein that functions as a transcription factor when bound to a minimal essential binding site of $5'-^G/_A^G/_A GG^C/_T G^C/_T-3'$ (SEQ ID No. 8). The 470 residue polypeptide exhibits modular domains that mediate nuclear localization, DNA binding, and transcriptional activation or repression. In mice, GKLF expression is found predominately in barrier epithelia including mucosa of the mouth, pharynx, lung, esophagus, and small and large intestine. A role for GKLF in differentiation or growth-arrest was suggested by onset of expression at the time of epithelial differentiation (approximately embryonic day 13), and by similarity within the zinc finger domain to family members EKLF and LKLF that were previously associated with growth-arrest or differentiation-specific gene expression. Similarity to these other genes is limited to the DNA binding zinc finger region.

The results show that GKLF can induce proliferation when over-expressed in vitro. Analysis of expression in dysplastic cells and tumor cells in vivo provides independent evidence that GKLF exhibits properties expected of an oncogene. Genetic progression of carcinoma appears to involve genes and pathways important for homeostasis of normal epithelium. For example, the zinc finger protein GLI is expressed in normal hair shaft keratinocytes, while c-MYC is expressed in normal epithelium of the colonic mucosa. In tumors derived from these tissues, GLI and c-MYC are more frequently activated by recessive genetic changes in upstream components of their respective biochemical pathways than by gain-of-function alterations such as gene amplification. Up-regulation of GKLF expression in dysplastic epithelium and tumor cells in vivo is particularly interesting as expression appears not to be increased by proliferation in vitro. Expression of the endogenous GKLF mRNA in RK3E cells was similar in cycling vs. contact-inhibited cells (data not shown). In contrast, GKLF is significantly induced in NIH3T3 cells during growth-arrest. These different results suggest that cell type-specific mechanisms can regulate GKLF expression, and that GKLF may play different roles in epithelial vs. mesenchymal cells.

Squamous epithelium is divided into compartments. In the basal layer, proliferative stem cells possess unlimited self-renewal capacity, while transit amplifying cells undergo several rounds of mitosis and then withdraw from the cell cycle and terminally differentiate. Proliferation and differentiation are normally balanced such that overall cell number remains constant. In contrast to GLI and c-MYC, GKLF expression in skin appears limited to the differentiating compartment. A simple model is that GKLF normally regulates the rate of maturation and shedding and the overall transit time for individual cells. The thickness of epithelium, which varies greatly in development and in different adult tissues, may be regulated not only by alterations in the rate of cell division in the basal layer, but also in response to GKLF or similarly acting molecules in the suprabasal layers. This model is consistent with the relatively late induction of GKLF during mouse development, and is testable by modulating expression of GKLF in transgenic animals or using raft epithelial cultures in vitro. Activation of GKLF in the basal layer of dysplastic epithelium suggests that dysplasia and progression to invasion and metastasis could result from loss of normal compartment-specific patterns of gene expression.

GKLF, c-MYC and GLI are potent oncogenes in epithelioid RK3E cells in vitro, are analogous with respect to their expression in normal epithelium, and have potentially complex roles in the regulation of epithelial cell proliferation, differentiation, or apoptosis. Analysis of well-characterized tumor types such as colorectal carcinoma and basal cell carcinoma of the skin suggests that genetic alterations cluster within specific pathways, rather than within any specific gene, and that these pathways can function as regulators of oncogene transcription. An activity common to several oncogenes implicated in carcinoma is the ability to induce transformed foci in the RK3E assay. This assay is highly specific, as foci result from expression of tumor-derived mutant (but not wild-type) alleles of RAS or β-catenin, and only GKLF and c-MYC were identified in a large screen. The assay also detects a distinct subset of oncogenes compared with other host cell lines. With the exception of RAS, the oncogenes that transform RK3E cells do not induce foci in NIH3T3 cells.

GKLF encodes a zinc finger transcription factor of the GLI-Krüppel family and is distinct from many other oncogenes in that expression in normal tissue is observed in terminally differentiating epithelial cells. In addition, expression is induced in association with cell growth-arrest in vitro. As predicted by these observations, expression in certain tumor-types is reduced compared with the relevant normal epithelia. Thus, GKLF expression is reduced in colorectal tumors, a result supported by multiple approaches including analysis of RNA extracted from tissues, SAGE, and immunohistochemical analysis of human tissues. In situ hybridization analysis of several prostatic tumors likewise indicates that GKLF is expressed in normal prostatic epithelium, and that expression can be lost during tumor progression.

In contrast to colorectal and prostatic carcinoma, GKLF expression is activated in both invasive carcinoma and preinvasive neoplastic lesions during progression of most breast carcinomas and virtually all oropharyngeal squamous cell carcinomas. Breast and oral cancer share a number of additional molecular alterations. Loss-of-function mutations frequently affect p53 and p16/CDKN2, while a smaller proportion of tumors (5-20%) exhibit gene amplification of c-MYC, cyclin D1, erbB-family members including the EGF receptor and erbB-2/HER-2/neu, or others. Unlike carcinomas of the GI tract or skin, neither breast nor oral carcinoma is reported to exhibit frequent genetic alterations that activate known transforming oncogenes such as RAS, β-catenin, c-MYC, or GLI. By analogy with oncogenes in other tumor types, disruption of the pathways that control GKLF mRNA expression in breast epithelial cells and in oral mucosa represents a potential mechanism of tumor initiation or progression in vivo.

The pattern of GKLF expression in normal epithelia may provide clues as to how GKLF functions in tumor progression. Stratified squamous epithelium contains at least four functionally-distinct compartments. The stem cell compartment is composed of cells within the basal cell layer that exhibit a capacity for self-renewal, but which rarely divide. The transit amplifying compartment is composed of cells within the basal or parabasal cell layers that exhibit rapid cell division, but a reduced capacity for self-renewal. Differentiation occurs within the prickle cell layer that contains identifiable desmosomes, leading to the outermost, keratinized superficial layer. While mechanisms regulating transitions from one compartment to the next remain poorly understood, c-MYC activation can induce stem cells to enter the highly proliferative transit amplifying compartment. Since self-renewal and rapid cell division occur in distinct cell-types, the organization of compartments enables rapid turnover of epithelial cells while minimizing the possibility of sustaining permanent genetic damage in stem cells.

The observation that GKLF functions normally in the prickle cell layer suggests that each of the three compartments—stem cell, transit amplifying, and prickle layer—expresses a transforming activity or a critical function (e.g., self-renewal or proliferation) that may contribute to progression of carcinoma. These compartments appear to be intermingled in dysplastic stratified squamous epithelium, with prickle layer markers including GKLF misexpressed in the basal layers, while other basal or parabasal markers are misexpressed in superficial layers. Loss of these compartment-specific patterns of gene expression may result in co-expression of properties of several compartments in a single cell. For example, specific properties of the prickle cell layer, such as reduced cellular adhesion to basement membranes, altered adhesion to other cells, and/or loss of the cellular mechanisms that mediate contact inhibition could confer invasive or metastatic properties to oral carcinomas. Although breast epithelium is derived from skin during embryogenesis, the biology and organization of normal breast epithelium is distinguished from skin in many aspects. However, the organization of compartments is likely to be similar, and loss of such organization as a consequence of GKLF activation and other alterations may contribute to tumor progression.

To better understand the mechanism of transformation, transcriptional alterations induced by GKLF are being characterized when expressed in epithelial cells in vitro. In the future, identification of upstream regulators of GKLF transcription in epithelial cells may elucidate the pathways that regulate GKLF, and the mechanism of deregulation of GKLF in specific tumor-types.

EXAMPLE 16

Subcellular Localization of KFL4/GKLF Identifies Breast Cancer Patients with a Distinct Clinical Outcome As described above, KLF4 encodes a zinc finger transcription factor that was identified as an oncogene using expression cloning in the RK3E epithelial model. Mouse knockout studies revealed an essential role for KLF4 in skin differentiation, consistent with expression of KLF4 in superficial, nondividing cell layers in normal skin and oral mucosa. KLF4 mRNA and protein expression are upregulated at an early step during progression of most breast and oral cancers, but not in colorectal or prostatic carcinoma. Thus, de novo expression of KLF4 within proliferating epithelial compartments may represent a mechanism of tumor initiation or progression.

Ki67, a 395-kd gene product, is a popular marker of cell proliferation in normal and neoplastic tissues associated with the cell cycle. Expression of Ki67 is closely associated with the proliferation phase and is absent during the resting phase of cell cycle5.6. Expression of KLF4 and Ki67 were examined by immunohistochemical staining of normal breast tissue obtained by reduction mammoplasty.

Figure 12:
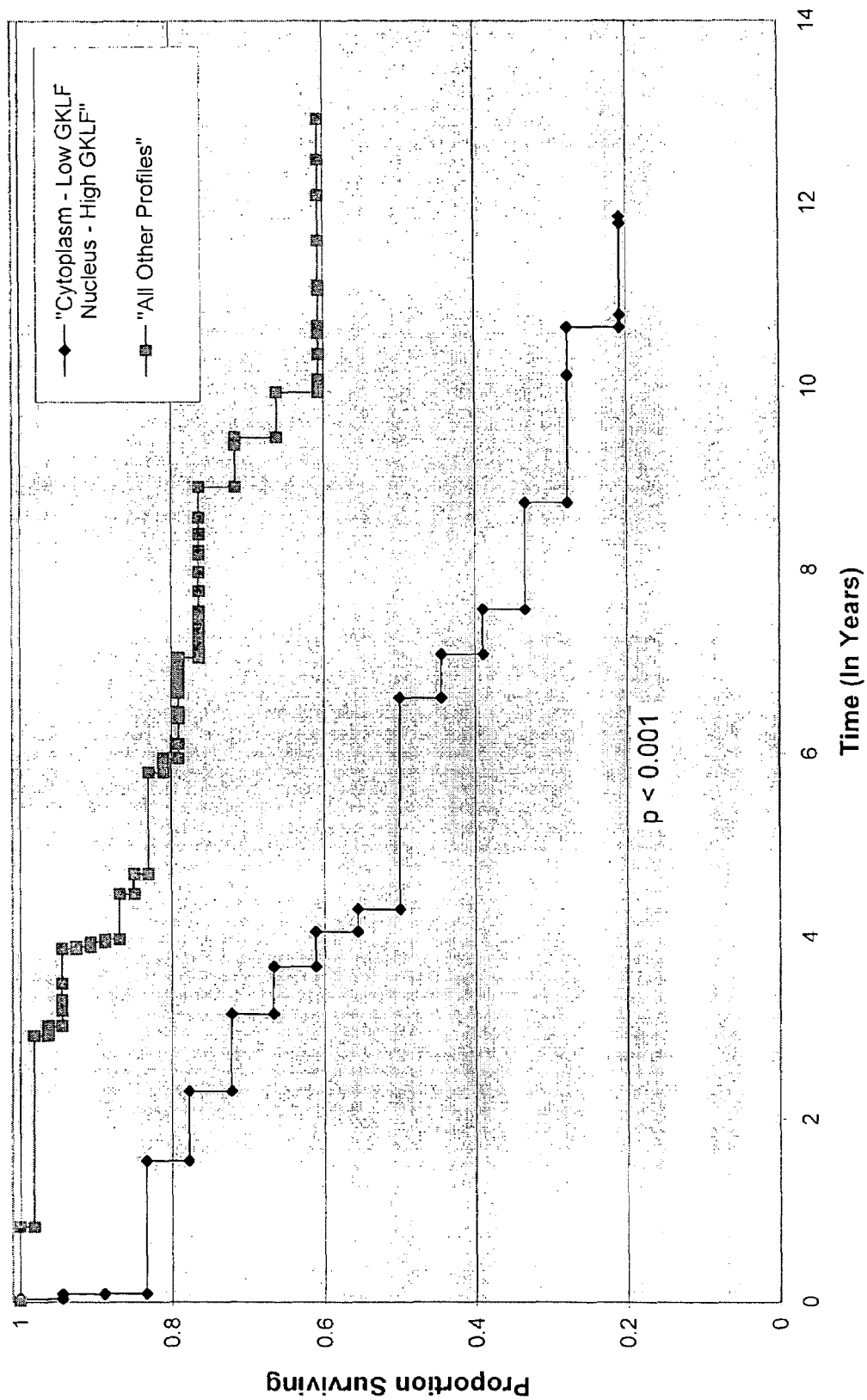
FIG. 12 shows survival rates of invasive breast cancer patients according to GKLF staining patterns in the cytoplasm and nucleus (includes small tumors only).
Figure 13A:
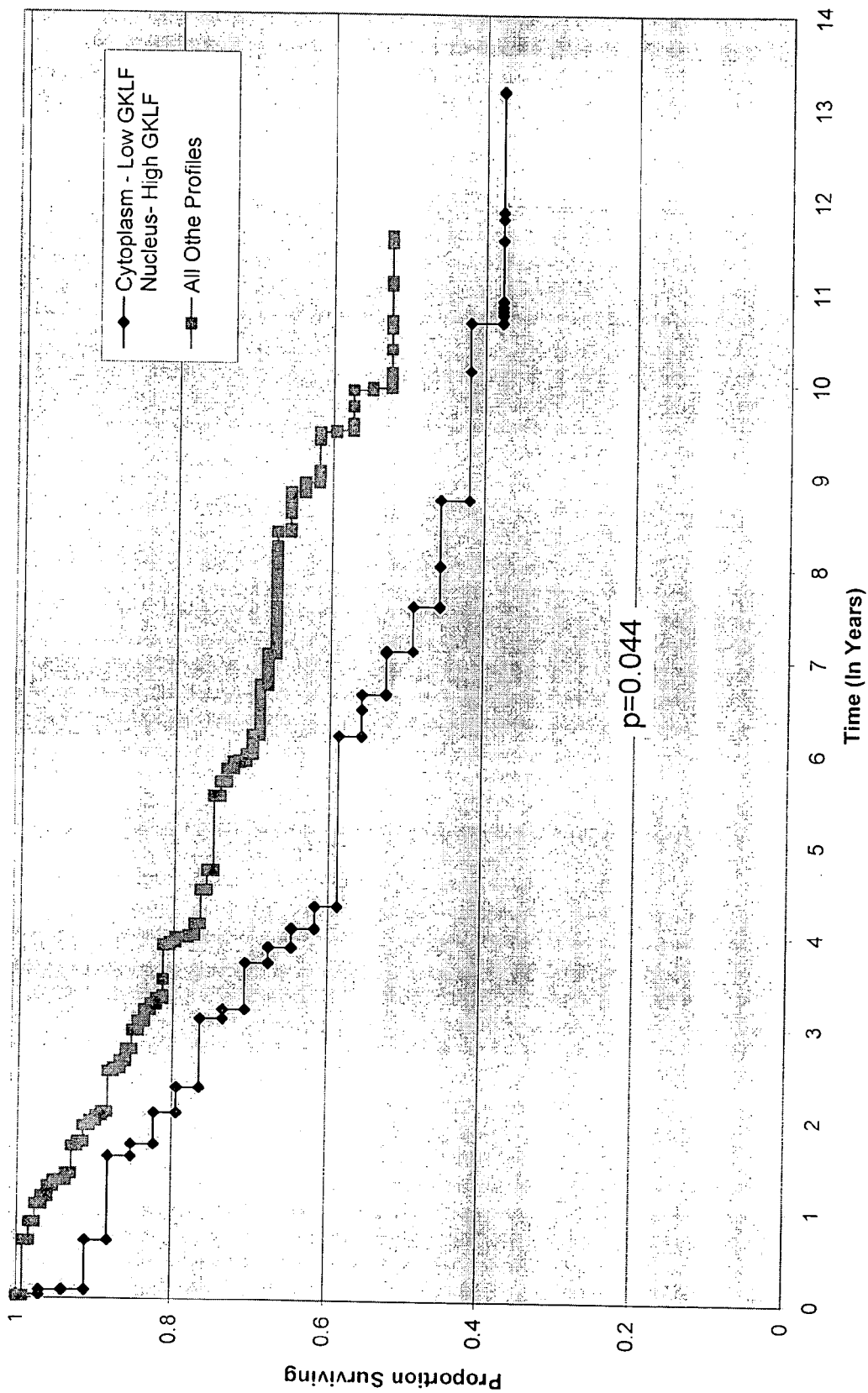
FIGS. 13A-B show survival rates of invasive breast cancer patients according to GKLF staining patterns in the cytoplasm and nucleus (using the median immunoscore as the cut off).
Figure 13B:
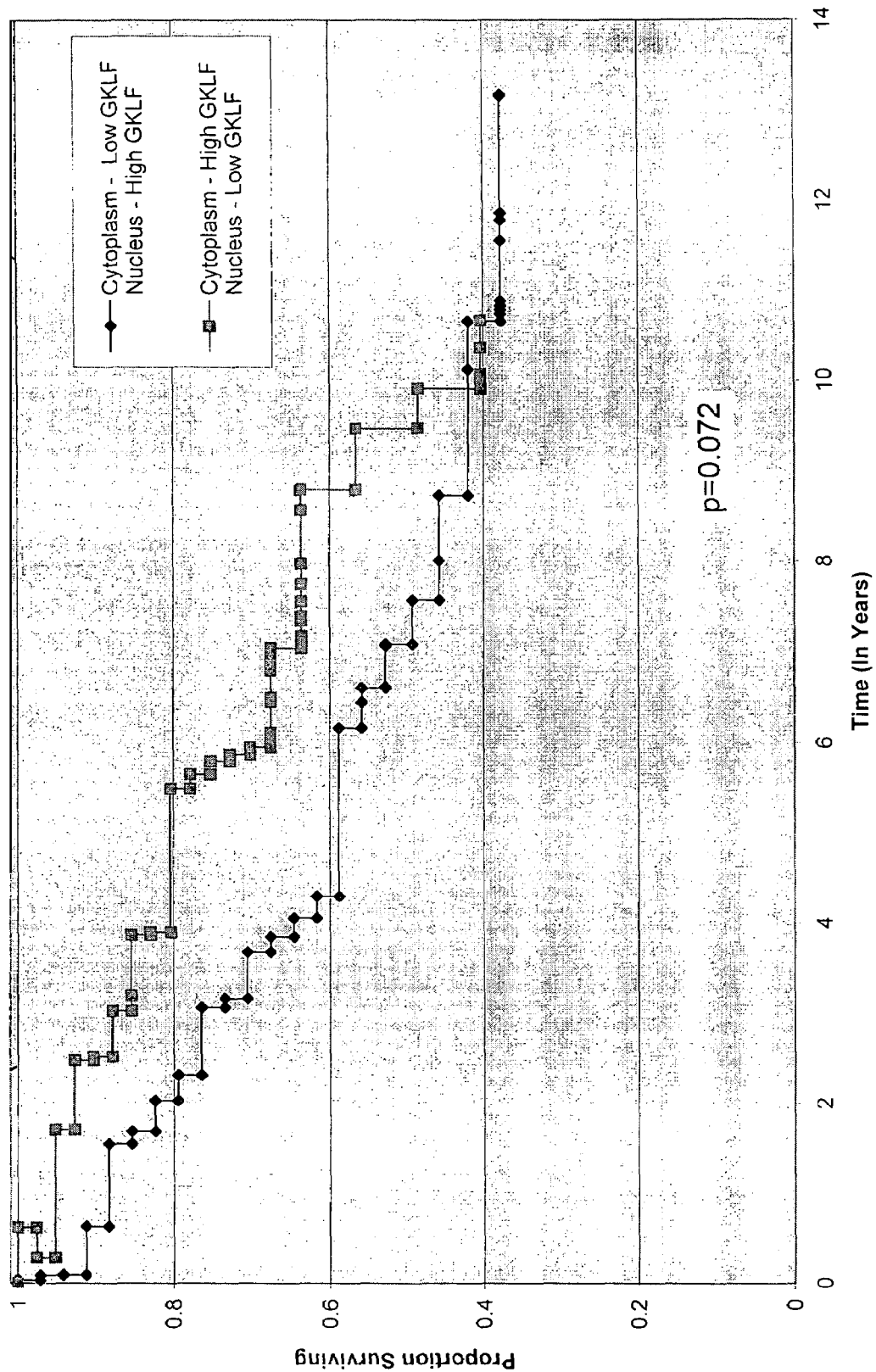

Overall expression of KLF4 is low or undetectable in normal breast epithelium, with a mixed nuclear and cytoplasmic staining pattern. See FIGS. 12, 13A and 13B and Tables 7 and 8. A subset of lobular units exhibit prominent nuclear staining, and these lobules were low or negative for expression of Ki67.

These results indicate that KLF4 may play a normal role in differentiating lobules, consistent with its role in other epithelial tissues such as the skin or the colorectal mucosa. In addition, co-expression of KLF4 and Ki67 may be specific to malignant cells and may help to discriminate between normal breast epithelial cells and malignant cells in clinical samples.

KLF4 expression in breast tumors identifies three distinct patterns: predominantly cytoplasmic, predominantly nuclear, or mixed, with the mixed staining pattern being most common. Initial outcome analysis indicates a 5-year survival rate of 76% for patients with prominent cytosolic staining (52 of 68 patients with >median cytosolic staining survived for 5 years or greater) vs. 60% for patients with low cytosolic staining (38 of 63 patients with <median cytosolic staining; p=0.0464). These results are consistent with a function of nuclear KLF4 as a transforming oncogene, and indicate that activity of the protein is likely to be regulated by subcellular localization in breast tissues.

TABLE 7

Characteristics of the Study Population According to GKLF Cytoplasmic and Nucleic Staining Profile (Low Cytoplasmic GKLF and High Nucleic GKLF versus High Cytoplasmic GKLF and Low Nucleic GKLF)

|  | Low Cytoplasmic GKLF High Nucleic GKLF | | High Cytoplasmic GKLF Low Nucleic GKLF | | |
|---|---|---|---|---|---|
|  | n | % | n | % | P-value |
| Race |  |  |  |  |  |
| White | 26 | 74.29 | 29 | 70.73 | 0.732 |
| Black | 9 | 25.71 | 12 | 29.27 |  |
| Menopausal Status |  |  |  |  |  |
| Pre | 17 | 48.57 | 17 | 41.46 | 0.537 |
| Post | 18 | 51.43 | 24 | 58.54 |  |
| Stage |  |  |  |  |  |
| I | 26 | 78.79 | 23 | 58.97 | 0.074 |
| >I | 7 | 21.21 | 16 | 41.03 |  |
| Lymph Nodes |  |  |  |  |  |
| Negative | 21 | 60.0 | 18 | 51.43 | 0.474 |
| Positive | 14 | 40.0 | 17 | 48.57 |  |
| Tumor Size |  |  |  |  |  |
| ≤2 cm. | 18 | 51.43 | 22 | 53.66 | 0.847 |
| >2 cm. | 17 | 48.57 | 19 | 46.34 |  |
| Histologic Grade |  |  |  |  |  |
| Low | 13 | 38.24 | 15 | 51.72 | 0.287 |
| High | 21 | 61.76 | 14 | 48.28 |  |

TABLE 8

Characteristics of the Study Population According to GKLF Cytoplasmic and Nucleic Staining Profile (Low Cytoplasmic and High Nucleic GKLF vs. All Others)

| | Low Cytoplasmic GKLF High Nucleic GKLF (N = 36) | | All Other Profiles (N = 138) | | |
|---|---|---|---|---|---|
| | n | % | n | % | P-value |
| Race | | | | | |
| White | 26 | 74.29 | 93 | 71.54 | 0.748 |
| Black | 9 | 25.71 | 37 | 28.46 | |
| Menopausal Status | | | | | |
| | 17 | 48.57 | 52 | 39.69 | 0.345 |
| Post | 18 | 51.43 | 79 | 60.31 | |
| Stage | | | | | |
| I | 26 | 78.79 | 88 | 68.22 | 0.237 |
| >I | 7 | 21.21 | 41 | 31.78 | |
| Lymph Nodes | | | | | |
| Negative | 21 | 60.0 | 76 | 61.79 | 0.848 |
| Positive | 14 | 40.0 | 47 | 38.21 | |
| Tumor Size | | | | | |
| ≦2 cm. | 18 | 51.43 | 55 | 44.35 | 0.460 |
| >2 cm. | 17 | 48.57 | 69 | 55.65 | |
| Histologic Grade | | | | | |
| Low | 13 | 38.24 | 53 | 54.08 | 0.113 |
| High | 21 | 61.76 | 45 | 45.92 | |

EXAMPLE 17

KLF4 Immunostaining in 146 Cases of Human Primary Infiltrating Ductal Carcinoma of the Breast The following examples examine KLF4 expression by immuno-staining in 146 cases of human primary infiltrating ductal carcinoma of the breast. Staining patterns were correlated with clinical outcome and with established prognostic factors.

Table 9 identified 146 cases of infiltrating ductal carcinoma that were well characterized for clinical and pathologic parameters including surgical management, stage at diagnosis, histologic grade, post-operative therapy, and cause of death. One hundred thirty four of the 146 patients (92%) underwent axillary lymph node dissection with at least five lymph nodes sampled, and 10 or more lymph nodes were sampled for 116 patients (79%). The median follow-up from the time of diagnosis was 7.1 years. Patients with early stage disease (i.e., Stages I and IIA) exhibited a five-year disease specific survival rate of 87% (see FIG. 15B), similar to that observed in larger studies. Likewise, patients with Stage IIB, Stage III, or Stage IV disease exhibited five-year survival rates (75%, 37%, or 20%, respectively) similar to rates observed for larger groups. The investigators analyzed expression of KLF4 and other prognostic or predictive factors, including steroid hormone receptors estrogen receptor and progesterone receptor, receptor tyrosine kinase ERBB2, proliferation marker Ki67, tumor suppressor p53, and two markers associated with favorable clinical outcome, BCL2 and the cyclin-dependent kinase inhibitor p27KIP1.

Tissue samples were fixed in neutral buffered formalin and embedded in paraffin. To avoid antigen decay, sections were cut to 5 mm thickness one day prior to immunostaining. Sections were attached to the slide by heating in a 60° C. oven for one hour. Deparaffinized tissue sections were treated for 5 minutes in a 3% aqueous solution of hydrogen peroxide, blocked in PBS with 3% goat serum (Sigma) for 1 hour at room temperature, and then incubated for 1 hour at room temperature with anti-KLF4 monoclonal antibody IE5 at 1.0 mg/ml in binding buffer (PBS containing 1% bovine serum albumen, 1 mM EDTA, and 0.01% sodium azide). Anti-KLF4 was stored in aliquots at −85° C., and was stable through multiple freeze/thaw cycles. Activity is lost within weeks when stored at 4° C. Slides were washed in 50 mM Tris-HCl (pH 7.6), 150 mM NaCl, 0.01% (v/v) triton X-100. Immunodetection was performed using a biotinylated secondary antibody, streptavidin-horseradish peroxidase (Signet Pathology Systems), and the chromogenic substrate diaminobenzidine (BioGenex). Sections were counterstained with Harris' hematoxylin (Surgipath). As controls, histologic sections of each case were processed without the addition of primary antibody for each antigen retrieval method along with positive/negative, multi-tissue control sections.

For the detection of estrogen receptor, progesterone receptor, p27KIP1, and Ki67, histologic sections were subjected to low temperature antigen retrieval with enzymatic pretreatment. This consisted of pre-digestion in 0.1% trypsin (Type II-S from porcine pancreas, Sigma) in PBS for 15 minutes at 37° C., followed by incubation in 10 mM citrate buffer, pH 6, for two hours at 80° C. The antibodies used were anti-estrogen receptor mouse monoclonal antibody clone ER88 (0.33 mg/ml total protein; Biogenex) at 1:30 dilution; anti-progesterone receptor mouse monoclonal antibody clone PR88 (0.33 mg/ml total protein; Biogenex) at 1:30 dilution; anti-Ki67 mouse monoclonal antibody clone MIB-1 (0.37 mg/ml total protein; Biogenex) at 1:30 dilution; and anti-p27KIP1 mouse monoclonal antibody, clone 1B4 (8.0 µg/ml IgG; Novocastra Laboratories Ltd.) at 1:30 dilution. Immunostaining for BCL2 was preceded by incubation of histologic sections in boiling 10 mM sodium citrate buffer (pH 6.0) for 10 minutes in a microwave oven. Anti-BCL2 (clone 124, Genosys Biotechnologies, Inc.) was used at 12.5 mg/ml. Anti-ERBB2 (clone 3B5, Oncogene Research Products) was used at 0.25 mg/ml. Anti-p53 (clone BP53.12, Oncogene Research Products) was used at 0.25 mg/ml.

The intensity of immunostaining of individual cells was scored on a scale of 0 (no staining) to 4 (strongest intensity) and the percentage of cells with staining at each intensity was estimated. For ERBB2, only membranous staining was assessed. The proportion of cells at each intensity was multiplied by the corresponding intensity value, and these products were added to obtain an immunostaining score (immunoscore) ranging from 0 to 4. All slides were examined and scored independently by two investigators, large discordances were reconciled by re-examination of the slide, and the scores were then averaged.

The Nottingham modification of the Bloom and Richardson histologic grading system was used to categorize carcinomas as high grade, corresponding to a total score of 8 or 9, or low-to-moderate grade (referred to as low), corresponding to a total score of less than 8 (Elston and Ellis, 1991).

Median immunoscores were used to group cases with high or low expression levels of KLF4, Ki67, BCL2, ERBB2, or P27KIP1. For estrogen receptor, progesterone receptor, and p53, tumors with >10% positive cells were scored as positive. Associations of clinical, pathologic, and demographic factors with KLF4 staining patterns were evaluated using the Mantel-Haenszel chi-square test or, where appropriate, Fisher's exact test. Kaplan-Meier methods were used to compare overall survival rates and significance was assessed using the Log Rank test. Survival time was defined as the interval from the date of diagnosis to the date of death. Patients who were alive at the last date of contact, died from unknown causes or died from causes other than breast cancer were censored at the date of last contact.

Multivariate Cox proportional hazards models were performed to evaluate the effect of KLF4 staining patterns on survival while controlling for the effects of extraneous factors. The analysis was performed using a step-wise selection technique. Included in the full model were KLF4, race, chemotherapy, stage, histologic grade, estrogen receptor, and progesterone receptor. Significance level to stay in the model was set at 0.050. In addition, interaction terms were included in the model to evaluate the multiplicative effect of KLF4 staining patterns and various clinical or pathologic factors on survival. All significance tests were two-sided with alpha=0.05.

TABLE 9

Characteristics of the Study Population

| | n | % |
|---|---|---|
| Demographics | | |
| Age at diagnosis (yrs) | | |
| ≦50 | 68 | 47 |
| >50 | 78 | 53 |
| Race | | |
| African-American | 42 | 29 |
| Caucasian | 104 | 71 |
| Postoperative treatment (received treatment/total) | | |
| Chemotherapy | 70/142 | 49 |
| Radiotherapy | 41/142 | 29 |
| Tamoxifen | 72/133 | 54 |
| Stage and Tumor Grade (high grade/total) | | |
| Stage I | 9/38 | 24 |
| Stage IIA | 32/59 | 54 |
| Stage IIB | 18/29 | 62 |
| Stage III-IV | 17/20 | 85 |
| Outcome (death due to breast cancer/total) | | |
| Stage I | 12/38 | 32 |
| Stage IIA | 11/59 | 19 |
| Stage IIB | 11/29 | 38 |
| Stage III | 9/15 | 60 |
| Stage IV | 4/5 | 80 |

EXAMPLE 18

Distinct Patterns of KLF4 Subcellular Localization in Breast Tumors

Figure 14A:
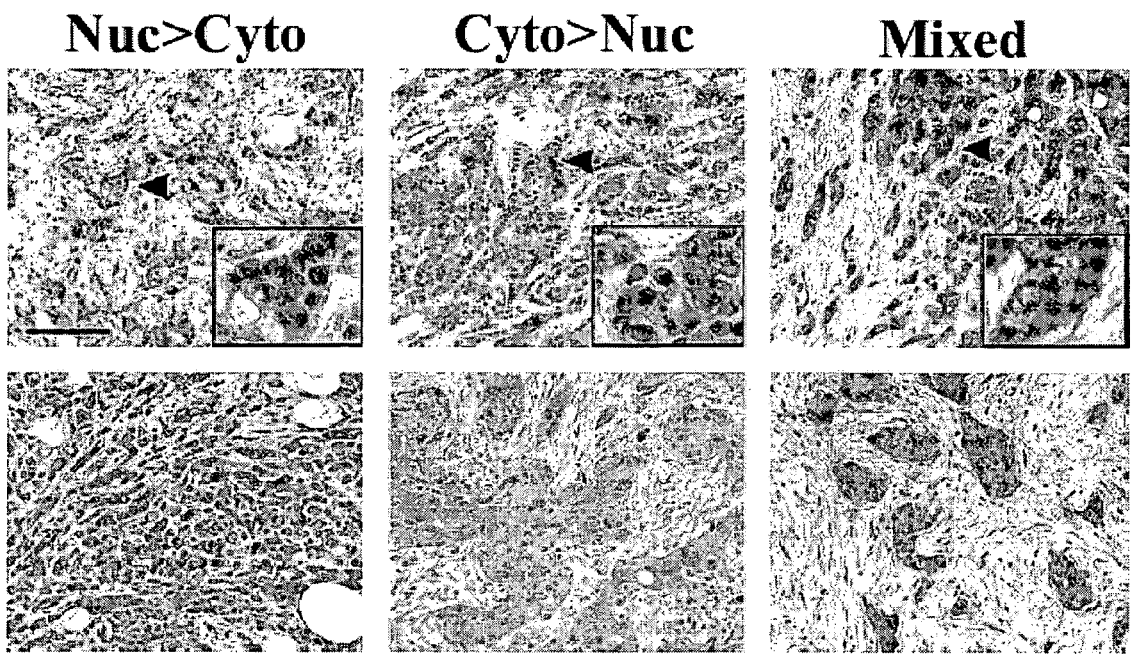
FIGS. 14A-B show immunostaining of human breast cancers with anti-KLF4 monoclonal antibody.
Figure 14B:
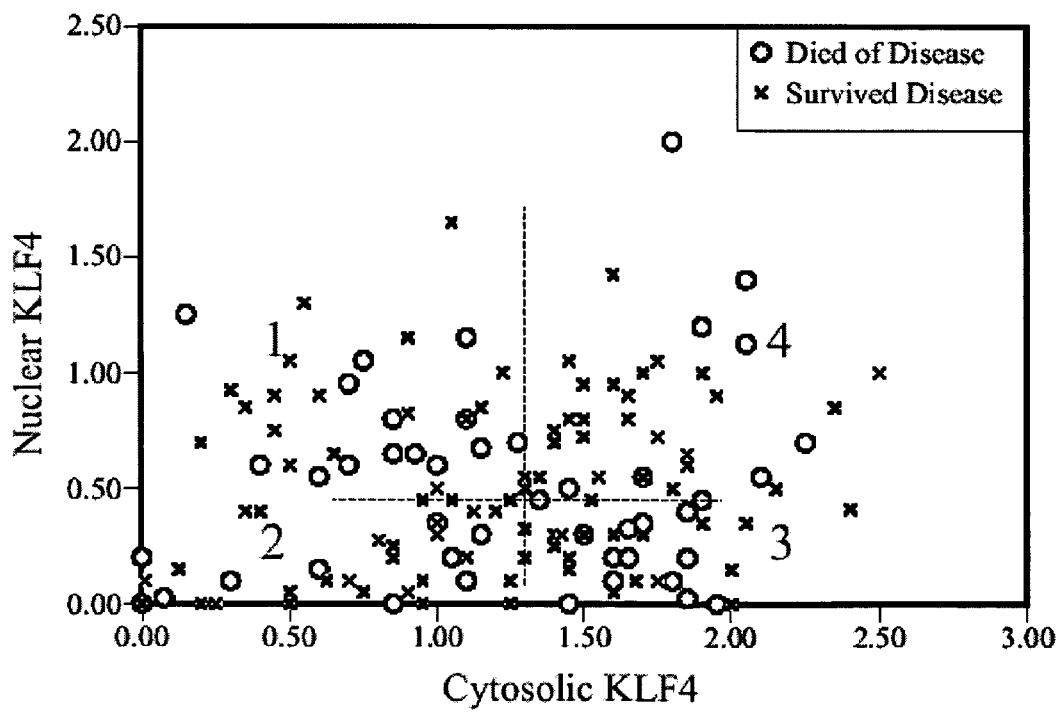

Overall, expression was detected in >90% of cases. Primary tumors varied greatly in their relative staining of the nucleus and cytoplasm (FIG. 14A). The pattern of subcellular localization within individual tumors was quite uniform across a histologic section, and was similar in invasive and in situ components within the same section (FIG. 14A and data not shown). Scatterplot analysis demonstrated the spectrum of staining patterns observed in these tumors (FIG. 14B). Based upon the four quadrants defined by the median immunostaining scores, tumors were classified as Type 1, 2, 3, or 4. Type 1 tumors exhibit higher than median nuclear staining, and lower than median cytoplasmic staining. Type 2 tumors have lower staining in each compartment. Type 3 tumors have predominantly cytoplasmic staining, and Type 4 tumors have increased staining in each compartment.

Figure 15A:
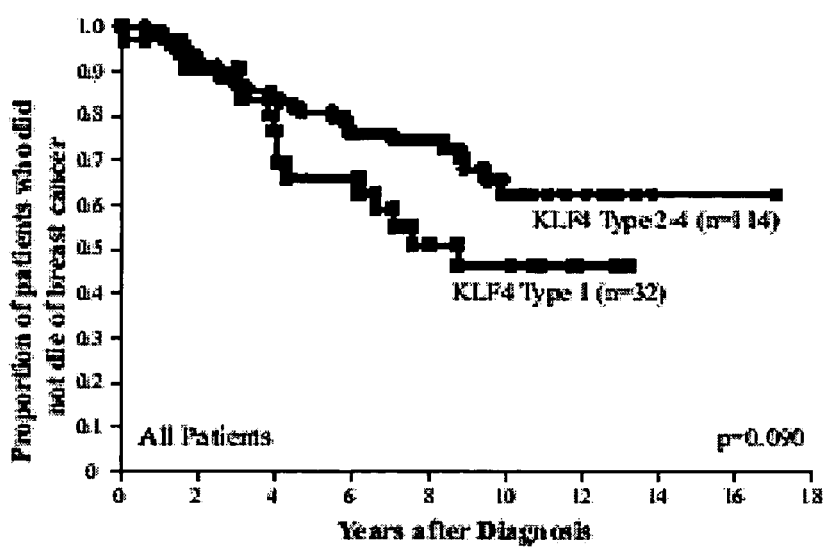
FIGS. 15A-C shows Kaplan-Meier estimate of disease-specific survival according to KLF4 staining pattern.

As KLF4 is likely to function in the nucleus rather than in the cytoplasm, the investigators evaluated the impact of preferential nuclear expression of KLF4 on survival (FIG. 15A). Type 1 tumors were compared to all other tumors combined (referred to as Type 2-4). Although Type 1 tumors appeared to be more often associated with death from breast cancer, this trend was not statistically significant (Log Rank test, P=0.090). No significant differences were obtained by comparison of Type 3 tumors vs. all others (P=0.227). Likewise, tumors with high vs. low nuclear expression exhibited similar outcomes (i.e., using the median score as cutoff; P=0.601), as did tumors with high vs. low cytoplasmic expression (P=0.157).

EXAMPLE 19

KLF4 Expression in Small Primary Breast Tumors

Figure 15B:
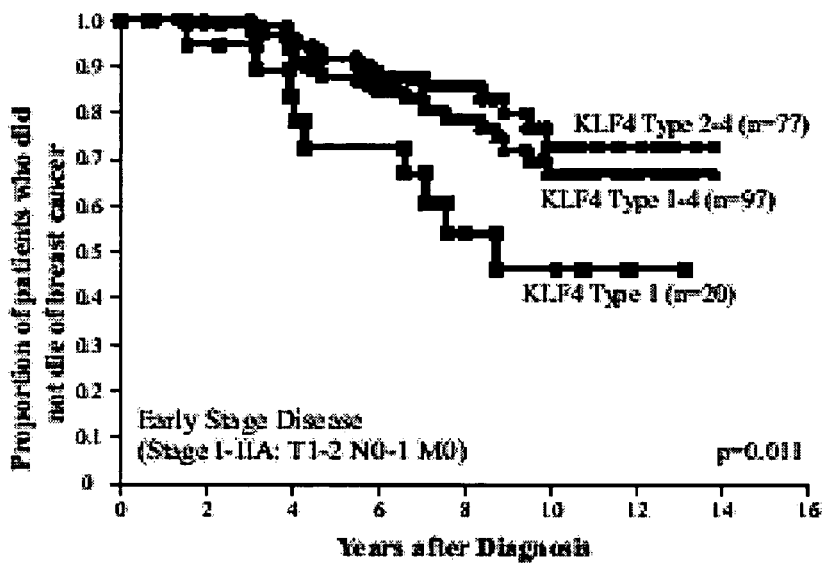
Figure 15C:
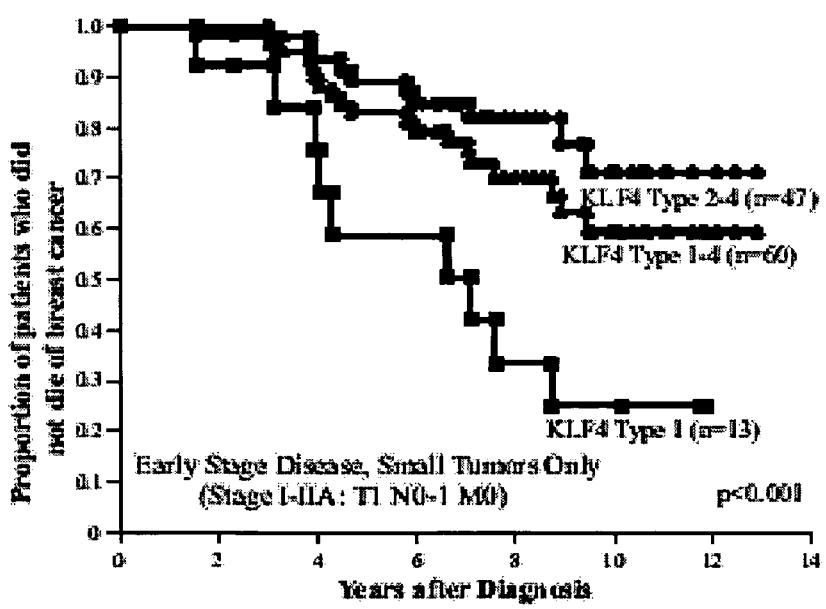

The trend observed for all cases combined was more pronounced for patients who were diagnosed with early stage cancer (i.e., Stages I and IIA; FIG. 15B; P=0.011). Tabulation of outcome by stage and KLF4 staining pattern suggested an important role for size of the primary tumor in the association of KLF4 with clinical outcome (Table 10). Indeed, all nine of the deaths among patients with Type 1 staining and early stage disease occurred in the setting of a small primary tumor (i.e., less than or equal to 2.0 cm in diameter, indicated as T1). For the seven patients with T1 N0 M0 (i.e., Stage I) disease and Type 1 staining, all but two succumbed to breast cancer. In contrast, none of the seven patients who had T2 N0 M0 (Stage IIA) disease with Type 1 staining died from breast cancer (P=0.010). The median follow-up time for these groups was 4.30 years (Stage I) and 8.01 years (Stage IIA). Thus, patients with early stage disease and small primary tumors were much more likely to die from breast cancer when the KLF4 staining pattern was Type 1 (FIG. 15C; P<0.001).

Figure 16A:
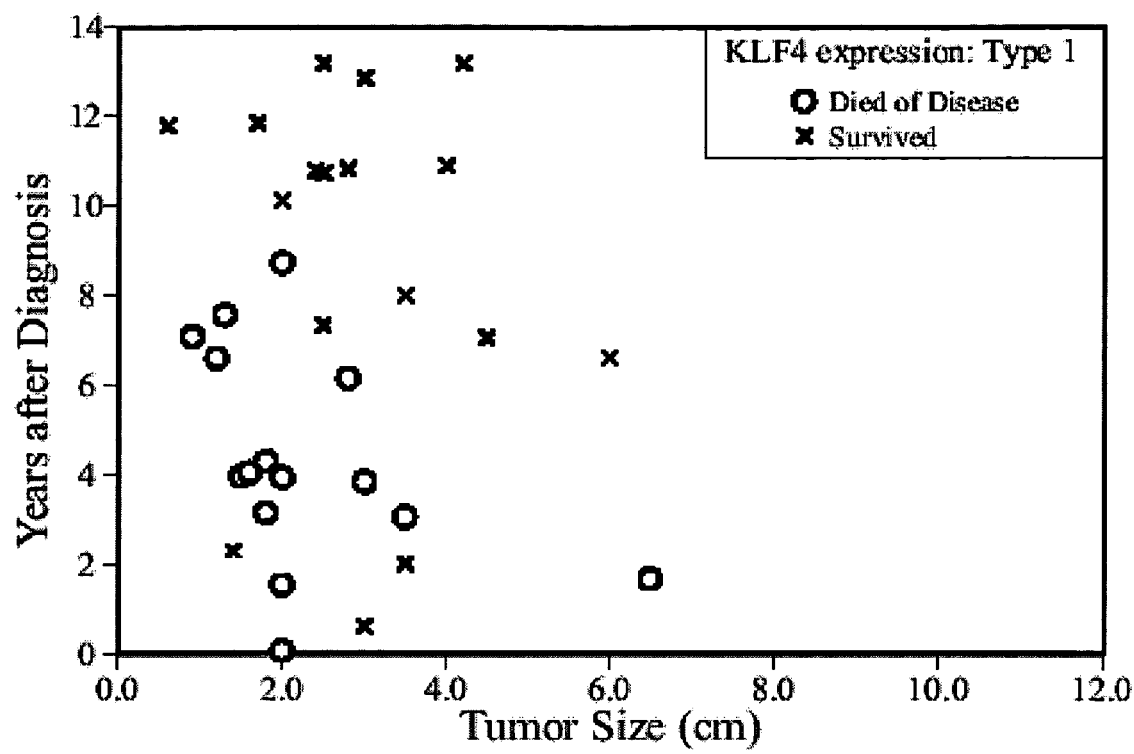
FIGS. 16A-B shows scatter-plot analysis of disease-specific survival (years after diagnosis) according to tumor size and KFL4 staining pattern.
Figure 16B:
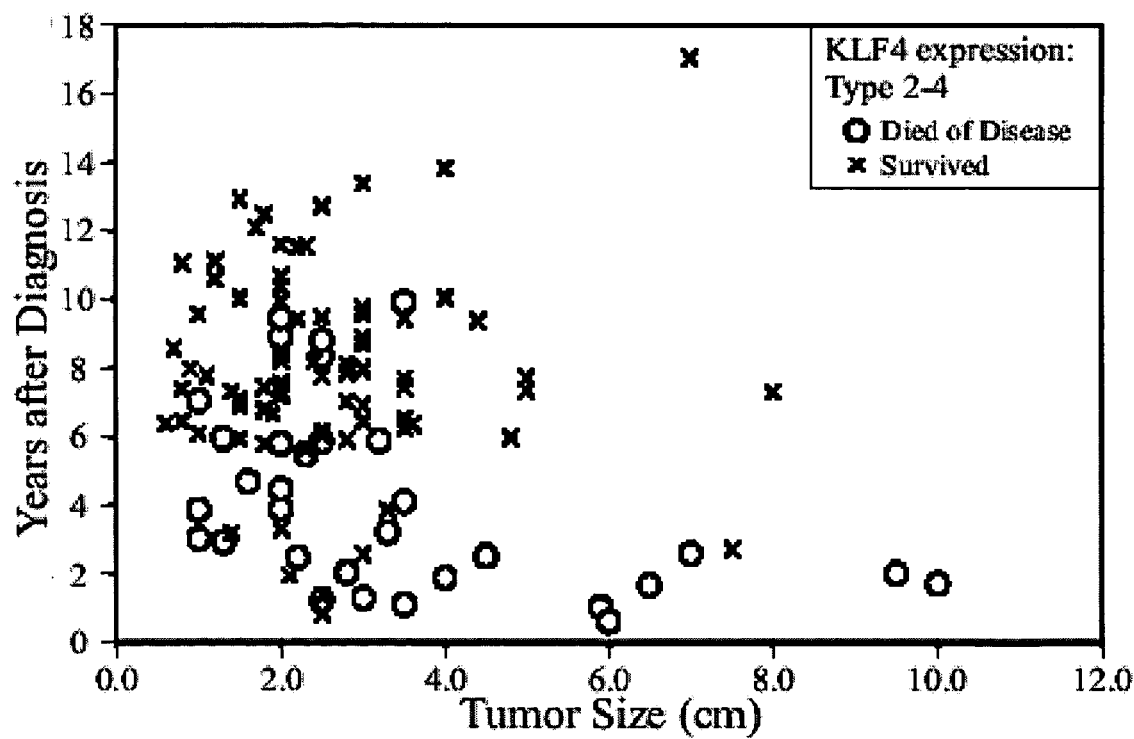

Scatterplot analysis was used to examine the role of tumor size in the association of Type I staining and death due to breast cancer (FIG. 16A). For patients with Type 1 tumors that were ≦2.0 cm, 11 of 15 (73%) died from breast cancer. For patients with Type 1 tumors in the range of 2.01-3.00 cm in size, only 2 of 9 (22%) died from breast cancer (P=0.033). Thus, Type 1 staining identifies a paradoxical subset of cancers in which larger tumor size is associated with a lower rate of death from breast cancer. No such effect was observed for patients with Type 2-4 staining (FIG. 16B). This analysis suggests that any increased risk associated with Type 1 staining may be limited to tumors less than or equal to 2.0 cm in diameter.

In spite of the specific association between Type 1 staining and outcome in small tumors, there was no difference in the overall staining pattern in small vs. large tumors (FIGS. 17A-B). Like the distribution of scores in the two-dimensional plot (FIGS. 17A-B, left panels), the median immunoscores for each subcellular compartment were very similar (for small tumors: cytoplasm=1.30, nucleus=0.43; for large tumors, cytoplasm=1.25, nucleus=0.45). Survival analysis of all patients in the study, regardless of stage at diagnosis, demonstrated the specific association of Type 1 staining and outcome in small tumors (FIG. 17A, right panel; P<0.001). For large tumors, there was no trend toward a worse outcome in patients with Type 1 staining (FIG. 17B, right panel; P=0.398). As a control for the quality of the outcome data for each of the two subgroups, Kaplan-Meier analysis revealed that high histologic grade was associated with death due to breast cancer in both the small tumor (P=0.002) and large tumor subgroups (P=0.026) (not shown).

TABLE 10

Proportion of Patients Surviving Breast Cancer Through The Follow-Up Period By Stage At Diagnosis And KLF4 Staining Pattern

| Stage of Disease at Diagnosis | KLF4 Staining Pattern | | P-Value[a] |
|---|---|---|---|
| | Type 1 (N = 32) Survived/total (%) | Type 2-4 (N = 114) Survived/total (%) | |
| Stage I (T1 N0 M0) | 2/7 (28) | 24/31 (77) | 0.022 |
| Stage IIA (T1 N1 M0) | 2/6 (33) | 13/16 (81) | 0.054 |
| Stage IIA (T2 N0 M0) | 7/7 (100) | 26/30 (87) | 0.570 |
| Stage IIB (T2 N1 M0, T3 N0 M0) | 5/7 (71) | 13/22 (59) | 0.676 |
| Stage III-IV (T1 only) | 0/2 (0) | 1/2 (50) | 0.500 |
| Stage III-IV (T2-T4) | 1/3 (33) | 5/13 (38) | 1.00 |

[a]Values less than 0.100, representing trends or significant differences, are shown in bold.

EXAMPLE 20

Association of Type 1 KFL4 Staining Pattern with Other Parameters

The above results suggest that T1-Type 1 tumors are more likely to recur as distant metastatic lesions, often several years later, leading to eventual death from breast cancer. In order to better characterize this potentially important subset of tumors, the investigators determined whether other known prognostic factors are associated with Type 1 staining (Table 11). Associations were tested for small tumors alone, for large tumors alone, and for all tumors combined.

Compared to patients with T1-Type 2-4 lesions, patients with T1-Type 1 lesions did not exhibit a significant difference in stage at diagnosis (P=0.171). However, high histologic grade was associated with Type 1 staining in small tumors. A high grade was observed in nine of 15 T1-Type 1 cancers (60%). In contrast, only 14 of 49 (29%) T1-Type 2-4 tumors exhibited high grade (P=0.026). For large tumors, no association of histologic grade with Type 1 staining was observed (P=0.252). For small and large tumors combined, histologic grade was more often high in Type 1 than in Type 2-4 tumors (P=0.032).

Two immunohistochemical markers exhibited significantly different expression in Type 1 versus Type 2-4 tumors (all tumors combined). Expression of the proliferation marker Ki67 was more often high for tumors with Type 1 staining patterns (P=0.016). BCL2, for which higher expression was previously associated with a more favorable prognosis, was often low in Type 1 tumors (P=0.032). The observed associations further define the properties of T1-Type 1 tumors. In summary, this group of clinically aggressive tumors is more likely to exhibit high histologic grade, increased proliferation, and reduced expression of the favorable prognostic marker BCL2.

The unadjusted hazard ratio associated with Type 1 staining was determined for three groups of patients: all patients regardless of stage at diagnosis, patients with early stage disease at diagnosis, and patients diagnosed with small primary tumors in the setting of early stage disease (Table 12). Statistical significance was indicated when the 95% confidence interval (CI) of the hazard ratio excluded 1.00. For all patients (N=146), factors significantly associated with a poorer survival included higher stage at diagnosis (hazard ratio, 5.5; 95% CI, 2.88-10.64), positive axillary lymph node status (hazard ratio 3.2; 95% CI, 1.65-6.22), high histologic grade (hazard ratio, 2.8; 95% CI, 1.53-5.24), African-American race (hazard ratio, 2.3; 95% CI, 1.29-4.12), and reduced expression of BCL2 (hazard ratio, 0.4; 95% CI, 0.23-0.83). For patients with early stage cancer (N=97), only Type 1 staining exhibited a significant association with poor outcome (hazard ratio, 2.8; 95% CI, 1.23-6.58). For small tumors in the setting of early stage cancer (N=60), Type 1 staining (hazard ratio, 4.3; 95% CI, 1.75-10.62), high histologic grade (hazard ratio, 3.3; 95% CI, 1.32-8.28), and African-American race (hazard ratio, 2.6; 95% CI, 1.03-6.45) were each significant. In this smaller group of patients, other parameters previously associated with outcome in breast cancer exhibited the expected trend, but did not reach statistical significance (e.g., axillary lymph node status, stage, age, BCL2, P27KIP1, estrogen receptor, and progesterone receptor).

Multivariate analysis indicated that Type 1 staining is independently associated with outcome in patients with early stage disease. For all patients with Stage I or Stage IIA disease, KLF4 was the only significant variable remaining, with an adjusted hazard ratio of 2.6 (95% CI, 1.10-6.05; P=0.029). The failure of other known risk factors such as nodal status, stage, or estrogen receptor status to exhibit significance is attributed to the small sample size of this initial study and to the exclusion of patients with later stage disease from the model.

TABLE 11

Association of Clinical, Pathologic, or Immunohistochemical
Parameters With KLF4 Staining Patterns In Breast Tumors

|  | Small Tumors Only (T ≤ 2.0 cm) | | | Large Tumors Only (T > 2.0 cm) | | |
| --- | --- | --- | --- | --- | --- | --- |
|  | KLF4 Type 1 N = 15 | KLF4 Type 2-4 N = 49 | P-value[a] | KLF4 Type 1 N = 17 | KLF4 Type 2-4 N = 65 | P-value |
| Parameter Stage of Disease at Diagnosis: | | | | | | |
| Stage I | 7/15 (47%) | 31/49 (63%) | | N/A | N/A | N/A |
| Stage IIA | 6/15 (40%) | 16/49 (33%) | 0.171 | 7/17 (41%) | 30/65 (46%) | 0.714 |
| Stage >IIA | 2/15 (13%) | 2/49 (4%) | | 10/17 (59%) | 35/65 (54%) | |
| Histologic Grade: | | | | | | |
| High Grade Marker Expression: | 9/15 (60%) | 14/49 (29%) | 0.026 | 13/17 (76%) | 40/65 (62%) | 0.252 |
| Ki67 high | 9/15 (60%) | 10/31 (32%) | 0.076 | 14/16 (88%) | 27/45 (60%) | 0.044 |
| BCL2 high | 6/15 (40%) | 21/31 (68%) | 0.073 | 4/16 (25%) | 21/45 (47%) | 0.133 |
| ERBB2 high | 5/15 (33%) | 17/31 (55%) | 0.171 | 8/16 (50%) | 22/45 (49%) | 0.939 |
| p53 positive | 4/14 (29%) | 3/30 (10%) | 0.184 | 3/16 (19%) | 15/50 (30%) | 0.524 |
| ER positive | 11/15 (73%) | 30/40 (75%) | 1.00 | 6/17 (35%) | 29/62 (47%) | 0.428 |
| PR positive | 9/15 (60%) | 22/41 (54%) | 0.673 | 4/17 (24%) | 21/61 (34%) | 0.400 |
| P27KIP1 high | 6/15 (40%) | 18/31 (58%) | 0.250 | 8/16 (50%) | 19/45 (42%) | 0.591 |

[a]P-values refer to the behavior of the parameter in tumors with predominately nuclear expression of KLF4 (Type 1, see FIG. 14B) vs. tumors with other expression patterns (Type 2-4). Values less than 0.100, representing trends or significant differences, are shown in bold. For small and large tumors combined, significant differences were observed for histologic grade (P = 0.032), Ki67 (P = 0.016), and BCL2 (P = 0.032).

TABLE 12

Cox Regression Analysis (Unadjusted Hazard Ratios and 95% Confidence Intervals)
Associations With Disease-Specific Survival[a]

|  | All Tumors[b] Unadjusted Hazard Ratio | 95% CI | Stage I and IIA Only Unadjusted Hazard Ratio | 95% CI | Stage I and IIA, Small Tumors Only Unadjusted Hazard Ratio | 95% CI |
| --- | --- | --- | --- | --- | --- | --- |
| KLF4 (Type 1 vs. Type 2-4) | 1.7 | (0.94-3.22) | 2.8 | (1.23-6.58) | 4.3 | (1.75-10.62) |
| Lymph Nodes (Pos. vs. Neg.) | 3.2 | (1.65-6.22) | 2.1 | (0.81-5.37) | 1.4 | (0.50-3.70) |
| Stage[c] | 5.5 | (2.88-10.64) | 0.7 | (0.29-1.52) | 1.2 | (0.49-3.06) |
| Histologic Grade (High vs. Low) | 2.8 | (1.53-5.24) | 1.9 | (0.84-4.37) | 3.3 | (1.32-8.28) |
| Race (African-American vs. Caucasian) | 2.3 | (1.29-4.12) | 2.0 | (0.85-4.77) | 2.6 | (1.03-6.45) |
| Age (≤50 yrs vs. >50 yrs) | 1.3 | (0.72-2.25) | 1.1 | (0.49-2.57) | 1.4 | (0.54-3.50) |
| BCL2 (> vs. ≤ median immunoscore) | 0.4 | (0.23-0.83) | 0.6 | (0.24-1.34) | 0.5 | (0.19-1.18) |
| Ki67 (> vs. ≤ median immunoscore) | 1.3 | (0.69-2.45) | 0.9 | (0.39-2.19) | 1.5 | (0.60-3.89) |
| p27KIP1 (> vs. ≤ median immunoscore) | 0.6 | (0.31-1.12) | 0.5 | (0.20-1.16) | 0.4 | (0.15-1.00) |
| Estrogen Receptor (positive vs negative) | 0.8 | (0.43-1.35) | 1.4 | (0.57-3.40) | 0.7 | (0.26-2.01) |

TABLE 12-continued

Cox Regression Analysis (Unadjusted Hazard Ratios and 95% Confidence Intervals)
Associations With Disease-Specific Survival[a]

| | All Tumors[b] Unadjusted Hazard Ratio | 95% CI | Stage I and IIA Only Unadjusted Hazard Ratio | 95% CI | Stage I and IIA, Small Tumors Only Unadjusted Hazard Ratio | 95% CI |
|---|---|---|---|---|---|---|
| Progesterone Receptor (positive vs. negative) | 0.6 | (0.32-1.07) | 1.1 | (0.47-2.43) | 0.8 | (0.31-1.89) |

[a]Hazard ratios were considered to be statistically significant when the 95% CI did not include 1.00. Statistically significant associations are highlighted in bold.
[b]The number of patients in each group is indicated in the corresponding panel of FIG. 15.
[c]For all tumors, the comparison was stage > I vs. stage I. For Stage I and IIA Only, the comparison was stage IIA (T1N1M0 and T2N0M0) vs. stage I. For Stage I and IIA, Small Tumors Only, the comparison was stage IIA (T1N1M0) vs. stage I.

EXAMPLE 21

Analysis of KLF4 Subcellular Localization In Vitro

Whether KLF4 functions within the nucleus or cytoplasm to induce transformation in vitro is unknown. This example examines whether KLF4 exhibits localization to the nucleus in transformed RK3E cells in vitro, as observed in the more aggressive subset of early stage breast cancer (T1-Type 1 tumors).

The human KLF4 cDNA was modified at the amino terminus with the HA epitope and cloned into the Moloney murine leukemia virus vector pLJD (obtained from L. T. Chow, UAB). Cell culture, retroviral transduction of RK3E cells (Ruppert et al., 1991), and assay of transforming activity were performed as described (Foster et al., 1999). For focus assays, transduced cells were maintained for 4 weeks in non-selective growth media. For colony morphology assays, transduced cells were selected in 400 ug/ml G418, and colony morphology was scored four weeks later. A population derived from >1000 independently transduced cells was passaged in selective medium and then assayed for expression of HA-KLF4 by immunofluorescence.

To determine whether HA-KLF4 retains similar transforming activity as wild-type, retroviral supernatants were generated as described previously (Foster et al., 1999). Within three weeks following transduction of RK3E epithelial cells, wild-type KLF4 and HA-KLF4 each induced numerous transformed foci upon a background monolayer of contact-inhibited RK3E cells (data not shown). Cells transduced by the empty vector served as a negative control. Colony morphology assay was used as a further measure of transforming activity (Foster et al., 1999). The morphology of cells was examined within established colonies of RK3E cells that survived retroviral transduction and culture in selective growth medium. Unlike the vector control cells, HA-KLF4 cells and KLF4 cells were spindled, highly refractile, and formed dense colonies. These results indicate that HA-KLF4 retains the transforming activity of wild type human KLF4.

Figure 18A:
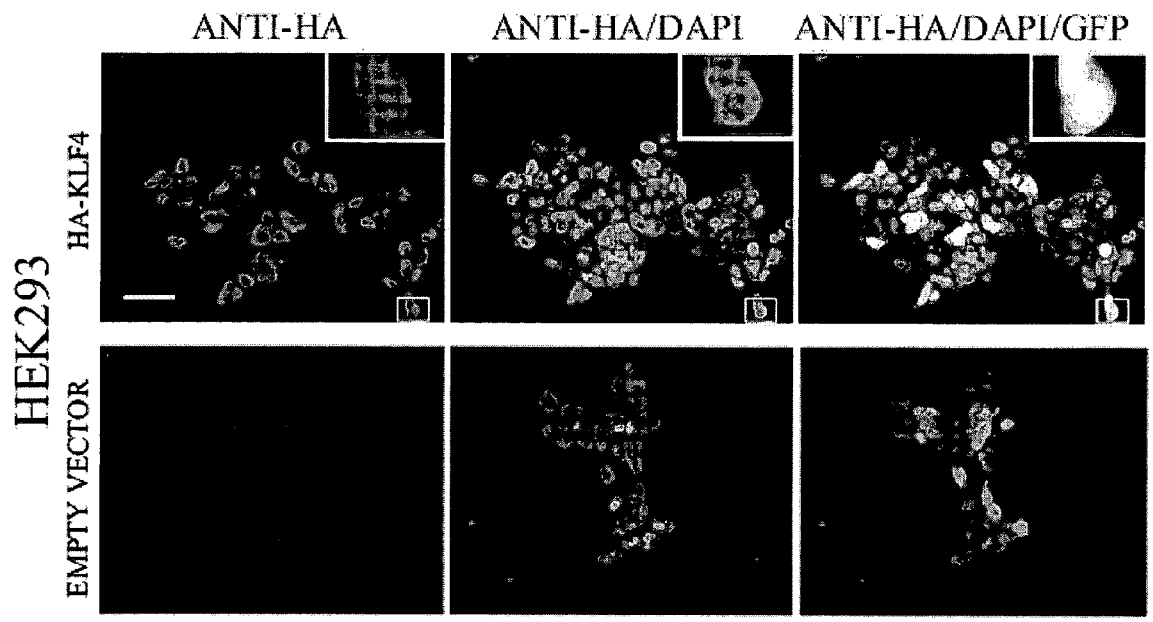
FIGS. 18A-B shows subcellular localization of epitope-tagged KLF4 in vitro.

To test whether the epitope enables identification of HA-KLF4, human embryonic kidney cells HEK293 was examined 48 hours post-transfection with the expression vector pRK5-HA-KLF4 or a vector control (FIG. 18A). The HA-KLF4 cDNA was inserted into pRK5 adjacent to the cytomegalovirus immediate early promoter-enhancer. HEK293 embryonic kidney epithelial cells were plated on poly-L-lysine coated coverslips, grown to 50% confluence, then transfected using the lipid reagent transIT-LT1 (Mirus). To enable identification of transfected cells, a GFP expression vector (pEGFP, Clontech) was included in the transfection mixture. Cells were fixed in 4% paraformaldehyde in PBS for 10 minutes at room temperature, treated with 0.5% triton X-100 in PBS for 10 minutes at 4° C., and then blocked in 50% (v/v) goat serum in PBS (blocking solution). Anti-HA monoclonal antibody 12CA5 (Roche) was used at 4.0 ug/ml in blocking solution for 45 minutes in a humidified chamber. Bound antibody was detected using goat anti-mouse IgG conjugated to Alexa Fluor[R] 594 (Molecular Probes). Where indicated, the cytoplasm was stained using Alexa Fluor[R] 488 phalloidin (Molecular Probes). Nuclei were stained using DAPI at 0.3 mM in PBS, rinsed briefly, mounted using Prolong Antifade medium (Molecular Probes), and then stored in the dark at −20° C. for subsequent examination.

As shown in FIG. 18, HA-KLF4 exhibited two frequent patterns of subcellular localization. In a subset of cells, expression was localized almost entirely within the nucleus. In another subset, representing approximately one-half of all positive cells, nuclear staining was associated with a prominent rim of perinuclear staining (FIG. 18A, middle panel, insert). KLF4 expression in the cytoplasm was rarely observed to extend throughout the full extent of the cytoplasm, as shown by co-expression of a GFP control (FIG. 18A, right panel). Similar results were obtained by transfection of MCF7 cells, although the perinuclear rim in these cells was somewhat thinner (not shown). These results provide evidence for a cytosolic anchoring mechanism that may localize KLF4 to the perinuclear region in cultured epithelial cells, analogous to mechanisms that regulate other transcription factor oncogenes.

Figure 18B:
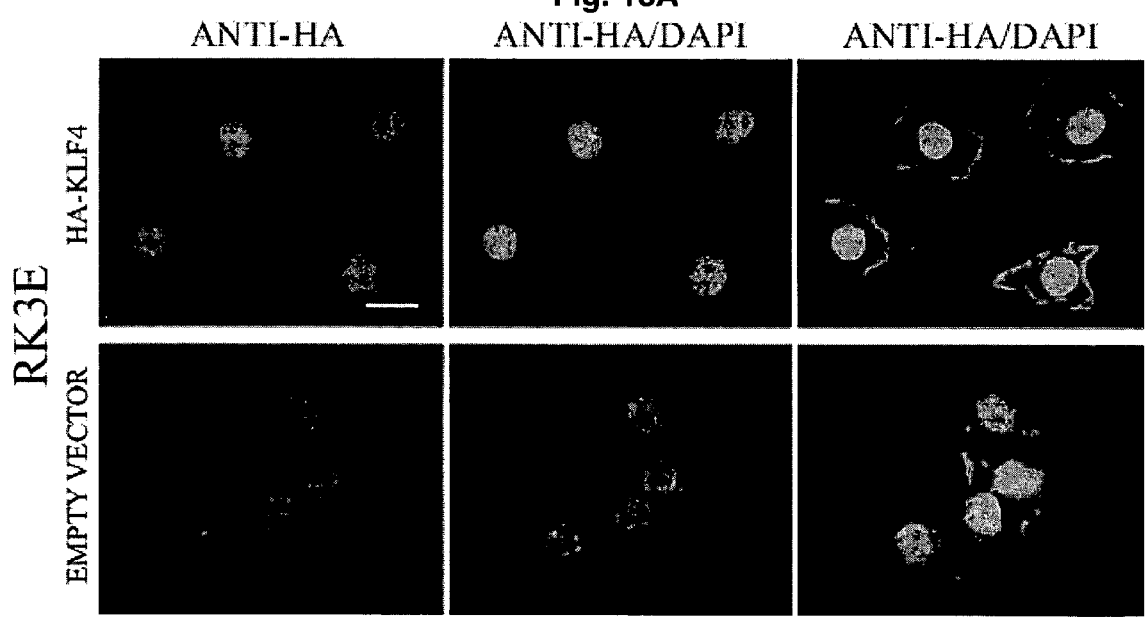

RK3E epithelial cells stably transduced with pLJD-HA-KLF4 were analyzed for expression of the transgene in similar fashion. Fluorescence of the secondary antibody, co-transfected GFP, phalloidin, or DAPI were visualized using an Axioplan 2 Imaging microscope equipped with an external filter wheel (Zeiss). Black and white images were collected using an AxioCam HRc digital camera, and the pseudo-colored images were merged using Axiovision software (version 3.1). As shown in FIG. 18B, the vast majority of expression was localized to the nucleus of transformed RK3E cells. In these cells, perinuclear or cytoplasmic staining was rarely detected (i.e., in less than 5 of 100 cells examined). These results are consistent with a nuclear function of KFL4 during induction of malignant transformation in vitro.

The following references were cited herewith.

Cheng et al., Genes & Development 9: 2335-2349 (1995).
Chomczynski et al., Analytical Biochemistry 162: 156-159 (1987).
Clark, Prognostic and Predictive Factors. In Harris, Lippman, Morrow, and Osborne (eds.), Diseases of the Breast, pp. 489-514. Philadelphia: Lippincott Williams & Wilkins (2000).
Elston and Ellis, Histopathology, 19:403-410 (1991).
Foster et al., Cell Growth Differ. 10:423-434 (1999).
Grizzle, et al., In: Margaret Hanausek and Zbigniew Walaszek (eds.), John Walker's Methods in Molecular Medicine—Tumor marker protocols, pp. 161-179. Totowa, N.J.: Humana Press, Inc., (1998a).
Grizzle, et al., In: Margaret Hanausek and Zbigniew Walaszek (eds.), John Walker's Methods in Molecular Medicine—Tumor Marker Protocols, pp. 143-160. Totowa, N.J.: Humana Press, Inc., (1998b).
Ruppert et al., Mol. Cell Biol. 11: 1724-1728 (1991).
Whitehead et al., Mol. Cell. Biol. 15: 704-710 (1995).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of determining the prognosis of an individual having a breast tumor, comprising the step of:
examining the expression of Krüppel-like factor 4 (KLF4) in said breast tumor by immunohistochemistry, wherein a predominantly cytosolic staining indicates a greater likelihood of survival of the individual, wherein a predominantly nuclear staining and a lower cytosolic staining indicates a lower likelihood of survival.

2. The method of claim 1, wherein said immunohistochemistry employs a monoclonal antibody directed against KLF4 protein.

3. The method of claim 1, wherein said predominantly nuclear staining of KLF4 protein indicates an aggressive phenotype of early stage infiltrating ductal carcinoma.

4. The method of claim 1, wherein said predominantly nuclear staining of KLF4 protein indicates said individual has stage I or stage IIA breast tumor.

5. The method of claim 1, wherein said predominantly nuclear staining of KLF4 protein is detected in tumor smaller or equal to about 2 cm.

6. The method of claim 5, wherein said predominantly nuclear staining of KLF4 protein is detected in tumor having a characteristic selected from the group consisting of high histologic grade, increased expression of Ki67 and reduced expression of BCL2 as compared to tumor without a predominant nuclear staining of KLF4.

7. A method of monitoring a treatment thereby evaluating effectiveness of the treatment in an individual, comprising the step of:
administering a monoclonal antibody to said individual prior to, during and post said treatment, wherein said antibody detects the localization and level of Krüppel-like factor 4 (KLF4) protein, and wherein decreases of nuclear localized KLF4 protein level indicate effective response of said individual to said treatment, so treatment is monitored and the effectiveness of said treatment is evaluated in said individual, wherein said individual suffers from breast carcinoma or oral squamous cell carcinoma.

8. The method of claim 7, wherein said treatment is selected from the group consisting of drug administration, radiation therapy, gene therapy and chemotherapy.

9. A method of monitoring a treatment thereby evaluating effectiveness of the treatment in an individual, comprising the step of:
detecting the expression levels of Krüppel-like factor 4 (KLF4) in said individual prior to, during and post said treatment, wherein decreases of said expression levels of KLF4 indicate effective response of said individual to said treatment, therefore, said treatment is monitored and the effectiveness of said treatment is evaluated in said individual, wherein said individual suffers from breast carcinoma or oral squamous cell carcinoma.

10. The method of claim 9, wherein said treatment is selected from the group consisting of drug administration, radiation therapy, gene therapy and chemotherapy.

* * * * *